(12) United States Patent
Bond et al.

(10) Patent No.: US 8,759,606 B2
(45) Date of Patent: Jun. 24, 2014

(54) STRUCTURED FIBROUS WEB

(75) Inventors: Eric Bryan Bond, Mainville, OH (US); Carola Krippner, Waldems (DE); John Brian Strube, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 451 days.

(21) Appl. No.: 12/477,438

(22) Filed: Jun. 3, 2009

(65) Prior Publication Data
US 2010/0312211 A1 Dec. 9, 2010

(51) Int. Cl.
*A61F 13/538* (2006.01)
*A61F 13/537* (2006.01)

(52) U.S. Cl.
CPC ............ *A61F 13/538* (2013.01); *A61F 13/537* (2013.01); *A61F 13/53713* (2013.01)
USPC ............................ 604/380; 604/378; 604/384

(58) Field of Classification Search
CPC ............ A61F 13/537; A61F 13/53713; A61F 13/538; A61F 2013/5386
USPC ............ 604/367, 378, 380, 381, 384; 428/86, 428/88, 90, 91, 92
See application file for complete search history.

(56) References Cited

U.S. PATENT DOCUMENTS

| | | | |
|---|---|---|---|
| 3,244,785 A | 4/1966 | Hollandsworth | |
| 3,338,992 A | 8/1967 | Kinney et al. | |
| 3,695,025 A * | 10/1972 | Gibbon | 428/85 |
| 3,704,971 A | 12/1972 | Baird et al. | |
| 3,802,817 A | 4/1974 | Matsuki et al. | |
| 3,860,003 A | 1/1975 | Buell | |
| 4,233,014 A | 11/1980 | Kinney | |
| 4,610,678 A | 9/1986 | Weisman et al. | |
| 4,834,735 A | 5/1989 | Alemany et al. | |
| 4,888,231 A | 12/1989 | Angstadt | |
| 4,940,464 A | 7/1990 | Van Gompel | |
| 5,037,416 A | 8/1991 | Allen et al. | |
| 5,092,861 A | 3/1992 | Nomura et al. | |
| 5,137,537 A | 8/1992 | Herron et al. | |

(Continued)

FOREIGN PATENT DOCUMENTS

| EP | 0 810 078 A1 | 12/1997 |
|---|---|---|
| EP | 1 447 067 A1 | 8/2004 |

(Continued)

OTHER PUBLICATIONS

International Search Report & Written Opinion, PCT/US2010/036346, mailed Sep. 22, 2010, 14 pgs.

(Continued)

*Primary Examiner* — Tan-Uyen T Ho
*Assistant Examiner* — Peter S Vasat
(74) *Attorney, Agent, or Firm* — Christian M. Best; Andrew A. Paul; John P. Colbert

(57) ABSTRACT

The present disclosure is directed to disposable absorbent articles comprising a structured fibrous web, the structured fibrous web comprising thermally stable, hydrophilic fibers that are thermally bonded together using heat producing a base substrate that is thermally stable. The base substrate is textured via mechanical treatment to increase its thickness and optionally modified via over bonding to improve its mechanical and fluid handling properties. The structured fibrous web provides optimal fluid wicking and fluid acquisition capabilities and is directed toward fluid management applications.

26 Claims, 20 Drawing Sheets

(56) References Cited

U.S. PATENT DOCUMENTS

| | | | |
|---|---|---|---|
| 5,151,092 A | 9/1992 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,281,208 A | 1/1994 | Thompson et al. | |
| 5,387,207 A | 2/1995 | Dyer et al. | |
| 5,397,316 A | 3/1995 | LaVon et al. | |
| 5,430,142 A | 7/1995 | Glasser et al. | |
| 5,498,692 A | 3/1996 | Noda | |
| 5,514,324 A | 5/1996 | Bachar | |
| 5,545,371 A | 8/1996 | Lu | |
| 5,554,145 A | 9/1996 | Roe et al. | |
| 5,569,234 A | 10/1996 | Buell et al. | |
| 5,571,096 A | 11/1996 | Dobrin et al. | |
| 5,643,653 A | 7/1997 | Griesbach et al. | |
| 5,650,222 A | 7/1997 | DesMarais et al. | |
| 5,688,468 A | 11/1997 | Lu | |
| 5,885,909 A | 3/1999 | Rudisill et al. | |
| 5,897,545 A | 4/1999 | Kline et al. | |
| 5,925,026 A | 7/1999 | Arteman et al. | |
| 5,957,908 A | 9/1999 | Kline et al. | |
| 5,961,506 A | 10/1999 | Guidotti et al. | |
| 5,994,614 A | 11/1999 | Wada et al. | |
| 6,004,306 A | 12/1999 | Robles et al. | |
| 6,028,241 A * | 2/2000 | Armstead | 604/367 |
| 6,120,487 A | 9/2000 | Ashton | |
| 6,120,489 A | 9/2000 | Johnson | |
| 6,140,551 A * | 10/2000 | Niemeyer et al. | 604/367 |
| 6,160,199 A * | 12/2000 | Noda | 604/367 |
| 6,228,462 B1 * | 5/2001 | Lee et al. | 428/132 |
| 6,548,431 B1 | 4/2003 | Bansal et al. | |
| 6,746,766 B2 | 6/2004 | Bond et al. | |
| 6,818,295 B2 | 11/2004 | Bond et al. | |
| 6,908,292 B2 | 6/2005 | Geus et al. | |
| 6,918,750 B2 | 7/2005 | Geus et al. | |
| 6,946,506 B2 | 9/2005 | Bond et al. | |
| 7,102,054 B1 | 9/2006 | Cree et al. | |
| 7,132,585 B2 | 11/2006 | Kudo et al. | |
| 7,172,801 B2 * | 2/2007 | Hoying et al. | 428/92 |
| 7,195,620 B2 * | 3/2007 | Mizutani et al. | 604/385.17 |
| 7,670,665 B2 * | 3/2010 | Hoying et al. | 428/133 |
| 2003/0091803 A1 | 5/2003 | Bond et al. | |
| 2003/0092343 A1 | 5/2003 | Bond et al. | |
| 2003/0094719 A1 | 5/2003 | Yang et al. | |
| 2003/0109602 A1 | 6/2003 | Mogi et al. | |
| 2003/0109605 A1 | 6/2003 | Bond et al. | |
| 2003/0113394 A1 | 6/2003 | Geus et al. | |
| 2003/0178742 A1 | 9/2003 | Geus et al. | |
| 2003/0233082 A1 | 12/2003 | Kline et al. | |
| 2004/0131820 A1 | 7/2004 | Turner et al. | |
| 2004/0162536 A1 | 8/2004 | Becker et al. | |
| 2004/0229008 A1 | 11/2004 | Hoying et al. | |
| 2004/0265533 A1 | 12/2004 | Hoying et al. | |
| 2004/0265534 A1 | 12/2004 | Curro et al. | |
| 2005/0107759 A1 | 5/2005 | Waksmundzki et al. | |
| 2005/0279470 A1 | 12/2005 | Redd et al. | |
| 2006/0286343 A1 | 12/2006 | Curro et al. | |
| 2007/0057414 A1 | 3/2007 | Hartge | |
| 2008/0008853 A1 | 1/2008 | Hupp et al. | |
| 2008/0234476 A1 | 9/2008 | Phan et al. | |
| 2008/0312628 A1 | 12/2008 | Hundorf et al. | |
| 2010/0310810 A1 | 12/2010 | Bond et al. | |
| 2010/0310837 A1 | 12/2010 | Bond et al. | |
| 2010/0310845 A1 | 12/2010 | Bond et al. | |
| 2010/0312208 A1 | 12/2010 | Bond et al. | |
| 2010/0312212 A1 | 12/2010 | Bond et al. | |

FOREIGN PATENT DOCUMENTS

| | | |
|---|---|---|
| EP | 1 634 556 A1 | 3/2006 |
| EP | 1 767 177 A1 | 3/2007 |
| EP | 1 340 843 B1 | 12/2007 |
| EP | 1 323 852 B1 | 8/2008 |
| WO | WO 95/16746 | 6/1995 |
| WO | WO 2004/058117 A1 | 7/2004 |
| WO | WO 2004/058214 A1 | 7/2004 |
| WO | WO 2004/059061 A1 | 7/2004 |
| WO | WO 2005/009275 A2 | 2/2005 |
| WO | WO 2007/001270 A1 | 1/2007 |
| WO | WO 2008/005500 A2 | 1/2008 |
| WO | WO2008/078248 | 7/2008 |
| WO | WO 2008/155699 A1 | 12/2008 |
| WO | WO 2008/155722 A2 | 12/2008 |

OTHER PUBLICATIONS

International Search Report, PCT/US2010/037146, mailed Oct. 25, 2010, 15 pages.
International Search Report, PCT/US2010/037059, mailed Oct. 6, 2010, 14 pages.
International Search Report, PCT/US2010/036577, mailed Jan. 24, 2011, 9 pages.
International Search Report, PCT/US2010/037145, dated Oct. 13, 2010, 12 pages.
International Search Report, PCT/US2010/037061, dated Sep. 15, 2010, 13 pages.
Albin Turbak "Nonwovens: Theory, Process, Performance, and Testing" Tappi Journal 1997, pp. 39-53.
"Tailor-Made Polypropylene and Bicomponent Fibers for the Nonwovens Industry" Tappi Journal Dec. 1991, p. 103.
J D Lindsay, "The Anisotropic Permeability of Paper", Tappi Journal, May 1990, pp. 223-229.
U.S. Appl. No. 12/477,473, filed Jun. 3, 2009, Eric Bryan Bond, et al.
U.S. Appl. No. 12/477,462, filed Jun. 3, 2009, Eric Bryan Bond, et al.
U.S. Appl. No. 12/477,449, filed Jun. 3, 2009, Eric Bryan Bond, et al.
U.S. Appl. No. 12/477,588, filed Jun. 3, 2009, Eric Bryan Bond, et al.
U.S. Appl. No. 12/477,600, filed Jun. 3, 2009, Eric Bryan Bond, et al.
Carson, et al., "Esters of Lima Bean Pod and Corn Cob Hemicelluloses", *Journal of the American Chemical Society*, vol. 70, pp. 293-295 (Jan. 1, 1948).
Le Digabel, et al., "Effects of lignin content on the properties of lignocellulose-based biocomposite", *Carbohydrate Polymers, Applied Science Publishers, Ltd.*, vol. 66, No. 4, pp. 534-545 (Nov. 23, 2006).
All Office Actions, U.S. Appl. No. 12/477,473.
All Office Actions, U.S. Appl. No. 12/477,462.
All Office Actions, U.S. Appl. No. 12/477,449.
All Office Actions, U.S. Appl. No. 12/477,588.
All Office Actions, U.S. Appl. No. 12/477,600.

* cited by examiner

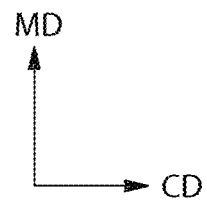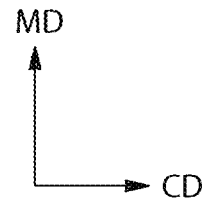
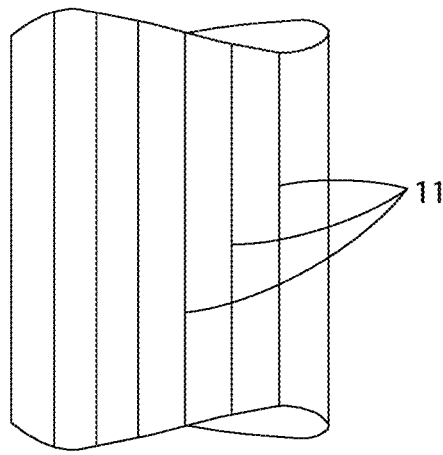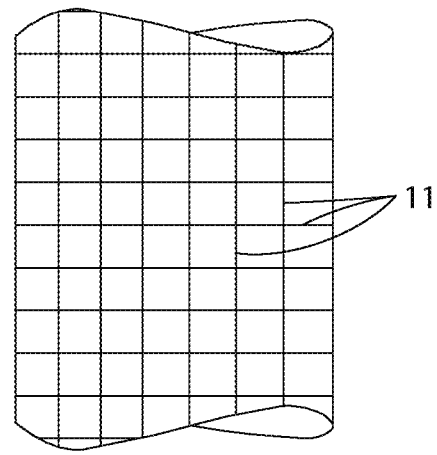
Fig. 12A          Fig. 12B
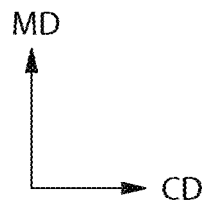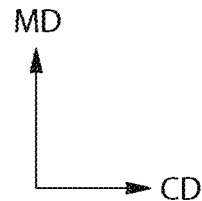
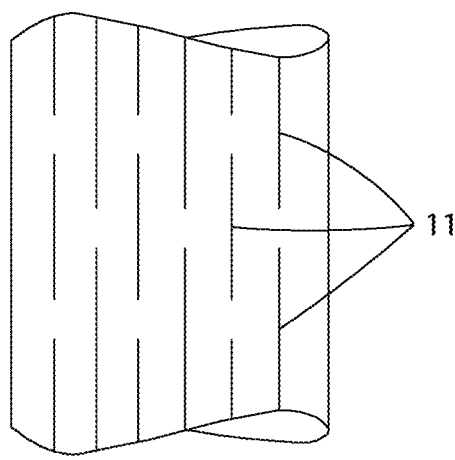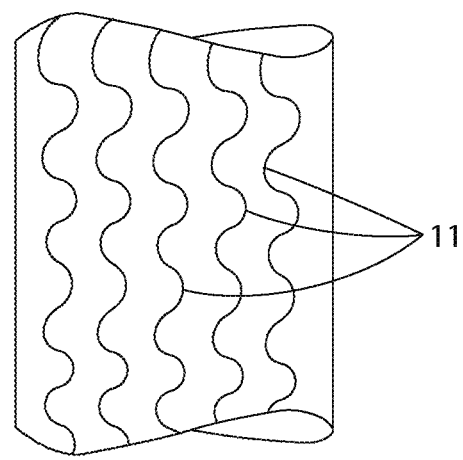
Fig. 12C          Fig. 12D

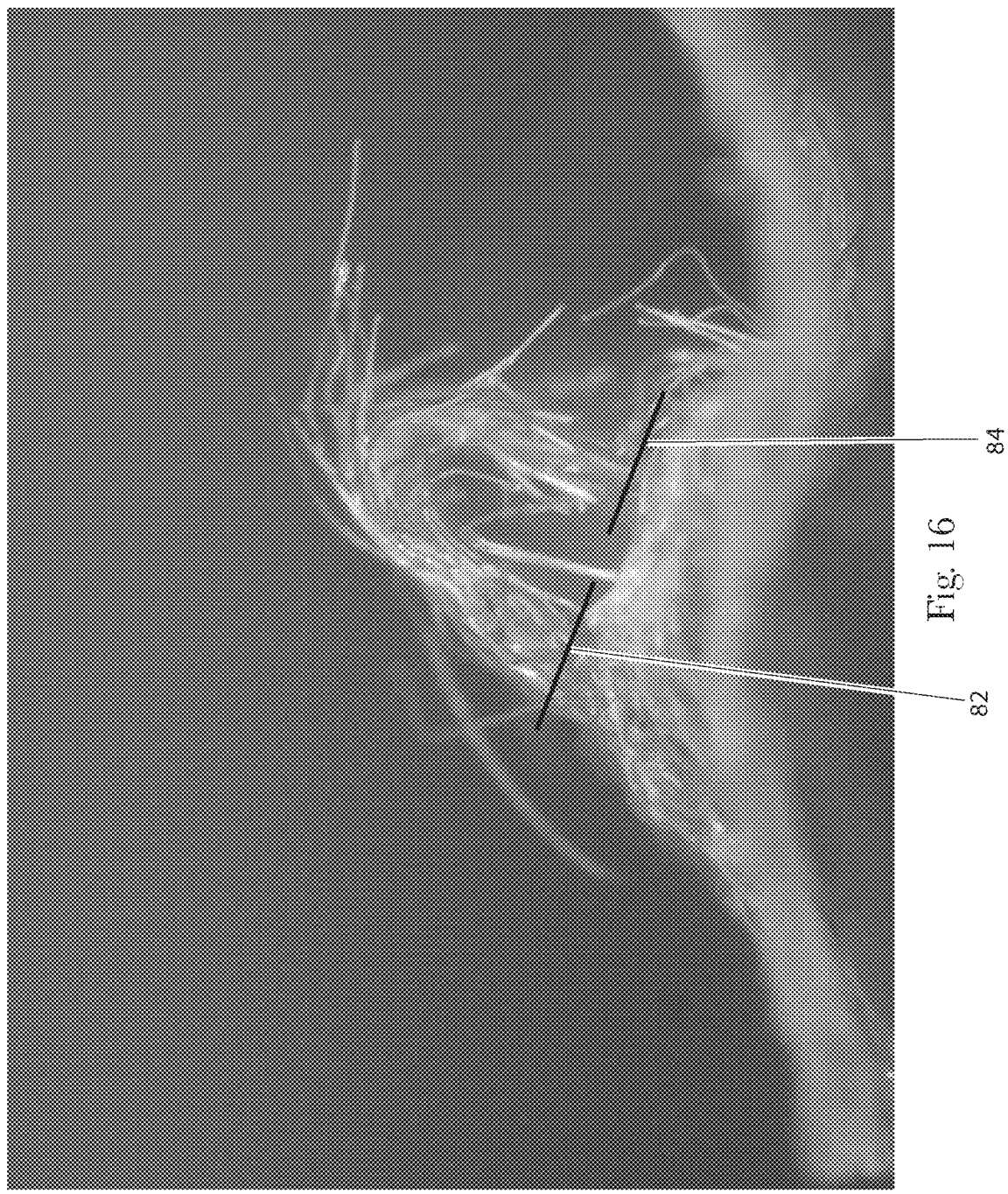

STRUCTURED FIBROUS WEB

FIELD OF THE INVENTION

The present invention is related to fibrous webs, particularly structured fibrous webs providing optimal fluid acquisition and distribution capabilities.

BACKGROUND OF THE INVENTION

Commercial nonwoven fabrics typically comprise synthetic polymers formed into fibers. These fabrics are typically produced with solid fibers that have a high inherent overall density, typically 0.9 g/cm$^3$ to 1.4 g/cm$^3$. The overall weight or basis weight of the fabric is often dictated by a desired opacity, mechanical properties, softness/cushiness, or a specific fluid interaction of the fabric to promote an acceptable thickness or caliper, strength and protection perception. Often, these properties are needed in combination to achieve a particular function or a desired level of performance.

Functionality of nonwoven fabrics is important for many applications. For many nonwoven applications, its function is to provide a desired feel to a product by making it softer or feel more natural. For other nonwoven applications, its function affects the direct performance of the product by making it absorbent or capable of acquiring or distributing fluid. In either case, the function of the nonwoven is often related to the caliper or thickness. For instance, nonwoven fabrics are useful for fluid management applications desiring optimal fluid acquisition and distribution capabilities. Such applications include use in disposable absorbent articles for wetness protection and cleaning applications for fluid and particulate clean-up. In either case nonwoven fabrics are desired for use as a fluid management layer having capacity to acquire and distribute fluid.

The effectiveness of the nonwoven fabric in performing this function is largely dependent upon the thickness or caliper and corresponding void volume of the nonwoven fabric as well as the properties of the fibers used to form it. For many applications caliper also needs to be limited so that bulkiness of the resulting product is minimized. For instance, a disposable absorbent article typically includes a nonwoven topsheet a backsheet and an absorbent core therebetween. In order to control leakage and rewet due to gushing, a fluid acquisition layer that typically comprises at least one nonwoven layer is disposed between the topsheet and the absorbent core. The acquisition layer has capacity to take in fluid and transport it to the absorbent core. The effectiveness of the acquisition layer in performing this function is largely dependent upon the thickness of the layer and the properties of the fibers used to form it. However, thickness leads to bulkiness which is undesirable to the consumer. Therefore, the thickness or caliper of a nonwoven is selected based on a balance of maximum thickness for functionality and minimal thickness for comfort.

In addition, the caliper of a nonwoven fabric is often difficult to maintain due to compressive forces induced during material handling, storage and in some applications, ordinary use. Therefore, for most applications it is desirable for a nonwoven to exhibit a robust caliper that is sustainable through converting, packaging and end use. What's more, high caliper nonwoven fabrics take up more space on rolls during storage. Thus, it is also desirable have a process for increasing the caliper of a nonwoven fabric preferably not until the point in time when it enters the process used in manufacturing a particular end product so that more material can be stored on a roll before it is converted to a final product.

SUMMARY OF THE INVENTION

The present invention is directed to a disposable absorbent articles comprising one or more structured fibrous web(s), the structured fibrous web comprising thermally stable fibers. The fibers and the fibrous web are preferably non extensible. The fibers are non extensible so that they break in the plane of the web during mechanical treatment as described below and stiff to withstand compressive forces during use. The fibers have a modulus of at least 0.5 GPa. The fibers are thermally bonded together using heat, producing a fibrous web base substrate that is thermally stable.

The fibrous web base substrate has a characteristic loft or thickness, based on the fiber size, basis weight and bonding type that is essentially homogenous over a large area. The base substrate includes a first surface and a second surface that are mechanically treated to impart localized out of plane thickness to the base substrate forming a structured fibrous web. The structured fibrous web comprises a first region and a plurality of discrete second regions disposed throughout the first region. The second regions form discontinuities on the second surface of the fibrous web and displaced fibers on the first surface. The displaced fibers are fixed along a first side of the second region and are separated proximate to the first surface along a second side of the second region opposite the first side forming loose ends extending away from the first surface of the fibrous fabric. At least 50% and less than 100% of the displaced fibers have loose ends providing free volume for collecting fluid.

In one embodiment the structured fibrous web includes a plurality of bonded and/or overbonded regions disposed throughout the first region in between the second regions. The bonded and/or overbonded regions can continuously extend between the second regions forming depressions which provide additional void volume for fluid acquisition and channels for fluid distribution.

The structured fibrous web is directed toward fluid management applications desiring optimal fluid acquisition and distribution capabilities.

The present invention provides a disposable absorbent article which may comprise a chassis and an absorbent core. The chassis may contain a topsheet and a backsheet. The absorbent core may be located between the topsheet and the backsheet. The disposable absorbent article further comprises an acquisition system between the topsheet and the absorbent core.

BRIEF DESCRIPTION OF THE DRAWINGS

These and other features, aspects and advantages of the present invention will become better understood with regard to the following description, appended claims, and accompanying drawings where:

FIG. 12*a*-12*f* are plan views of a portion of the structured substrate of the present invention illustrating various patterns of bonded and/or over bond regions.

FIG. 16 is a photomicrograph of a portion of a web of the present invention showing substantial fiber breakage resulting from increased fiber displacement deformation.

DETAILED DESCRIPTION OF THE INVENTION

Figure 1:
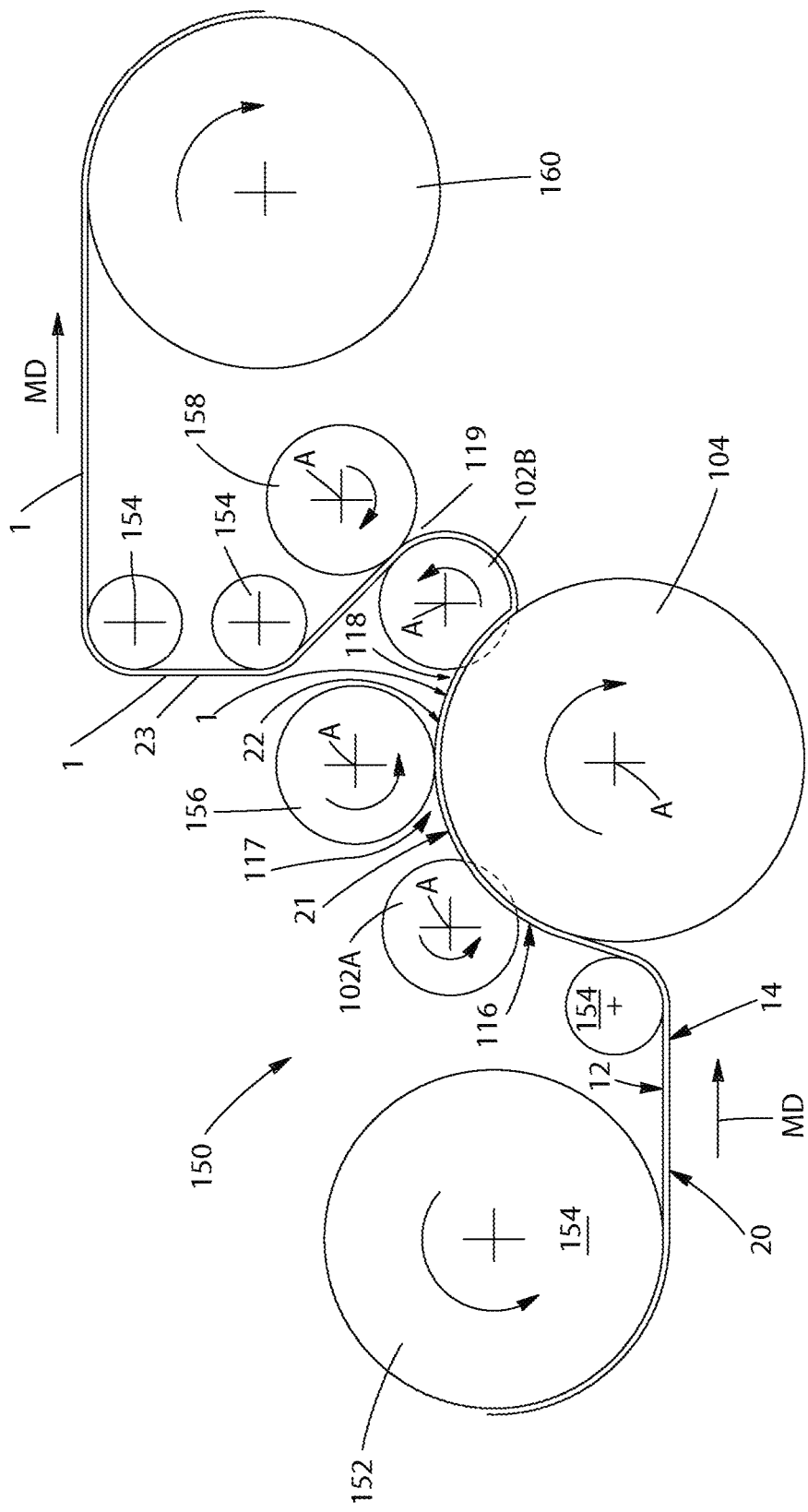
FIG. 1 is a schematic representation of an apparatus for making a web according present invention.

Definitions:

As used herein the term "activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling.

As used herein "depth of engagement" means the extent to which intermeshing teeth and grooves of opposing activation members extend into one another.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaid, and bonded carded web processes, including carded thermal bonding. The basis weight of nonwoven fabrics is usually expressed in grams per square meter ($g/m^2$). The basis weight of a laminate web is the combined basis weight of the constituent layers and any other added components. Fiber diameters are usually expressed in microns; fiber size can also be expressed in denier, which is a unit of weight per length of fiber. The basis weight of the nonwoven fabrics or laminate webs suitable for use in the present invention can range from 6 $g/m^2$ to 300 $g/m^2$, preferably from 10 $g/m^2$ to 200 $g/m^2$, more preferably from 15 $g/m^2$ to 120 $g/m^2$ and most preferably from 20 $g/m^2$ to 100 $g/m^2$.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced by an externally applied force. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multi-constituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

"Disposed" refers to the placement of one element of an article relative to another element of an article. For example, the elements may be formed (joined and positioned) in a particular place or position as a unitary structure with other elements of the diaper or as a separate element joined to another element of the diaper.

"Extensible nonwoven" is a fibrous nonwoven web that elongates, without rupture or breakage, by at least 50%. For example, an extensible material that has an initial length of 100 mm can elongate at least to 150 mm, when strained at 100% per minute strain rate when tested at 23±2° C. and at 50±2% relative humidity. A material may be extensible in one direction (e.g. CD), but non-extensible in another direction (e.g. MD). An extensible nonwoven is generally composed of extensible fibers.

"Highly extensible nonwoven" is a fibrous nonwoven web that elongates, without rupture or breakage, by at least 100%. For example, a highly extensible material that has an initial length of 100 mm can elongate at least to 200 mm, when strained at 100% per minute strain rate when tested at 23±2° C. and at 50±2% relative humidity. A material may be highly extensible in one direction (e.g. CD), but non-extensible in another direction (e.g. MD) or extensible in the other direction. A highly extensible nonwoven is generally composed of highly extensible fibers.

"Non-extensible nonwoven" is a fibrous nonwoven web that elongates, with rupture or breakage, before 50% elongation is reached. For example, a non-extensible material that has an initial length of 100 mm cannot elongate more than 50 mm, when strained at 100% per minute strain rate when tested at 23±2° C. and at 50±2% relative humidity. A non-extensible nonwoven is non-extensible in both the machine direction (MD) and cross direction (CD).

"Extensible fiber is a fiber that elongates by at least 400% without rupture or breakage, when strained at 100% per minute strain rate when tested at 23±2° C. and at 50±2% relative humidity.

"Highly extensible fiber" is a fiber that elongates by at least 500% without rupture or breakage, when strained at 100% per minute strain rate when tested at 23±2° C. and at 50±2% relative humidity.

"Non extensible fiber" is a fiber that elongates by less than 400% without rupture or breakage, when strained at 100% per minute strain rate when tested at 23±2° C. and at 50±2% relative humidity.

"Hydrophilic or hydrophilicity" refers to a fiber or nonwoven material in which water or saline rapidly wets out on the surface the fiber or fibrous material. A material that wicks water or saline can be classified as hydrophilic. A way for measuring hydrophilicity is by measuring its vertical wicking capability. For the present invention, a nonwoven material is hydrophilic if it exhibits a vertical wicking capability of at least 5 mm.

"Joined" refers to configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by methods known in the art, e.g. adhesive bonding, thermal bonding, ultrasonic bonding.

"Machine direction" or "MD" is the direction parallel to the direction of travel of the web as it moves through the manufacturing process. Directions within ±45 degrees of the MD are considered to be machine directional. The "cross machine direction" or "CD" is the direction substantially perpendicular to the MD and in the plane generally defined by the web. Directions within less than 45 degrees of the cross direction are considered to be cross directional.

"Outboard" and "inboard" refer, respectively, to the location of an element disposed relatively far from or near to the longitudinal centerline of an absorbent article with respect to a second element. For example, if element A is outboard of element B, then element A is farther from the longitudinal centerline than is element B.

"Wicking" refers to the active fluid transport of fluid through the nonwoven via capillary forces. Wicking rate refers to the fluid movement per unit time, or i.e., how far a fluid has traveled in a specified period of time.

"Acquisition rate" refers to the speed in which a material takes-up a defined quantity of fluid or the amount of time it takes for the fluid to pass through the material.

"Permeability" refers to a relative ability of a fluid to flow through a material in the X-Y plane. Materials with high permeability enable higher fluid flow rates than materials with lower permeability.

"Web" means a material capable of being wound into a roll. Webs may be films, nonwovens, laminates, apertured laminates, etc. The face of a web refers to one of its two dimensional surfaces, as opposed to its edge.

"X-Y plane" means the plane defined by the MD and CD of a moving web or the length.

"Absorbent article" refers to devices that absorb and contain body exudates, and, more specifically, refers to devices that are placed against or in proximity to the body of the wearer to absorb and contain the various exudates discharged from the body. Absorbent articles may include diapers, pants, training pants, adult incontinence undergarments, feminine hygiene products, and the like. As used herein, the term "body fluids" or "body exudates" includes, but is not limited to, urine, blood, vaginal discharges, breast milk, sweat and fecal matter. Preferred absorbent articles of the present invention are diapers, pants and training pants.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

The present invention provides a structured substrate formed by activation of a suitable base substrate. The activation induces fiber displacement and forms a three dimensional texture which increases the fluid acquisition properties of the base substrate. The surface energy of the base substrate can also be modified to increase its fluid wicking properties. The structured substrate of the present invention will be described with respect to a preferred method and apparatus used for making the structured substrate from the base substrate. A preferred apparatus 150 is shown schematically in FIG. 1 and FIG. 2 and discussed more fully below.

Base Substrate

The base substrate 20 according to the present invention is a fluid permeable fibrous nonwoven web formed from a loose collection of thermally stable fibers. The fibers according to the present invention are non extensible which was previously defined as elongating by less than 300% without rupture or breakage; however, the non extensible fibers forming the base substrate of the present invention preferably elongate by less than 200% without rupture or breakage. The fibers can include staple fibers formed into a web using industry standard carding, airlaid, or wetlaid technologies; however, continuous spunbond fibers forming spunlaid nonwoven webs using industry standard spunbond type technologies is preferred. Fibers and spunlaid processes for producing spunlaid webs are discussed more fully below.

The fibers of the present invention may have various cross sectional shapes that include, but are not limited to; round, elliptical, star shaped, trilobal, multilobal with 3-8 lobes, rectangular, H-shaped, C-shaped, I-shape, U-shaped and other various eccentricities. Hollow fibers can also be used. Preferred shapes are round, trilobal and H-shaped. Round fibers are the least expensive and are therefore preferred from an economic standpoint but trilobal shaped fibers provide increased surface area and are therefore preferred from a functional standpoint. The round and trilobal fiber shapes can also be hollow; however, solid fibers are preferred. Hollow fibers are useful because they have a higher compression resistance at equivalent denier than a solid fiber of the same shape and denier.

Fibers in the present invention tend to be larger than those found in typical spunbond nonwovens. Because the diameter of shaped fibers can be hard to determine, the denier of the fiber is often referenced. Denier is defined as the mass of a fiber in grams at 9000 linear meters of length, expressed as dpf (denier per filament). For the present invention, the preferred denier range is greater than 1 dpf and less than 100 dpf.

A more preferred denier range is 1.5 dpf to 50 dpf and a still more preferred range from 2.0 dpf to 20 dpf, and a most preferred range of 4 dpf to 10 dpf.

The loose collection of fibers forming the base substrate of the present invention are bonded in advance of activation and corresponding fiber displacement. A fibrous web can be under bonded so that the fibers have a high level of mobility and tend to pull out from the bond sites under tension or fully bonded with much higher bond site integrity such that the fibers exhibit minimal fiber mobility and tend to break under tension. The non extensible fibers forming the base substrate of the present invention are preferably fully bonded to form a non extensible fibrous web material. As explained more fully below, a non extensible base substrate is preferred for forming the structured substrate via fiber displacement.

Fully bonding of the base substrate can be done in one bonding step, e.g. during manufacturing of the base substrate. Alternatively, there can be more than one bonding step to make the pre-bonded base substrate, e.g., the base substrate can be only lightly bonded or under bonded upon manufacturing to provide sufficient integrity to wind it up. Subsequently, the base substrate may then undergo further bonding steps to obtain a fully bonded web, e.g., immediately prior to subjecting the base substrate to the fiber displacement process of the present invention. Also, there may be bonding steps at any time between base substrate manufacture and fiber displacement. The different bonding steps may also impart different bonding patterns.

Processes for bonding fibers are described in detail in "Nonwovens: Theory, Process, Performance and Testing" by Albin Turbak (Tappi 1997). Typical bonding methods include mechanical entanglement, hydrodynamic entanglement, needle punching, and chemical bonding and/or resin bonding; however, thermal bonding such as thru-air bonding utilizing heat and thermal point bonding utilizing pressure and heat are preferred with thermal point bonding being most preferred.

Thru-air bonding is performed by passing a heated gas through a collection of fibers to produce a consolidated nonwoven web. Thermal point bonding involves applying heat and pressure to discrete locations to form bond sites on the nonwoven web. The actual bond sites include a variety of shapes and sizes; including but not limited to oval, round and four sided geometric shapes. The total overall thermal point bond area is between 2% and 60%, preferably between 4% and 35%, more preferably between 5% and 30% and most preferably between 8% and 20%. A fully bonded base substrate of the present invention has a total overall bond area of from 8% to 70%, preferably from 12% to 50%, and most preferably between 15% and 35%. The thermal point bonding pin density is between 5 pins/cm$^2$ and 100 pins/cm$^2$, preferably between 10 pins/cm$^2$ and 60 pins/cm$^2$ and most preferably between 20 pins/cm$^2$ and 40 pins/cm$^2$. A fully bonded base substrate of the present invention has a bonding pin density of from 10 pins/cm$^2$ to 60 pins/cm$^2$, preferably from 20 pins/cm$^2$ to 40 pins/cm$^2$.

Thermal bonding requires fibers formed from thermally bondable polymers, such as thermoplastic polymers and fiber made therefrom. For the present invention, the fiber composition includes a thermally bondable polymer. The preferred thermally bondable polymer comprises polyester resin, preferably PET resin, more preferably PET resin and coPET resin providing thermally bondable, thermally stable fibers as discussed more fully below. For the present invention, the thermoplastic polymer content is present at a level of greater than about 30%, preferably greater than about 50%, more preferably greater than about 70%, and most preferably greater than about 90% by weight of the fiber.

As a result of bonding, the base substrate has mechanical properties in both the machine direction (MD) and cross machine direction (CD). The MD tensile strength is between 1 N/cm and 200 N/cm, preferably between 5 N/cm and 100 N/cm, more preferably between 10 N/cm and 50 N/cm and most preferably between 20 N/cm and 40 N/cm. The CD tensile strength is between 0.5 N/cm and 50 N/cm, preferably between 2 N/cm and 35 N/cm, and most preferably between 5 N/cm and 25 N/cm. The base substrate should also have a characteristic ratio of MD to CD tensile strength ratio between 1.1 and 10, preferably between 1.5 and 6 and most preferably between 1.8 and 5.

The bonding method also influences the thickness of the base substrate. The base substrate thickness or caliper is also dependent on the number, size and shape of fiber present in a given measured location. The base substrate thickness is between 0.10 mm and 1.3 mm, more preferably between 0.15 mm and 1.0 mm and most preferably between 0.20 mm and 0.7 mm.

The base substrate also has a characteristic opacity. Opacity is a measure of the relative amount of light that passes through the base substrate. Without wishing to be bound by theory, it is believed that the characteristic opacity depends on the number, size, type, morphology, and shape of fibers present in a given measured location. Opacity can be measured using TAPPI Test Method T 425 om-01 "Opacity of Paper (15/d geometry, Illuminant A/2 degrees, 89% Reflectance Backing and Paper Backing)". The opacity is measured as a percentage. For the present invention, the base substrate opacity is greater than 5%, preferably greater than 10%, more preferably greater than 20%, still more preferably greater than 30% and most preferably greater than 40%.

A relatively high opacity is desirable as the structured fibrous web, being comprised by an acquisition system of a disposable absorbent article, can help in disguising possible staining of the underlying absorbent core. Staining of the absorbent core can be due to the absorption of body fluids such as urine or bowl movement of low viscosity. The current trend in absorbent articles is to reduce the basis weight of the different absorbent article components for cost saving reasons. Thus, if a low basis weight topsheet is applied, the topsheet will likely have lower opacity compared to a high basis weight topsheet. Also, if an apertured topsheet is applied, the apertures also allow to see the underlying layers of the absorbent article, such as the acquisition system and the absorbent core. Therefore, high opacity of the structured fibrous web is especially desirable in embodiments, wherein the absorbent article uses a low basis weight topsheet and/or an apertured topsheet. In one embodiment of the present invention, the disposable absorbent article comprises a topsheet having a basis weight of from 5 g/m$^2$ to 25 g/m$^2$, more preferably from 8 g/m$^2$ to 16 gm$^2$.

The base substrate has a characteristic basis weight and a characteristic density. Basis weight is defined as a fiber/nonwoven mass per unit area. For the present invention, the basis weight of the base substrate is between 10 g/m$^2$ and 200 g/m$^2$. The base substrate density is determined by dividing the base substrate basis weight by the base substrate thickness. For the present invention the density of the base substrate is between 14 kg/m$^3$ and 200 kg/m$^3$. The base substrate also has a base substrate specific volume which is an inverse of the base substrate density measured in cubic centimeters per gram.

Base Substrate Modification

In the present invention, the base substrate can be modified to optimize its fluid dispersion and acquisition properties for use in products where fluid management is important. The fluid dispersion properties can be enhanced by changing the surface energy of the base substrate to increase hydrophilicity and corresponding wicking properties. Modifying the surface energy of the base substrate is optional and is typically performed as the base substrate is made. The fluid acquisition properties can be influenced by modifying the structure of the base substrate by fiber displacement to introduce a 3D texture which increases the thickness or loft and corresponding specific volume of the substrate.

Surface Energy

Hydrophilicity of the base substrate relates to the surface energy. The surface energy of the base substrate can be modified through topical surface treatments, chemical grafting to the surface of the fibers or reactive oxidization of the fiber surfaces via plasma or corona treatments then further chemical bonding from gas reaction addition.

The surface energy of the base substrate can also be influenced by the polymeric material used in producing the fibers of the base substrate. The polymeric material can either have inherent hydrophilicity or it can be rendered hydrophilic through chemical modification of the polymer, fiber surface, and base substrate surface through melt additives or combination of the polymeric material with other materials that induce hydrophilic behavior. Examples of materials used for polypropylene are IRGASURF® HL560 from Ciba and a PET copolymer from Eastman Chemical, EASTONE® family of polymeric materials for PET.

Surface energy can also be influenced through topical treatments of the fibers. Topical treatment of fiber surfaces generally involves surfactants that are added in an emulsion via foam, spray, kiss-roll or other suitable technique in a diluted state and then dried. Polymers that might require a topical treatment are polypropylene or polyester terephthalate based polymer systems. Other polymers include aliphatic polyesteramides; aliphatic polyesters; aromatic polyesters including polyethylene terephthalates and copolymers, polybutylene terephthalates and copolymers; polytrimethylene terephthalates and copolymers; polylactic acid and copolymers. A category of materials referred to as soil release polymers (SRP) are also suitable for topical treatment. Soil release polymers are a family of materials that include low molecular weight polyester polyether, polyester polyether block copolymer and nonionic polyester compounds. Some of these materials can be added as melt additives, but their preferred usage is as topical treatments. Commercial examples of this category of materials are available from Clariant as the Texcare™ family of products.

Structured Substrate

The second modification to the base substrate 20 involves mechanically treating the base substrate to produce a structured fibrous web substrate (the terms "structured fibrous web" and "structured substrate" are used interchangeably herein). The structured substrate is defined as (1) a base substrate permanently deformed through fiber rearrangement and fiber separation and breakage producing permanent fiber dislocation (referred to hereinafter as "fiber displacement") such that the structured substrate has a thickness value which is higher than that of the base substrate and optionally (2) a base substrate modified by over bonding (referred to hereinafter as "over bonding") to form a compressed region below the thickness of the base substrate. Fiber displacement processes involve permanent mechanical displacement of fibers via rods, pins, buttons, structured screens or belts or other suitable technology. The permanent fiber dislocation provides additional thickness or caliper compared to the base substrate. The additional thickness increases specific volume of the substrate and also increases fluid permeability of the substrate. The over bonding improves the mechanical properties of the base substrate and can enhance the depth of channels in between displaced fiber regions for fluid management.

Fiber Displacement

Figure 3:
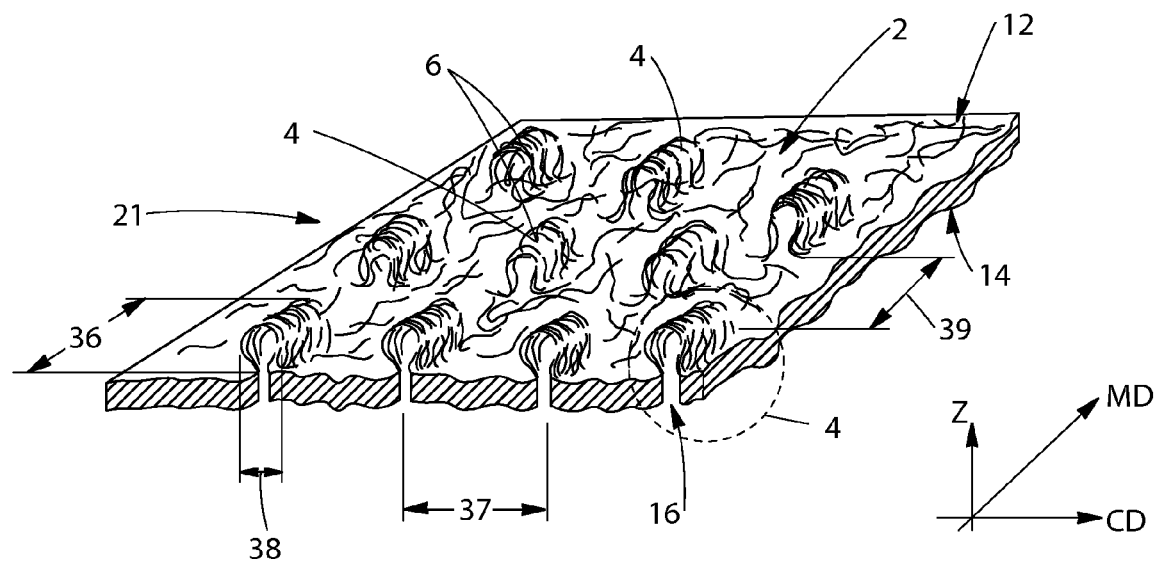
FIG. 3 is a partial perspective view of a structured substrate.
Figure 4:
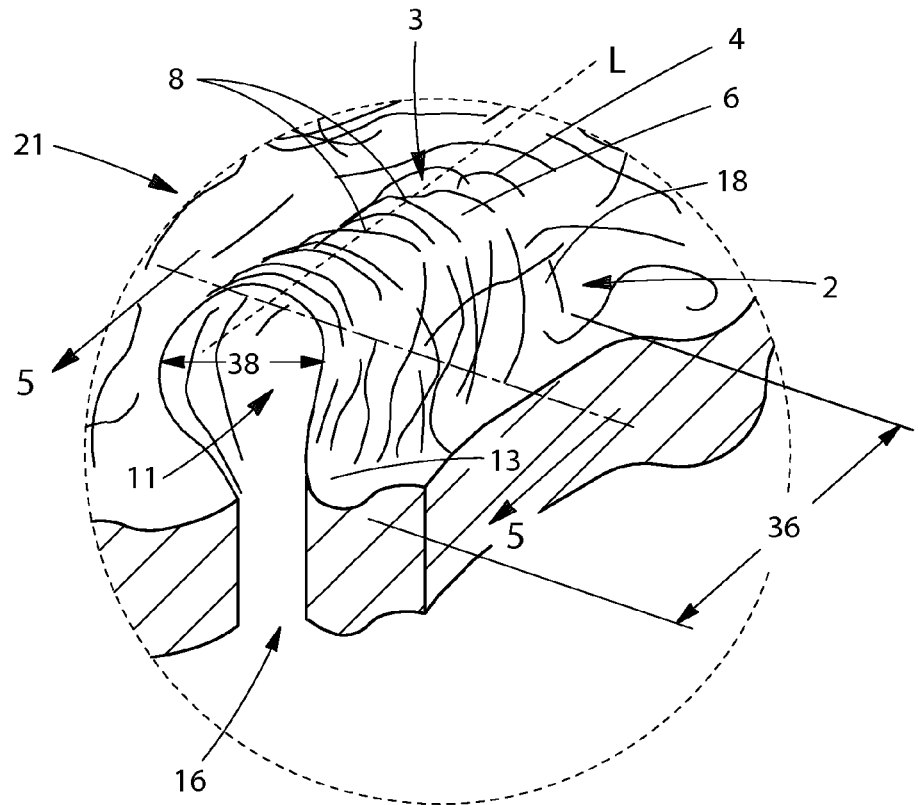
FIG. 4 is an enlarged portion of the structured substrate shown in FIG. 3.

The base substrate previously described can be processed using the apparatus 150 shown in FIG. 1 to form structured substrate 21, a portion of which is shown in FIGS. 3-6. As shown in FIG. 3, the structured substrate has a first region 2 in the X-Y plane and a plurality of second regions 4 disposed throughout the first region 2. The second regions 4 comprise displaced fibers 6 forming discontinuities 16 on the second surface 14 of the structured substrate 21 and displaced fibers 6 having loose ends 18 extending from the first surface 12. As shown in FIG. 4, the displaced fibers 6 extend from a first side 11 of the second region 4 and are separated and broken forming loose ends 18 along a second side 13 opposite the first side 11 proximate to the first surface 12. For the present invention, proximate to the first surface 12 means the fiber breakage occurs between the first surface 12 and the peak or distal portion 3 of the displaced fibers, preferably, closer to the first surface 12 than to the distal portion 3 of the displaced fibers 6.

Figure 15:
FIG. 15 is a photomicrograph of a portion of a web of the present invention showing tent-like structures formed at low fiber displacement deformations.

The location of the fiber separation or breakage is primary attributed to the non extendable fibers forming the base substrate; however, displaced fiber formation and corresponding fiber breakage is also influenced by the extent of bonding used in forming the base substrate. A base substrate comprising fully bonded non extensible fibers provides a structure that due to its fiber strength, fiber stiffness, and bonding strength forms tent like structures at low fiber displacement deformations, as shown in the micrograph in FIG. 15. Once the fiber displacement deformation is extended, substantial fiber breakage is observed, typically concentrated on one side as shown in the micrograph in FIG. 16.

The purpose for creating the displaced fibers 6 having loose ends 18 in FIG. 4 is to increase the structured substrate specific volume over the base substrate specific volume by creating void volume. For the present invention it has been found that creating displaced fibers 6 having at least 50% and less than 100% loose ends in the second regions produces a structured substrate having an increased caliper and corresponding specific volume which is sustainable during use. (See Table 6, examples 1N5-1N9 provided below) In certain embodiments described further herein, the loose ends 18 of the displaced fibers 6 can be thermally bonded for improved compression resistance and corresponding sustainability. Displaced fibers 6 having thermally bonded loose ends and a process for producing the same are discussed more fully below.

Figure 5:
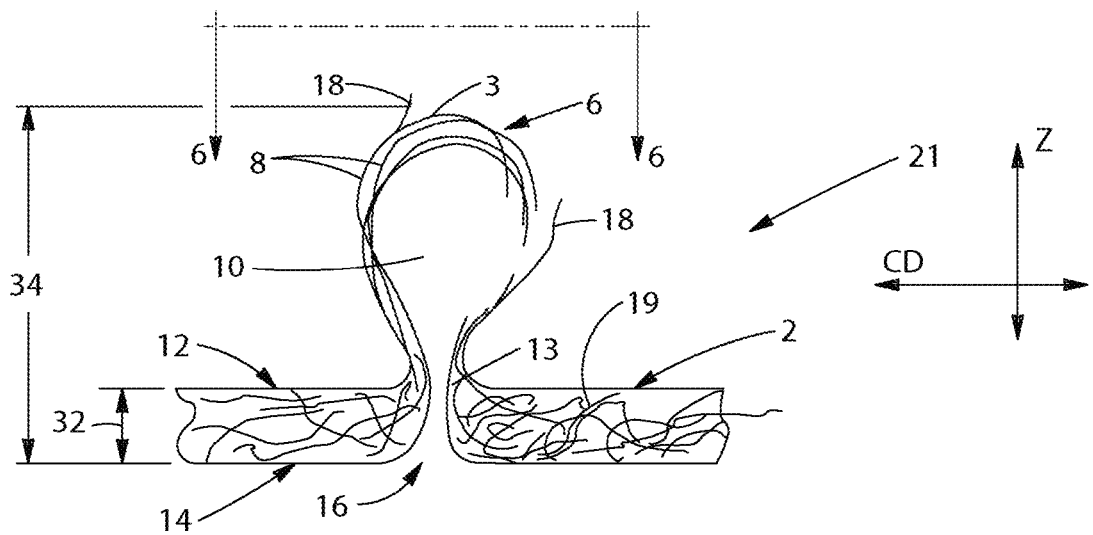
FIG. 5 is a cross-sectional view of a portion of the structured substrate shown in FIG. 4.

As shown in FIG. 5, the displaced fibers 6 in second regions 4 exhibit a thickness or caliper which is greater than the first region 2 thickness 32 which typically will be the same as the base substrate thickness. The size and shape of the second regions 4 having displaced fibers 6 may vary depending on the technology used. FIG. 5 shows a cross section of the structured substrate 21 illustrating displaced fibers 6 in a second region 4. Displaced fiber 6 thickness 34 describes the thickness or caliper of the second region 4 of the structured substrate 21 resulting from the displaced fibers 6. As shown, the displaced fiber thickness 34 is greater than the first region thickness 32. It is preferred that displaced fiber thickness 34 be at least 110% greater than the first region thickness 32, more preferably at least 125% greater, and most preferably at least 150% greater than the first region thickness 32. The aged caliper for displaced fiber thickness 34 is between 0.1 mm and 5 mm, preferably between 0.2 mm and 2 mm and most preferably between 0.5 mm and 1.5 mm.

The number of second regions 4 having displaced fibers 6 per unit area of structured substrate 21 can vary as shown in FIG. 3. In general, the area density need not be uniform across the entire area of structured substrate 21, but second regions 4 can be limited to certain regions of structured substrate 21, such as in regions having predetermined shapes, such as lines, stripes, bands, circles, and the like.

As shown in FIG. 3, the total area occupied by the second regions 4 is less than 75%, preferably less than 50% and more preferably less than 25% of the total area, but is at least 10%. The size of the second regions and spacing between second regions 4 can vary. FIG. 3 and FIG. 4 show the length 36, width 38 and spacing 37 and 39 between second regions 4. The spacing 39 in the machine direction between the second regions 4 shown in FIG. 3 is preferably between 0.1 mm and 1000 mm, more preferably between 0.5 mm and 100 mm and most preferably between 1 mm and 10 mm. The side to side spacing 37 between the second regions 4 in the cross machine direction is between 0.2 mm and 16 mm, preferably between 0.4 mm and 10 mm, more preferably between 0.8 mm and 7 mm and most preferably between 1 mm and 5.2 mm.

As shown in FIG. 1, structured substrate 21 can be formed from a generally planar, two dimensional nonwoven base substrate 20 supplied from a supply roll 152. The base substrate 20 moves in the machine direction MD by apparatus 150 to a nip 116 formed by intermeshing rollers 104 and 102A which form displaced fibers 6 having loose ends 18. The structured substrate 21 having displaced fibers 6 optionally proceeds to nip 117 formed between roll 104 and bonding roll 156 which bonds the loose ends 18 of the displaced fibers 6. From there, structured substrate 22 proceeds to optionally intermeshing rolls 102B and 104 which removes structured substrate 22 from roll 104 and optionally conveys it to nip 119 formed between roll 102B and bonding roll 158 where over bond regions are formed in structured substrate 23 which is eventually taken up on supply roll 160. Although FIG. 1 illustrates the sequence of process steps as described, for base substrates which are not yet fully bonded it is desirable to reverse the process so that bonded regions are formed in the base substrate prior to forming displaced fibers 6. For this embodiment the base substrate 20 would be supplied from a supply roll similar to the take up supply roll 160 shown in FIG. 1 and moved to a nip 119 formed between roll 102B and bonding roll 158 where the substrate is bonded prior to entering nip 118 formed between intermeshing rolls 102B and 104 where displaced fibers 6 having loose ends 18 are formed in the second regions 4.

Although FIG. 1 shows base substrate 20 supplied from supply roll 152, the base substrate 20 can be supplied from any other supply means, such as festooned webs, as is known in the art. In one embodiment, base substrate 20 can be supplied directly from a web making apparatus, such as a nonwoven web-making production line.

As shown in FIG. 1, first surface 12 corresponds to first side of base substrate 20, as well as the first side of structured substrate 21. Second surface 14 corresponds to the second side of base substrate 20, as well as the second side of structured substrate 21. In general, the term "side" is used herein in the common usage of the term to describe the two major surfaces of generally two-dimensional webs, such as nonwovens. Base substrate 20 is a nonwoven web comprising substantially randomly oriented fibers, that is, randomly oriented at least with respect to the MD and CD. By "substantially randomly oriented" is meant random orientation that, due to processing conditions, may exhibit a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a higher percentage of fibers are oriented in the MD as opposed to the CD.

In some embodiments of the present invention it may be desirable to purposely orient a significant percentage of fibers in a predetermined orientation with respect to the MD in the plane of the web. For example, it may be that, due to tooth spacing and placement on roll 104 (as discussed below), it may be desirable to produce a nonwoven web having a predominant fiber orientation at an angle of, for example, 60 degrees off parallel to the longitudinal axis of the web. Such webs can be produced by processes that combine lapping webs at the desired angle, and, if desired carding the web into a finished web. A web having a high percentage of fibers having a predetermined angle can statistically bias more fibers to be formed into displaced fibers in structured substrate 21, as discussed more fully below.

Base substrate 20 can be provided either directly from a web making process or indirectly from a supply roll 152, as shown in FIG. 1. Base substrate 20 can be preheated by means known in the art, such as by heating over oil-heated or electrically heated rollers. For example, roll 154 could be heated to pre-heat the base substrate 20 prior to the fiber displacement process.

As shown in FIG. 1, supply roll 152 rotates in the direction indicated by the arrow as base substrate 20 is moved in the machine direction over roller 154 and to the nip 116 of a first set of counter-rotating intermeshing rolls 102A and 104. Rolls 102A and 104 are the first set of intermeshing rollers of apparatus 150. The first set of intermeshing rolls 102A and 104 operate to form displaced fibers and to facilitate fiber breakage in base substrate 20, to make structured substrate referred to herein after as structured substrate 21. Intermeshing rolls 102A and 104 are more clearly shown in FIG. 2.

Figure 2:
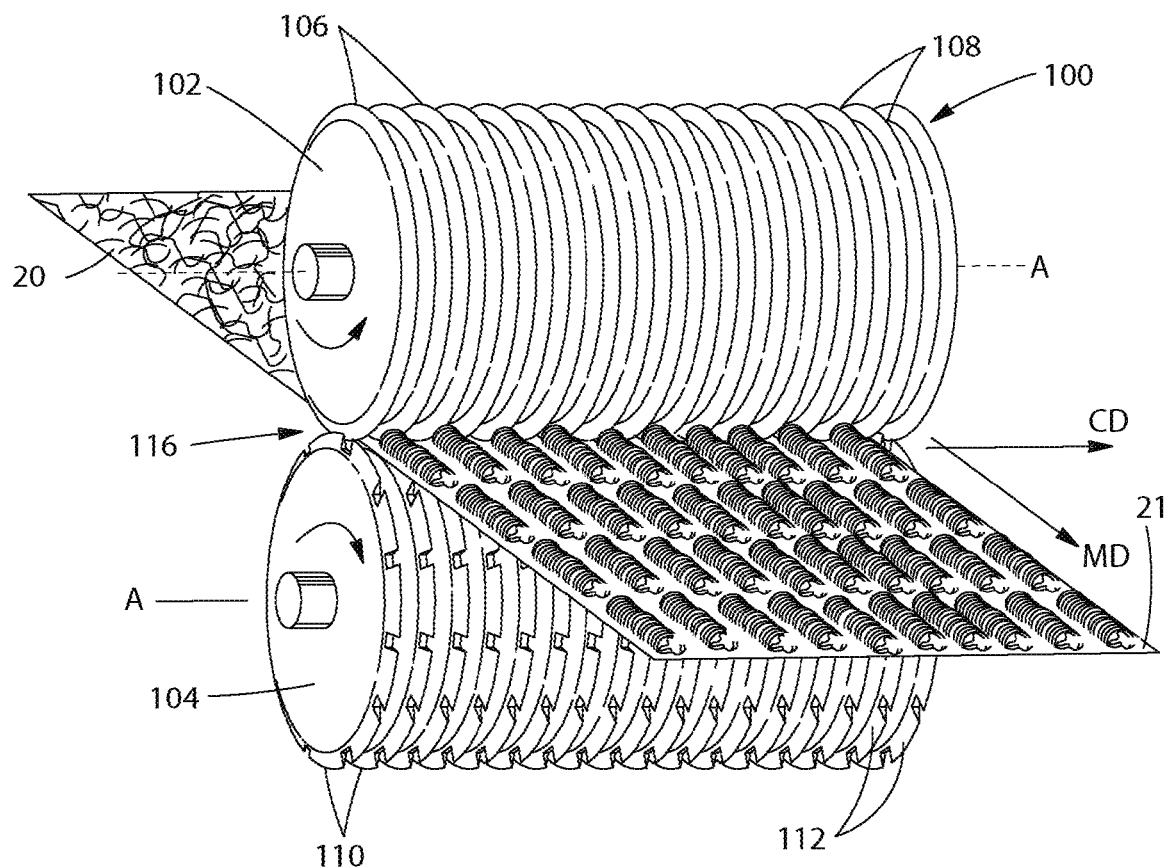
FIG. 2 is an enlarged view of a portion of the apparatus shown in FIG. 1.

Referring to FIG. 2, there is shown in more detail the portion of apparatus 150 for making displaced fibers on structured substrate 21 of the present invention. This portion of apparatus 150 is shown as nip rollers 100 in FIG. 2, and comprises a pair of intermeshing rolls 102 and 104 (corresponding to rolls 102A and 104, respectively, in FIG. 1), each rotating about an axis A, the axes A being parallel in the same plane. Although the apparatus 150 is designed such that base substrate 20 remains on roll 104 through a certain angle of rotation, FIG. 2 shows in principle what happens as base substrate 20 goes through nip 116 on apparatus 150 and exits as structured substrate 21 having regions of displaced fibers 6. The intermeshing rolls can be made from metal or plastic. Non-limiting examples of metal rolls would be aluminum or steel. Non-limiting examples of plastic rolls would be polycarbonate, acrylonitrile butadiene styrene (ABS), and polyphenylene oxide (PPO). The plastics can be filled with metals or inorganic additive materials.

As shown in FIG. 2, roll 102 comprises a plurality of ridges 106 and corresponding grooves 108 which can extend unbroken about the entire circumference of roll 102. In some embodiments, depending on what kind of pattern is desired in structured substrate 21, roll 102 (and, likewise, roll 102A) can comprise ridges 106 wherein portions have been removed, such as by etching, milling or other machining processes, such that some or all of ridges 106 are not circumferentially continuous, but have breaks or gaps. The breaks or gaps can be arranged to form a pattern, including simple geometric patters such as circles or diamonds, but also including complex patterns such as logos and trademarks. In one embodiment, roll 102 can have teeth, similar to the teeth on roll 104, described more fully below. In this manner, it is possible to have displaced fibers 6 on both sides 12, 14 of structured substrate 21.

Roll 104 is similar to roll 102, but rather than having ridges that can extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 7, discussed below. Both or either of rolls 102 and 104 can be heated by means known in the art such as by using hot oil filled rollers or electrically-heated rollers.

As shown in FIG. 3, structured substrate 21 has a first region 2 defined on both sides of structured substrate 21 by the generally planar, two-dimensional configuration of the base substrate 20, and a plurality of discrete second regions 4 defined by spaced-apart displaced fibers 6 and discontinuities 16 which can result from integral extensions of the fibers of the base substrate 20. The structure of second regions 4 is differentiated depending on which side of structured substrate 21 is considered. For the embodiment of structured substrate 21 shown in FIG. 3, on the side of structured substrate 21 associated with first surface 12 of structured substrate 21, each discrete second region 4 can comprise a plurality of displaced fibers 6 extending outwardly from first surface 12 and having loose ends 18. Displaced fibers 6 comprise fibers having a significant orientation in the Z-direction, and each displaced fiber 6 has a base 5 disposed along a first side 11 of the second region 4 proximal to the first surface 12, a loose end 18 separated or broken at a second side 13 of the second region 4 opposite the first side 11 near the first surface 12 and a distal portion 3 at a maximum distance in the Z-direction from the first surface 12. On the side of structured substrate 21 associated with second surface 14, second region 4 comprises discontinuities 16 which are defined by fiber orientation discontinuities 16 on the second surface 14 of structured substrate 21. The discontinuities 16 correspond to the locations where teeth 110 of roll 104 penetrated base substrate 20.

As used herein, the term "integral" as in "integral extension" when used of the second regions 4 refers to fibers of the second regions 4 having originated from the fibers of the base substrate 20. Therefore, the broken fibers 8 of displaced fibers 6, for example, can be plastically deformed and/or extended fibers from the base substrate 20, and can be, therefore, integral with first regions 2 of structured substrate 21. In other words, some, but not all of the fibers have been broken, and such fibers had been present in base substrate 20 from the beginning. As used herein, "integral" is to be distinguished from fibers introduced to or added to a separate precursor web for the purpose of making displaced fibers. While some embodiments of structured substrates 21, 22 and 23 of the present invention may utilize such added fibers, in a preferred embodiment, broken fibers 8 of displaced fibers 6 are integral to structured substrate 21.

It can be appreciated that a suitable base substrate 20 for a structured substrate 21 of the present invention having broken fibers 8 in displaced fibers 6 should comprise fibers having sufficient fiber immobility and/or plastic deformation to break and form loose ends 18. Such fibers are shown as loose fiber ends 18 in FIGS. 4 and 5. For the present invention, loose fiber ends 18 of displaced fibers 6 are desirable for producing void space or free volume for collecting fluid. In a preferred embodiment at least 50%, more preferably at least 70% and less than 100% of the fibers urged in the Z-direction are broken fibers 8 having loose ends 18.

The second regions 4 can be shaped to form patterns in both the X-Y plane and the Z-plane to target specific volume distributions that can vary in shape, size and distribution.

Figure 6:
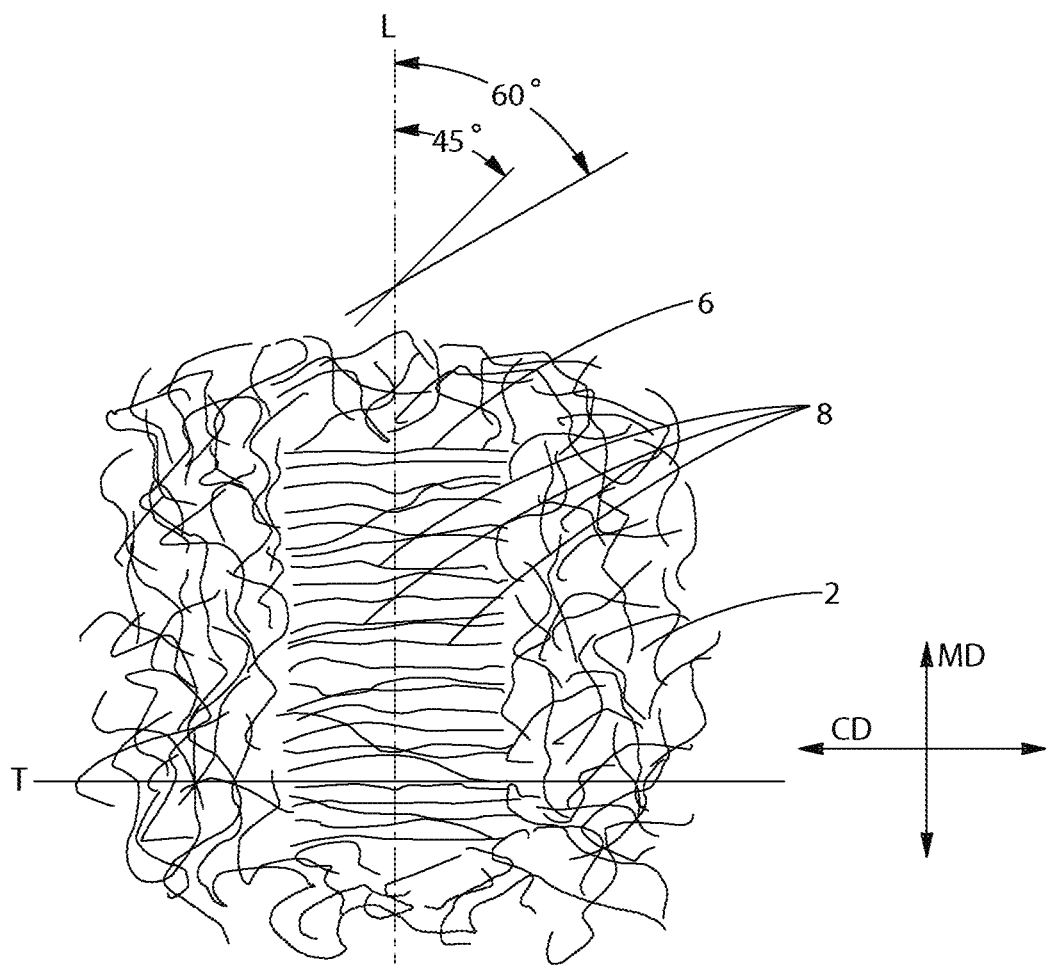
FIG. 6 is a plan view of a portion of the structured substrate shown in FIG. 5.

Representative second region having displaced fibers 6 for the embodiment of structured substrate 21 shown in FIG. 2 is shown in a further enlarged view in FIGS. 3-6. The representative displaced fibers 6 are of the type formed on an elongated tooth 110 on roll 104, such that the displaced fibers 6 comprises a plurality of broken fibers 8 that are substantially aligned such that the displaced fibers 6 have a distinct longitudinal orientation and a longitudinal axis L. Displaced fibers 6 also have a transverse axis T generally orthogonal to longitudinal axis L in the MD-CD plane. In the embodiment shown in FIGS. 2-6, longitudinal axis L is parallel to the MD. In one embodiment, all the spaced apart second regions 4 have generally parallel longitudinal axes L. In preferred embodiments second regions 4 will have a longitudinal orientation, i.e. second regions will have an elongate shape and will not be circular. As shown in FIG. 4, and more clearly in FIGS. 5 and 6, when elongated teeth 110 are utilized on roll 104, one characteristic of the broken fibers 8 of displaced fibers 6 in one embodiment of structured substrate 21 is the predominant directional alignment of the broken fibers 8. As shown in FIGS. 5 and 6, many of broken fibers 8 can have a substantially uniform alignment with respect to transverse axis T when viewed in plan view, such as in FIG. 6. By "broken" fibers 8 is meant that displaced fibers 6 begin on the first side 11 of second regions 4 and are separated along a second side 13 of second regions 4 opposite the first side 11 in structured substrate 21.

As can be understood with respect to apparatus 150, therefore, displaced fibers 6 of structured substrate 21 are made by mechanically deforming base substrate 20 that can be described as generally planar and two dimensional. By "planar" and "two dimensional" is meant simply that the web is flat relative to the finished structured substrate 1 that has distinct, out-of-plane, Z-direction three-dimensionality imparted due to the formation of second regions 4. "Planar" and "two-dimensional" are not meant to imply any particular flatness, smoothness or dimensionality. As base substrate 20 goes through the nip 116 the teeth 110 of roll 104 enter grooves 108 of roll 102A and simultaneously urge fibers out of the plane of base substrate 20 to form second regions 4, including displaced fibers 6 and discontinuities 16. In effect, teeth 110 "push" or "punch" through base substrate 20. As the tip of teeth 110 push through base substrate 20 the portions of fibers that are oriented predominantly in the CD and across teeth 110 are urged by the teeth 110 out of the plane of base substrate 20 and are stretched, pulled, and/or plastically deformed in the Z-direction, resulting in formation of second region 4, including the broken fibers 8 of displaced fibers 6. Fibers that are predominantly oriented generally parallel to the longitudinal axis L, i.e., in the machine direction of base substrate 20, can be simply spread apart by teeth 110 and remain substantially in the first region 2 of base substrate 20.

In FIG. 2, the apparatus 100 is shown in one configuration having one patterned roll, e.g., roll 104, and one non-patterned grooved roll 102. However, in certain embodiments it may be preferable to form nip 116 by use of two patterned rolls having either the same or differing patterns, in the same or different corresponding regions of the respective rolls.

Such an apparatus can produce webs with displaced fibers 6 protruding from both sides of the structured web 21, as well as macro-patterns embossed into the web 21.

The number, spacing, and size of displaced fibers 6 can be varied by changing the number, spacing, and size of teeth 110 and making corresponding dimensional changes as necessary to roll 104 and/or roll 102. This variation, together with the variation possible in base substrate 20 and the variation in processing, such as line speeds, permits many varied structured webs 21 to be made for many purposes.

From the description of structured web 21, it can be seen that the broken fibers 8 of displaced fibers 6 can originate and extend from either the first surface 12 or the second surface 14 of structured substrate 21. Of course the broken fibers 8 of displaced fibers 6 can also extend from the interior 19 of structured substrate 21. As shown in FIG. 5, the broken fibers 8 of displaced fibers 6 extend due to having been urged out of the generally two-dimensional plane of base substrate 20 (i.e., urged in the "Z-direction" as shown in FIG. 3). In general, the broken fibers 8 or loose ends 18 of the second regions 4 comprise fibers that are integral with and extend from the fibers of the fibrous web first regions 2.

The extension of broken fibers 8 can be accompanied by a general reduction in fiber cross sectional dimension (e.g., diameter for round fibers) due to plastic deformation of the fibers and the effects of Poisson's ratio. Therefore, portions of the broken fibers 8 of displaced fibers 6 can have an average fiber diameter less than the average fiber diameter of the fibers of base substrate 20 as well as the fibers of first regions 2. It has been found that the reduction in fiber cross-sectional dimension is greatest intermediate the base 5 and the loose ends 3 of displaced fibers 6. This is believed to be due to portions of fibers at the base 5 and distal portion 3 of displaced fibers 6 are adjacent the tip of teeth 110 of roll 104, described more fully below, such that they are frictionally locked and immobile during processing. In the present invention the fiber cross section reduction is minimal due to the high fiber strength and low fiber elongation.

Figure 7:
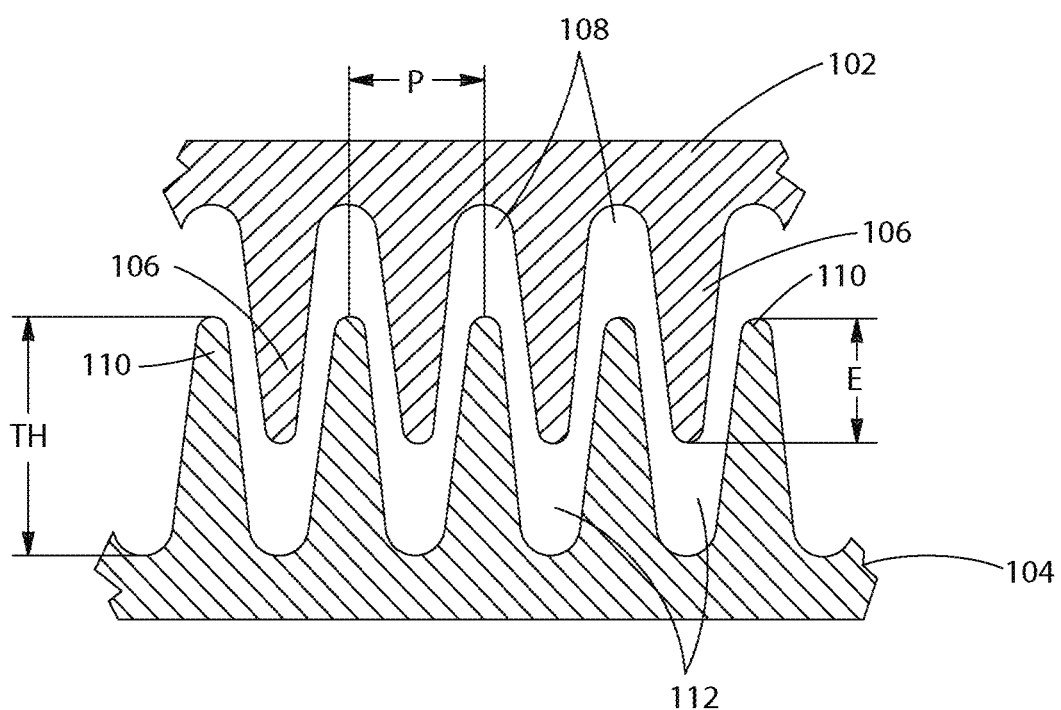
FIG. 7 is a cross-sectional depiction of a portion of the apparatus shown in FIG. 2.

FIG. 7 shows in cross section a portion of the intermeshing rolls 102 (and 102A and 102B, discussed below) and 104 including ridges 106 and teeth 110. As shown teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of base substrate 20 and the desired characteristics of structured substrate 1 of the present invention. For example, in general, to obtain broken fibers 8 in displaced fibers 6 requires a level of engagement E sufficient to elongate and plastically deform the displaced fibers to a point where the fibers break. Also, the greater the density of second regions 4 desired (second regions 4 per unit area of structured substrate 1), the smaller the pitch should be, and the smaller the tooth length TL and tooth distance TD should be, as described below.

Figure 8:
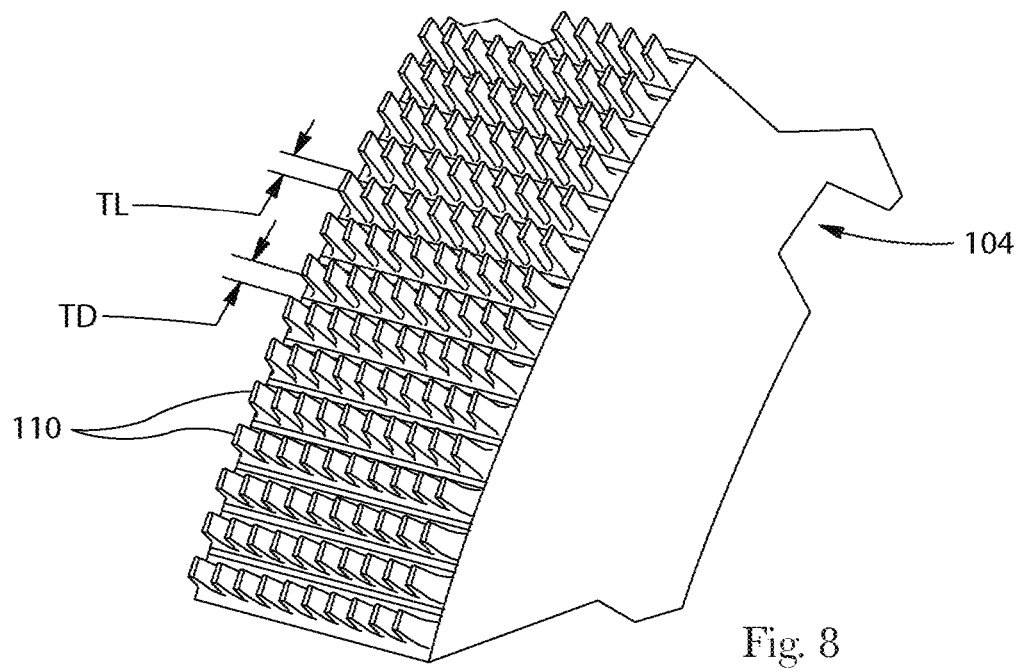
FIG. 8 is a perspective view of a portion of the apparatus for forming one embodiment the web of the present invention.
Figure 9:
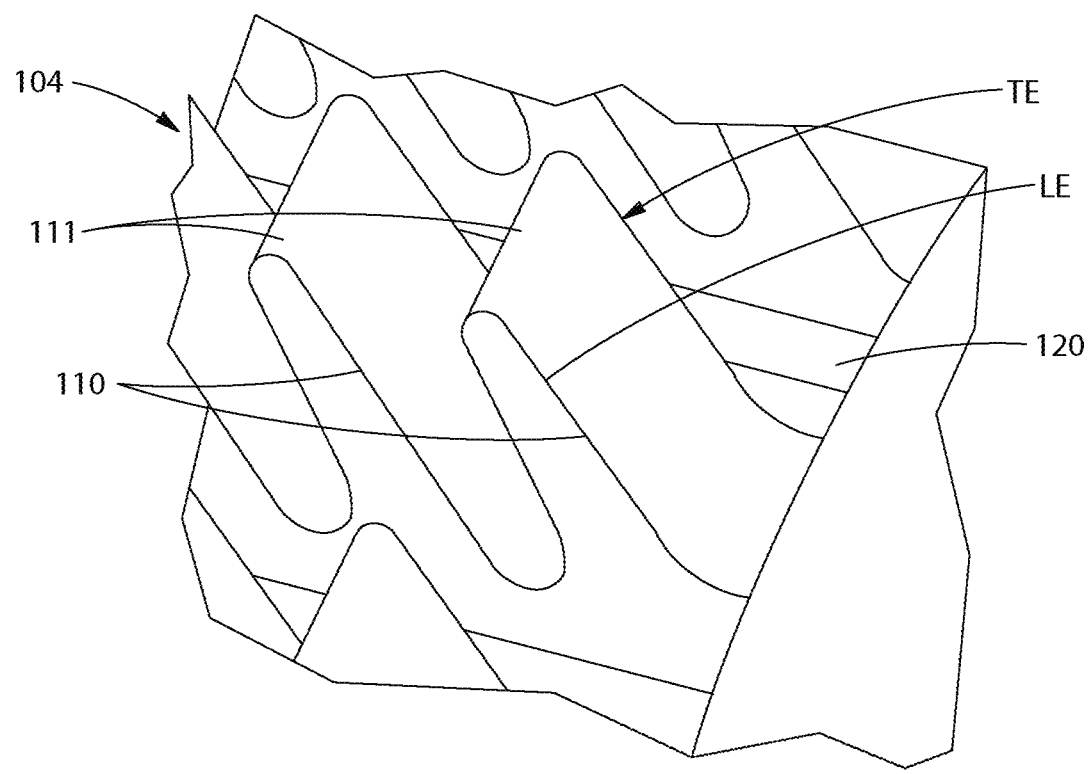
FIG. 9 is an enlarged perspective view of a portion of the apparatus for forming the web of the present invention.

FIG. 8 shows a portion of one embodiment of a roll 104 having a plurality of teeth 110 useful for making a structured substrate 21 or structured substrate 1 of spunbond nonwoven material from a spunbond nonwoven base substrate 20. An enlarged view of teeth 110 shown in FIG. 8 is shown in FIG. 9. In this view of roll 104, teeth 110 have a uniform circumferential length dimension TL of about 1.25 mm measured generally from the leading edge LE to the trailing edge TE at the tooth tip 111, and are uniformly spaced from one another circumferentially by a distance TD of about 1.5 mm. For making a fibrous structured substrate 1 from a base substrate 20, teeth 110 of roll 104 can have a length TL ranging from about 0.5 mm to about 3 mm and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH). Of course, E, P, TH, TD and TL can each be varied independently of each other to achieve a desired size, spacing, and area density of displaced fibers 6 (number of displaced fibers 6 per unit area of structured substrate 1).

As shown in FIG. 9, each tooth 110 has a tip 111, a leading edge LE and a trailing edge TE. The tooth tip 111 can be rounded to minimize fiber breakage and is preferably elongated and has a generally longitudinal orientation, corresponding to the longitudinal axes L of second regions 4. It is believed that to get the displaced fibers 6 of the structured substrate 1, the LE and TE should be very nearly orthogonal to the local peripheral surface 120 of roll 104. As well, the transition from the tip 111 and the LE or TE should be a relatively sharp angle, such as a right angle, having a sufficiently small radius of curvature such that, in use the teeth 110 push through base substrate 20 at the LE and TE. An alternative tooth tip 111 can be a flat surface to optimize bonding.

Referring back to FIG. 1, after displaced fibers 6 are formed, structured substrate 21 may travel on rotating roll 104 to nip 117 between roll 104 and a first bonding roll 156. Bonding roll 156 can facilitate a number of bonding techniques. For example, bonding roll 156 can be a heated steel roller for imparting thermal energy in nip 117, thereby melt-bonding adjacent fibers of structured web 21 at the distal ends (tips) of displaced fibers 6.

In a preferred embodiment, as discussed in the context of a preferred structured substrate below, bonding roll 156 is a heated roll designed to impart sufficient thermal energy to structured web 21 so as to thermally bond adjacent fibers of the distal ends of displaced fibers 6. Thermal bonding can be by melt-bonding adjacent fibers directly, or by melting an intermediate thermoplastic agent, such as polyethylene powder, which in turn, adheres adjacent fibers. Polyethylene powder can be added to base substrate 20 for such purposes.

First bonding roll 156 can be heated sufficiently to melt or partially melt fibers at the distal ends 3 of displaced fibers 6. The amount of heat or heat capacity necessary in first bonding roll 156 depends on the melt properties of the fibers of displaced fibers 6 and the speed of rotation of roll 104. The amount of heat necessary in first bonding roll 156 also depends on the pressure induced between first bonding roll 156 and tips of teeth 110 on roll 104, as well as the degree of melting desired at distal ends 3 of displaced fibers 6.

In one embodiment, first bonding roll 156 is a heated steel cylindrical roll, heated to have a surface temperature sufficient to melt-bond adjacent fibers of displaced fibers 6. First bonding roll 156 can be heated by internal electrical resistance heaters, by hot oil, or by any other means known in the art for making heated rolls. First bonding roll 156 can be driven by suitable motors and linkages as known in the art. Likewise, first bonding roll can be mounted on an adjustable support such that nip 117 can be accurately adjusted and set.

Figure 10:
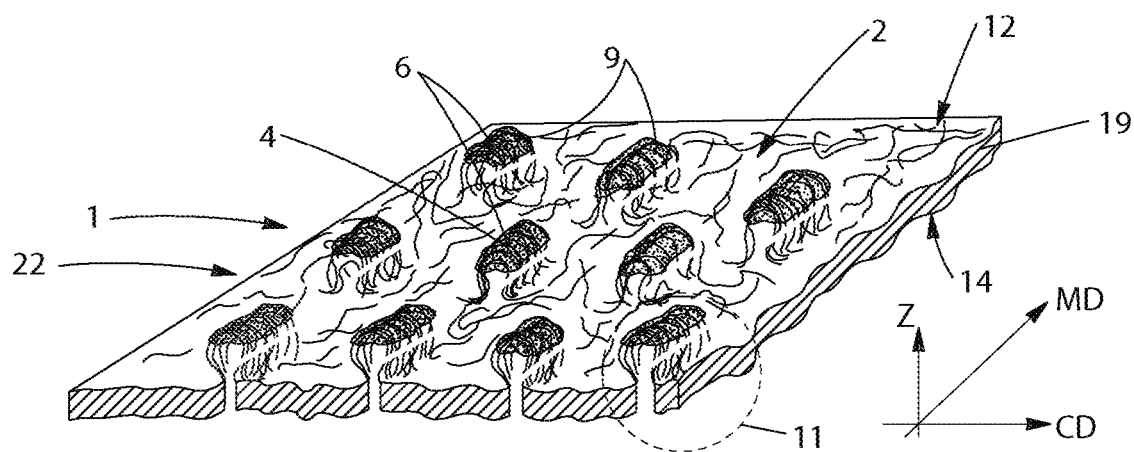
FIG. 10 is a partial perspective view of a structured substrate having melt-bonded portions of displaced fibers.
Figure 11:
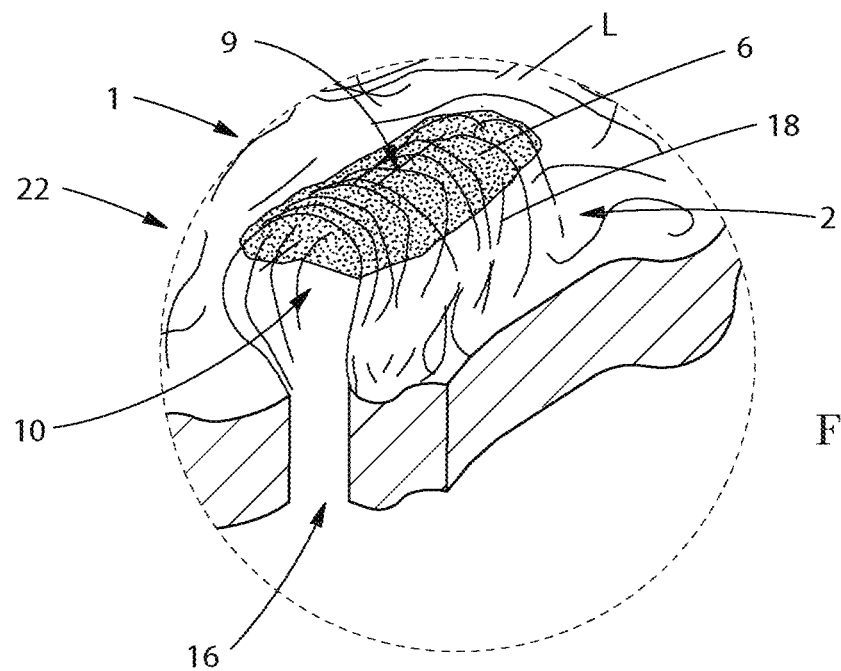
FIG. 11 is an enlarged portion of the structured substrate shown in FIG. 10.

FIG. 10 shows a portion of structured substrate 21 after being processed through nip 117 to be structured substrate 22, which, without further processing can be a structured substrate 21 of the present invention. Structured substrate 22 is similar to structured substrate 21 as described earlier, except that the distal ends 3 of displaced fibers 6 are bonded, and are preferably thermally melt-bonded such that adjacent fibers are at least partially bonded to form distally-disposed melt-bonded portions 9. After forming displaced fibers 6 by the process described above, the distal portions 3 of displaced fibers 6 can be heated to thermally join portions of fibers such that adjacent fiber portions are joined to one another to form displaced fibers 6 having melt-bonded portions 9, also referred to as "tip bonding".

The distally-disposed melt-bonded portions 9 can be made by application of thermal energy and pressure to the distal portions of displaced fibers 6. The size and mass of the distally-disposed melt-bonded portions 9 can be modified by modifying the amount of heat energy imparted to the distal portions of displaced fibers 6, the line speed of apparatus 150, and the method of heat application.

In another embodiment, distally-disposed melt-bonded portions 9 can be made by application of radiant heat. That is, in one embodiment bonding roll 156 can be replaced or supplemented by a radiant heat source, such that radiant heat can be directed toward structured substrate 21 at a sufficient distance and corresponding sufficient time to cause fiber portions in the distally-disposed portions of displaced fibers 6 to soften or melt. Radiant heat can be applied by any of known radiant heaters. In one embodiment, radiant heat can be provided by a resistance-heated wire disposed in relation to structured substrate 21 such that it is extended in the CD direction at a sufficiently-close, uniformly-spaced distance that as the web is moved in relation to the wire, radiant heat energy at least partially melts the distally-disposed portions of displaced fibers 6. In another embodiment, a heated flat iron, such as a hand-held iron for ironing clothes, can be held adjacent the distal ends 3 of displaced fibers 6, such that melting is effected by the iron.

The benefit of processing the structured substrate 22 as described above is that the distal ends 3 of displaced fibers 6 can be melted under a certain amount of pressure in nip 117 without compressing or flattening displaced fibers 6. As such, a three-dimensional web can be produced and set, or "locked in" to shape, so to speak by providing for thermal bonding after forming. Moreover, the distally-disposed bonded or melt-bonded portions 9 can aid in maintaining the lofty structure of displaced fibers 6 and aged caliper of the structured substrate when structured substrate 22 is subjected to compression or shearing forces. For example, a structured substrate 22 processed as disclosed above to have displaced fibers 6 comprising fibers integral with but extending from first region 2 and having distally-disposed melt-bonded portions 9 can have improved shape retention after compression due to winding onto a supply roll and subsequently unwinding. It is believed that by bonding together adjacent fibers at distal portions of displaced fibers 6, the fibers experience less random collapse upon compression; that is, the entire structure of displaced fibers 6 tends to move together, thereby permitting better shape retention upon a disordering event such as compression and/or shear forces associated with rubbing the surface of the web.

In an alternate embodiment described in reference to FIG. 1, substrate 20 is moved in the machine direction over roller 154 and to the nip 116 of the first set of counter-rotating intermeshing rolls 102A and 104 where the depth of engagement is between 0.01 inch and 0.15 inch such that partial fiber displacement occurs but there is little, if any, fiber breakage. The web then proceeds to nip 117 formed between roll 104 and bonding roll 156 where tips of the partial displaced fibers are bonded. After passing through nip 117, the structured substrate 22 proceeds to nip 118 formed between roll 104 and 102B where the depth of engagement is greater than the depth of engagement at nip 116 such that the displaced fibers are further displaced forming broken fibers. This process can result in a larger number of the displaced fibers 6 being joined by the melt-bonded portions 9.

Over Bonding

Over bonding refers to melt bonding performed on a substrate that has been previously undergone fiber displacement. Over bonding is an optional process step. The over bonding can be done in-line, or can alternatively, be done on a separate converting process.

Figure 12E:
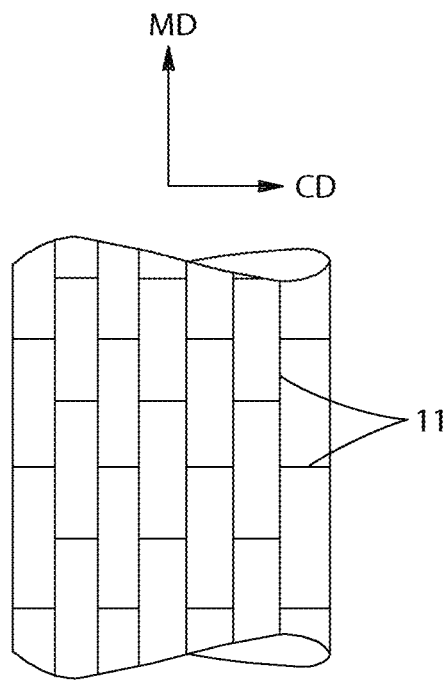
Figure 12F:
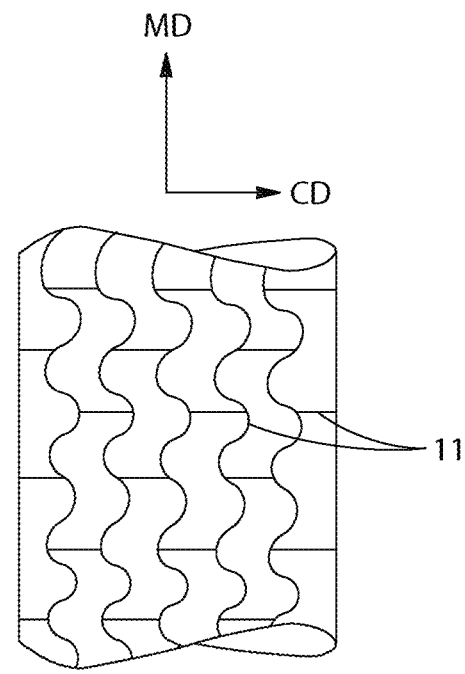

The over bonding relies upon heat and pressure to fuse the filaments together in a coherent pattern. A coherent pattern is defined as a pattern that is reproducible along the length of the structured substrate so that a repeat pattern can be observed. The over bonding is done through a pressurized roller nip in which at least one of the rolls is heated, preferably both rolls are heated. If the over bonding is done when the base substrate is already heated, then the pressurized roller nip would not need to be heated. Examples of patterns of over bond regions 11 are shown in FIGS. 12a through 12f, however, other over bond patterns are possible. FIG. 12a shows over bond regions 11 forming a continuous pattern in the machine direction. FIG. 12b shows continuous over bond regions 11 in both the machine and cross-directions so that a continuous network of over bonds 11 is formed. This type of system can be produced with a single-step over bonding roll or multiple roll bonding systems. FIG. 12c shows over bond regions 11 that are discontinuous in the machine direction. The MD over bond pattern shown in FIG. 12c could also include over bond regions 11 in the CD connecting the MD over bond lines in a continuous or non-continuous design. FIG. 12d shows over bond regions 11 forming a wave pattern in the MD. FIG. 12e shows over bond regions 11 forming a herringbone pattern while FIG. 12f shows a wavy herringbone pattern.

The over bond patterns do not need to be evenly distributed and can be contoured to suit a specific application. The total area affected by over bonding is less than 75% of the total area of the fibrous web, preferably less than 50%, more preferably less than 30% and most preferably less than 25%, but should be at least 3%.

Figure 13:
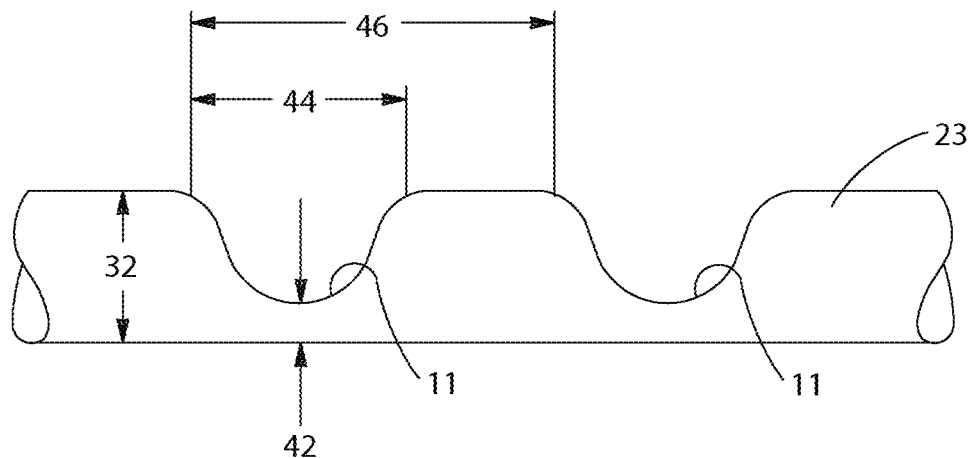
FIG. 13 is a cross-sectional view of a portion of the structured substrate showing bonded and/or over bond regions.

FIG. 13 illustrates the characteristics of over bonding. The over bonded region 11 has a thickness property relative to the first region thickness 32 of the base substrate 20 measured in-between the over bonded regions. The over bonded region 11 has a compressed thickness 42. The over bonded region has a characteristic width 44 on the structured substrate 21 and a spacing 46 between over bond regions.

The first region thickness 32 is preferably between 0.1 mm and 1.5 mm, more preferably between 0.15 mm and 1.3 mm, more preferably between 0.2 mm and 1.0 mm and most preferably between 0.25 mm and 0.7 mm. Over bonded region thickness 42 is preferably between 0.01 mm and 0.5 mm, more preferably between 0.02 mm and 0.25 mm, still more preferably between 0.03 mm and 0.1 mm and most preferably between 0.05 mm and 0.08 mm. The width 44 of the over-bonded region 11 is between 0.05 mm and 15 mm, more preferably between 0.075 mm and 10 mm, still more preferably between 0.1 mm and 7.5 mm and most preferably between 0.2 mm and 5 mm. The spacing 46 between over-bonded regions 11 is not required to be uniform in the structured substrate 21, but the extremes will fall within the range of 0.2 mm and 16 mm, preferably between 0.4 mm and 10 mm, more preferably between 0.8 mm and 7 mm and most preferably between 1 mm and 5.2 mm. Spacing 46, width 44 and thickness 42 of the over bonded regions 11 is based on the properties desired for the structured substrate 21 such as tensile strength and fluid handling properties.

Figure 14:
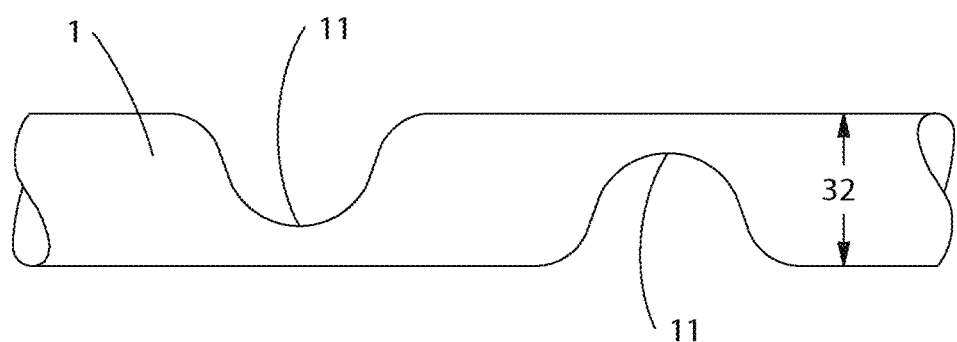
FIG. 14 is a cross-sectional view of a portion of the structured substrate showing bonded and/or over bond regions on opposing surfaces of the structured substrate.

FIG. 13 shows that the over bonds 11 having over bond thickness 42 can be created on one side of the structured substrate 21. FIG. 14 shows that the over bonds 11 can be on either side of the structured substrate 21 depending on the method used to make the structured substrate 21. Over bonds 11 on both sides 12, 14 of the structured substrate 21 may be desired to create tunnels when the structured substrate is combined with other nonwovens to further aid in the management of fluids. For instance, a double sided structured substrate may be used in a multi-layered high volume fluid acquisition system.

Over Bonding Process

Referring to the apparatus in FIG. 1, structured substrate 23 can have bonded portions that are not, or not only, at distally-disposed portions of displaced fibers 6. For example, by using a mating ridged roller instead of a flat, cylindrical roll for bonding roll 156 other portions of the structured substrate 23 such as at locations on the first surface 12 in the first regions 2 between the second regions 4 can be bonded. For instance, continuous lines of melt-bonded material could be made on first surface 12 between rows of displaced fibers 6. The continuous lines of melt-bonded material form over bonded regions 11 as previously described.

In general, while one first bonding roll 156 is illustrated, there may be more than one bonding roll at this stage of the process, such that bonding takes place in a series of nips 117 and/or involving different types of bonding rolls 156. Further, rather than being only a bonding roll, similar rolls can be provided to transfer various substances to base substrate 20 or structured web 21, such as various surface treatments to impart functional benefits. Any processes known in the art for such application of treatments can be utilized.

After passing through nip 117, structured substrate 22 proceeds to nip 118 formed between roll 104 and 102B, with roll 102B preferably being identical to roll 102A. The purpose of going around roll 102B is to remove structured substrate 22 from roll 104 without disturbing the displaced fibers 6 formed thereon. Because roll 102B intermeshes with roll 104 just as roll 102A did, displaced fibers 6 can fit into the grooves 108 of roll 102B as structured substrate 22 is wrapped around roll 102B. After passing through nip 118, structured substrate 22 can be taken up on a supply roll for further processing as structured substrate 23 of the present invention. However, in the embodiment shown in FIG. 1, structured substrate 22 is processed through nip 119 between roll 102B and second bonding roll 158. Second bonding roll 158 can be identical in design to first bonding roll 156. Second bonding roll 158 can provide sufficient heat to at least partially melt a portion of the second surface 14 of structured substrate 22 to form a plurality of non-intersecting, substantially continuous over bond regions 11 corresponding to the nip pressures between the tips of ridges 106 of roll 102B and the generally flat, smooth surface of roll 158.

Second bonding roll 158 can be used as the only bonding step in the process (i.e., without first having structured substrate 22 formed by bonding the distal ends of displaced fibers 6). In such a case structured web 22 would be a structured web 23 with bonded portions on the second side 14 thereof. However, in general, structured web 23 is preferably a double over bonded structured web 22 having bonded distal ends of displaced fibers 6 (tip bonding) and a plurality of non-intersecting, substantially continuous melt-bonded regions on first side 12 or second side 14 thereon.

Finally, after structured substrate 23 is formed, it can be taken up on a supply roll 160 for storage and further processing as a component in other products.

Figure 1A:
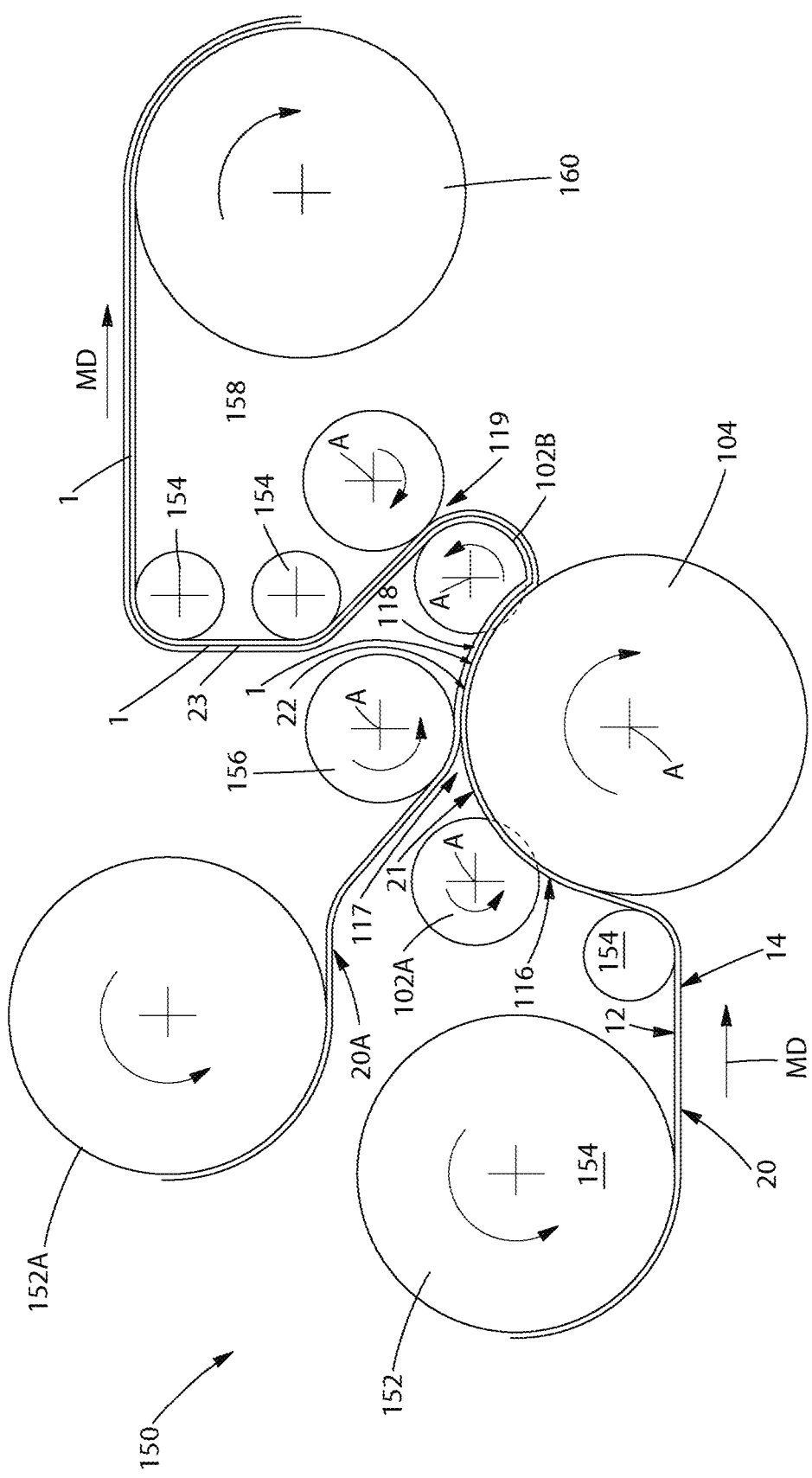
FIG. 1A is a schematic representation of an alternate apparatus for making a laminate web according to the present invention.

In an alternate embodiment a second substrate 21A can be added to the structured substrate 21 using the process shown in FIG. 1A. The second substrate 21A can be a film, a nonwoven or a second base substrate as previously described. For this embodiment, base substrate 20 is moved in the machine direction over roller 154 and to the nip 116 of the first set of counter-rotating intermeshing rolls 102A and 104 where the fibers are fully displaced forming broken fibers. The web then proceeds to nip 117 formed between roll 104 and bonding roll 156 where second substrate 21A is introduced and bonded to the distal portions 3 of the displaced fibers 6. After passing through nip 117, the structured substrate 22 proceeds to nip 118 formed between rolls 104 and 102B where the depth of engagement is zero such that rolls 104 and 102B are not engaged, or the depth of engagement is less than the depth of engagement formed at nip 116 between rolls 102A and 104 such that the no additional fiber displacement occurs in the structured substrate. Alternatively, for this embodiment, the depth of engagement at nip 118 can be set such that deformation occurs in the second substrate 21A but no additional fiber displacement occurs in the structured substrate 22. In other words, the depth of engagement at nip 118 is still less than the depth of engagement at nip 116.

Materials

The composition used to form fibers for the base substrate of the present invention can include thermoplastic polymeric and non-thermoplastic polymeric materials. The thermoplastic polymeric material must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol, preferably from about 5,000 g/mol to about 750,000 g/mol, more preferably from about 10,000 g/mol to about 500,000 g/mol and even more preferably from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Other suitable polymeric materials include ethylene acrylic acid, polyolefin carboxylic acid copolymers, and combinations thereof. The polymers described in US publications U.S. Pat. No. 6,746,766, U.S. Pat. No. 6,818,295, U.S. Pat. No. 6,946,506 and US application 03/0092343. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins.

Nonlimiting examples of thermoplastic polymers suitable for use in the present invention include aliphatic polyesteramides; aliphatic polyesters; aromatic polyesters including polyethylene terephthalates (PET) and copolymer (coPET), polybutylene terephthalates and copolymers; polytrimethylene terephthalates and copolymers; polypropylene terephthalates and copolymers; polypropylene and propylene copolymers; polyethylene and polyethylene copolymers; aliphatic/aromatic copolyesters; polycaprolactones; poly(hydroxyalkanoates) including poly(hydroxybutyrate-co-hydroxyvalerate), poly(hydroxybutyrate-co-hexanoate), or other higher poly(hydroxybutyrate-co-alkanoates) as referenced in U.S. Pat. No. 5,498,692 to Noda, herein incorporated by reference; polyesters and polyurethanes derived from aliphatic polyols (i.e., dialkanoyl polymers); polyamides; polyethylene/vinyl alcohol copolymers; lactic acid polymers including lactic acid homopolymers and lactic acid copolymers; lactide polymers including lactide homopolymers and lactide copolymers; glycolide polymers including glycolide homopolymers and glycolide copolymers; and mixtures thereof. Preferred are aliphatic polyesteramides, aliphatic polyesters, aliphatic/aromatic copolyesters, lactic acid polymers, and lactide polymers.

Suitable lactic acid and lactide polymers include those homopolymers and copolymers of lactic acid and/or lactide which have a weight average molecular weight generally ranging from about 10,000 g/mol to about 600,000 g/mol, preferably from about 30,000 g/mol to about 400,000 g/mol, more preferably from about 50,000 g/mol to about 200,000 g/mol. An example of commercially available polylactic acid polymers includes a variety of polylactic acids that are available from the Chronopol Incorporation located in Golden, Colo., and the polylactides sold under the tradename Eco-PLA®. Examples of suitable commercially available polylactic acid are NATUREWORKS from Cargill Dow and LACEA from Mitsui Chemical. Preferred is a homopolymer or copolymer of poly lactic acid having a melting temperature from about 160° to about 175° C. Modified poly lactic acid and different stereo configurations may also be used, such as poly L-lactic acid and poly D,L-lactic acid with D-isomer levels up to 75%. Optional racemic combinations of D and L isomers to produce high melting temperature PLA polymers are also preferred. These high melting temperature PL polymers are special PLA copolymers (with the understanding that the D-isomer and L-isomer are treated as different stereo monomers) with melting temperatures above 180° C. These high melting temperatures are achieved by special control of the crystallite dimensions to increase the average melting temperature.

Depending upon the specific polymer used, the process, and the final use of the fiber, more than one polymer may be desired. The polymers of the present invention are present in an amount to improve the mechanical properties of the fiber, the opacity of the fiber, optimize the fluid interaction with the fiber, improve the processability of the melt, and improve attenuation of the fiber. The selection and amount of the polymer will also determine if the fiber is thermally bondable and affect the softness and texture of the final product. The fibers of the present invention may comprise a single polymer, a blend of polymers, or be multicomponent fibers comprising more than one polymer. The fibers in the present invention are thermally bondable.

Multiconstituent blends may be desired. For example, blends of polyethylene and polypropylene (referred to hereafter as polymer alloys) can be mixed and spun using this technique. Another example would be blends of polyesters with different viscosities or monomer content. Multicomponent fibers can also be produced that contain differentiable chemical species in each component. Non-limiting examples would include a mixture of 25 melt flow rate (MFR) polypropylene with 50 MFR polypropylene and 25 MFR homopolymer polypropylene with 25 MFR copolymer of polypropylene with ethylene as a comonomer.

The more preferred polymeric materials have melting temperatures above 110° C., more preferably above 130° C., even more preferably above 145° C., still more preferably above 160° C. and most preferably above 200° C. A still further preference for the present invention is polymers with high glass transition temperatures. Glass transition temperatures above −10° C. in the end-use fiber form are preferred, more preferably above 0° C., still more preferably above 20° C. and most preferably above 50° C. This combination of properties produces fibers that are stable at elevated temperatures. Exemplary examples of materials of this type are polypropylene, polylactic acid based polymers, and polyester terephthalate (PET) based polymer systems.

Optional Materials

Optionally, other ingredients may be incorporated into the spinnable composition used to form fibers for the base substrate. The optional materials may be used to modify the processability and/or to modify physical properties such as opacity, elasticity, tensile strength, wet strength, and modulus of the final product. Other benefits include, but are not limited to, stability, including oxidative stability, brightness, color, flexibility, resiliency, workability, processing aids, viscosity modifiers, and odor control. Examples of optional materials include, but are not limited to, titanium dioxide, calcium carbonate, colored pigments, and combinations thereof. Further additives including, but not limited to, inorganic fillers such as the oxides of magnesium, aluminum, silicon, and titanium may be added as inexpensive fillers or processing aides. Other suitable inorganic materials include, but are not limited to, hydrous magnesium silicate, titanium dioxide, calcium carbonate, clay, chalk, boron nitride, limestone, diatomaceous earth, mica glass quartz, and ceramics. Additionally, inorganic salts, including, but not limited to, alkali metal salts, alkaline earth metal salts and phosphate salts may be used.

Optionally, other ingredients may be incorporated into the composition. These optional ingredients may be present in quantities of less than about 50%, preferably from about 0.1% to about 20%, and more preferably from about 0.1% to about 12% by weight of the composition. The optional materials may be used to modify the processability and/or to modify physical properties such as elasticity, tensile strength and modulus of the final product. Other benefits include, but are not limited to, stability including oxidative stability, brightness, flexibility, color, resiliency, workability, processing aids, viscosity modifiers, biodegradability, and odor control. Nonlimiting examples include salts, slip agents, crystallization accelerators or retarders, odor masking agents, cross-linking agents, emulsifiers, surfactants, cyclodextrins, lubricants, other processing aids, optical brighteners, antioxidants, flame retardants, dyes, pigments, fillers, proteins and their alkali salts, waxes, tackifying resins, extenders, and mixtures thereof. Slip agents may be used to help reduce the tackiness or coefficient of friction in the fiber. Also, slip agents may be used to improve fiber stability, particularly in high humidity or temperatures. A suitable slip agent is polyethylene. Thermoplastic starch (TPS) may also be added to the polymeric composition. Especially important are polymer additives used to reduce static electricity build-up in the production and use of polyester thermoplastic materials, particularly PET. Such preferred materials are acetaldehyde acid scavengers, ethoxylated sorbitol esters, glycerol esters, alkyl sulphonate, combinations and mixtures thereof and derivative compounded.

Further additives including inorganic fillers such as the oxides of magnesium, aluminum, silicon, and titanium may be added as inexpensive fillers or processing aides. Other inorganic materials include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, may be used as processing aides. Other optional materials that modify the water responsiveness of the thermoplastic starch blend fiber are stearate based salts, such as sodium, magnesium, calcium, and other stearates, as well as rosin component, such as gum rosin.

Hydrophilic agents can be added to the polymeric composition. The hydrophilic agents can be added in standard methods known to those skilled in the art. The hydrophilic agents can be low molecular weight polymeric materials or compounds. The hydrophilic agent can also be a polymeric material with higher molecular weight. The hydrophilic agent can be present in an amount from 0.01 wt % to 90 wt %, with preferred range of 0.1 wt % to 50 wt % and a still more preferred range of 0.5 wt % to 10 wt %. The hydrophilic agent can be added when the initial resin is produced at the resin manufacturer, or added as masterbatch in the extruder when the fibers are made. Preferred agents are polyester polyether, polyester polyether copolymers and nonionic polyester compounds for polyester bases polymers. Ethoxylated low and high molecular weight polyolefinic compounds can also be added. Compatibilizing agents can be added to these materials to aid in better processing for these materials, and to make for a more uniform and homogenous polymeric compound. One skilled in the art would understand that using compatibilizing agents can be added in a compounding step to produce polymer alloys with melt additives not inherently effective with the base polymer. For example, a base polypropylene resin can be combined with a hydrophilic polyester polyether copolymer through the use of maleated polypropylene as a compatibilizer agent.

Fibers

The fibers forming the base substrate in the present invention may be monocomponent or multicomponent. The term "fiber" is defined as a solidified polymer shape with a length to thickness ratio of greater than 1,000. The monocomponent fibers of the present invention may also be multiconstituent. Constituent, as used herein, is defined as meaning the chemical species of matter or the material. Multiconstituent fiber, as used herein, is defined to mean a fiber containing more than one chemical species or material. Multiconstituent and alloyed polymers have the same meaning in the present invention and can be used interchangeably. Generally, fibers may be of monocomponent or multicomponent types. Component, as used herein, is defined as a separate part of the fiber that has a spatial relationship to another part of the fiber. The term multicomponent, as used herein, is defined as a fiber having more than one separate part in spatial relationship to one another. The term multicomponent includes bicomponent, which is defined as a fiber having two separate parts in a spatial relationship to one another. The different components of multicomponent fibers are arranged in substantially distinct regions across the cross-section of the fiber and extend continuously along the length of the fiber. Methods for making multicomponent fibers are well known in the art. Multicomponent fiber extrusion was well known in the 1960's. DuPont was a lead technology developer of multicomponent capability, with U.S. Pat. No. 3,244,785 and U.S. Pat. No. 3,704,971 providing a technology description of the technology used to make these fibers. "Bicomponent Fibers" by R. Jeffries from Merrow Publishing in 1971 laid a solid groundwork for bicomponent technology. More recent publications include "Taylor-Made Polypropylene and Bicomponent Fibers for the Nonwoven Industry," Tappi Journal December 1991 (p 103) and "Advanced Fiber Spinning Technology" edited by Nakajima from Woodhead Publishing.

The nonwoven fabric formed in the present invention may contain multiple types of monocomponent fibers that are delivered from different extrusion systems through the same spinneret. The extrusion system, in this example, is a multicomponent extrusion system that delivers different polymers to separate capillaries. For instance, one extrusion system would deliver polyester terephthalate and the other a polyester terephthalate copolymer such that the copolymer composition melts at a different temperatures. In a second example, one extrusion system might deliver a polyester terephthalate resin and the other polypropylene. In a third example, one extrusion system might deliver a polyester terephthalate resin and the other an additional polyester terephthalate resin that has a molecular weight different from the first polyester terephthalate resin. The polymer ratios in this system can range from 95:5 to 5:95, preferably from 90:10 to 10:90 and 80:20 to 20:80.

Bicomponent and multicomponent fibers may be in a side-by-side, sheath-core, segmented pie, ribbon, islands-in-the-sea configuration, or any combination thereof The sheath may be continuous or non-continuous around the core. Non-inclusive examples of exemplarily multicomponent fibers are disclosed in U.S. Pat. No. 6,746,766. The ratio of the weight of the sheath to the core is from about 5:95 to about 95:5. The fibers of the present invention may have different geometries that include, but are not limited to; round, elliptical, star shaped, trilobal, multilobal with 3-8 lobes, rectangular, H-shaped, C-shaped, I-shape, U-shaped and other various eccentricities. Hollow fibers can also be used. Preferred shapes are round, trilobal and H-shaped. The round and trilobal fiber shapes can also be hollow.

A "highly attenuated fiber" is defined as a fiber having a high draw down ratio. The total fiber draw down ratio is defined as the ratio of the fiber at its maximum diameter (which is typically results immediately after exiting the capillary) to the final fiber diameter in its end use. The total fiber draw down ratio will be greater than 1.5, preferable greater than 5, more preferably greater than 10, and most preferably greater than 12. This is necessary to achieve the tactile properties and useful mechanical properties.

The fiber "diameter" of the shaped fiber of the present invention is defined as the diameter of a circle which circumscribes the outer perimeter of the fiber. For a hollow fiber, the diameter is not of the hollow region but of the outer edge of the solid region. For a non-round fiber, fibers diameters are measured using a circle circumscribed around the outermost points of the lobes or edges of the non-round fiber. This circumscribed circle diameter may be referred to as that fiber's effective diameter. Preferably, the highly attenuated multicomponent fiber will have an effective fiber diameter of less than 500 micrometers. More preferably the effective fiber diameter will be 250 micrometer or less, even more preferably 100 micrometers or less, and most preferably less than 50 micrometers. Fibers commonly used to make nonwovens will have an effective fiber diameter of from about 5 micrometers to about 30 micrometers. Fibers in the present invention tend to be larger than those found in typical spunbond nonwovens. As such fibers with effective diameters less than 10 micrometers are not of use. Fibers useful in the present invention have an effective diameter greater than about 10 microns, more preferably greater than 15 micrometers, and most preferably greater than 20 micrometers. Fiber diameter is controlled by spinning speed, mass through-put, and blend composition. When the fibers in the present invention are made into a discrete layer, that layer can be combined with additional layers that may contain small fibers, even nano-dimension fibers.

The term spunlaid diameter refers to fibers having an effective diameter greater than about 12.5 micrometers up to 50 micrometers. This diameter range is produced by most standard spunlaid equipment. Micrometers and micron ($\mu$m) mean the same thing and can be used interchangeably. Meltblown diameters are smaller than spunlaid diameters. Typically, meltblown diameters are from about 0.5 to about 12.5 micrometers. Preferable meltblown diameters range from about 1 to about 10 micrometers.

Because the diameter of shaped fibers can be hard to determine, the denier of the fiber is often referenced. Denier is defined as the mass of a fiber in grams at 9000 linear meters of length, expressed as dpf (denier per filament). Thus, the inherent density of the fiber is also factored in when converting from diameter to denier and visa versa. For the present invention, the preferred denier range is greater than 1 dpf and less than 100 dpf. A more preferred denier range is 1.5 dpf to 50 dpf and a still more preferred range from 2.0 dpf to 20 dpf, and a most preferred range of 4 dpf to 10 dpf. An example of the denier to diameter relationship for polypropylene is a 1 dpf fiber of polypropylene that is solid round with a density of about 0.900 g/cm$^3$ has a diameter of about 12.55 micrometers.

For the present invention, it is desirable for the fibers to have limited extensibility and exhibit a stiffness to withstand compressive forces. The fibers of the present invention will have individual fiber breaking loads of greater than 5 grams per filament. Tensile properties of fibers are measured following a procedure generally described by ASTM standard D 3822-91 or an equivalent test, but the actual test that was used is fully described below. The tensile modulus (initial modulus as specified in ASTM standard D 3822-91 unless otherwise specified) should be greater than 0.5 GPa (giga pascals), more preferably greater than 1.5 GPa, still more preferably more than 2.0 GPa and most preferably greater than 3.0 GPa. The higher tensile modulus will produce stiffer fibers that provide a sustainable specific volume. Examples will be provided below.

The hydrophilicity and hydrophobicity of the fibers can be adjusted in the present invention. The base resin properties can have hydrophilic properties via copolymerization (such as the case for certain polyesters (EASTONE from Eastman Chemical, the sulfopolyester family of polymers in general) or polyolefins such as polypropylene or polyethylene) or have materials added to the base resin to render it hydrophilic. Exemplarily examples of additives include CIBA Irgasurf® family of additives. The fibers in the present invention can also be treated or coated after they are made to render them hydrophilic. In the present invention, durable hydrophilicity is preferred. Durable hydrophilicity is defined as maintaining hydrophilic characteristics after more than one fluid interaction. For example, if the sample being evaluated is tested for durable hydrophilicity, water can be poured on the sample and wetting observed. If the sample wets out it is initially hydrophilic. The sample is then completely rinsed with water and dried. The rinsing is best done by putting the sample in a large container and agitating for ten seconds and then drying. The sample after drying should also wet out when contacted again with water.

The fibers of the present invention are thermally stable. Fiber thermal stability is defined as having less than 30% shrinkage in boiling water, more preferably less than 20% shrinkage and most preferably less than 10% shrinkage. Some fibers in the present invention will have shrinkage less than 5%. The shrinkage is determined by measuring the fiber length before and after being placed in boiling water for one minute. Highly attenuated fibers would enable production of thermally stable fibers.

The fiber shapes used in the base substrate in the present invention may consist of solid round, hollow round and various multi-lobal shaped fibers, among other shapes. A mixture of shaped fibers having cross-sectional shapes that are distinct from one another is defined to be at least two fibers having cross-sectional shapes that are different enough to be distinguished when examining a cross-sectional view with a scanning electron microscope. For example, two fibers could be trilobal shape but one trilobal having long legs and the other trilobal having short legs. Although not preferred, the shaped fibers could be distinct if one fiber is hollow and another solid even if the overall cross-sectional shape is the same.

The multi-lobal shaped fibers may be solid or hollow. The multi-lobal fibers are defined as having more than one inflection point along the outer surface of the fiber. An inflection point is defined as being a change in the absolute value of the slope of a line drawn perpendicular to the surface of fiber when the fiber is cut perpendicular to the fiber axis. Shaped fibers also include crescent shaped, oval shaped, square shaped, diamond shaped, or other suitable shapes.

Solid round fibers have been known to the synthetic fiber industry for many years. These fibers have a substantially optically continuous distribution of matter across the width of the fiber cross section. These fibers may contain micro voids or internal fibrillation but are recognized as being substantially continuous. There are no inflection points for the exterior surface of solid round fibers.

The hollow fibers of the present invention, either round or multi-lobal shaped, will have a hollow region. A solid region of the hollow fiber surrounds the hollow region. The perimeter of the hollow region is also the inside perimeter of the solid region. The hollow region may be the same shape as the hollow fiber or the shape of the hollow region can be non-circular or non-concentric. There may be more than one hollow region in a fiber.

The hollow region is defined as the part of the fiber that does not contain any material. It may also be described as the void area or empty space. The hollow region will comprise from about 2% to about 60% of the fiber. Preferably, the hollow region will comprise from about 5% to about 40% of the fiber. More preferably, the hollow region comprises from about 5% to about 30% of the fiber and most preferably from about 10% to about 30% of the fiber. The percentages are given for a cross sectional region of the hollow fiber (i.e., two dimensional).

The percent of hollow region must be controlled for the present invention. The percent hollow region is preferably greater than 2% or the benefit of the hollow region is not significant. However, the hollow region is preferably less than 60% or the fiber may collapse. The desired percent hollow depends upon the materials used, the end use of the fiber, and other fiber characteristics and uses.

The average fiber diameter of two or more shaped fibers having cross-sectional shapes that are distinct from on another is calculated by measuring each fiber type's average denier, converting the denier of each shaped fiber into the equivalent solid round fiber diameter, adding the average diameters together of each shaped fiber weighted by their percent total fiber content, and dividing by the total number of fiber types (different shaped fibers). The average fiber denier is also calculated by converting the average fiber diameter (or equivalent solid round fiber diameter) through the relationship of the fiber density. A fiber is considered having a different diameter if the average diameter is at least about 10% higher or lower. The two or more shaped fibers having cross-sectional shapes that are distinct from one another may have the same diameter or different diameters. Additionally, the shaped fibers may have the same denier or different denier. In some embodiments, the shaped fibers will have different diameters and the same denier.

Multi-lobal fibers include, but are not limited to, the most commonly encountered versions such as trilobal and delta shaped. Other suitable shapes of multi-lobal fibers include triangular, square, star, or elliptical. These fibers are most accurately described as having at least one slope inflection point. A slope inflection point is defined as the point along the perimeter of the surface of a fiber where the slope of the fiber changes. For example, a delta shaped trilobal fiber would have three slope inflection points and a pronounced trilobal fiber would have six slope inflection points. Multilobal fibers in the present invention will generally have less than about 50 slope inflection points, and most preferably less than about 20 slope inflection points. The multi-lobal fibers can generally be described as non-circular, and may be either solid or hollow.

The mono and multiconstituent fibers of the present invention may be in many different configurations. Constituent, as used herein, is defined as meaning the chemical species of matter or the material. Fibers may be of monocomponent in configuration. Component, as used herein, is defined as a separate part of the fiber that has a spatial relationship to another part of the fiber.

After the fiber is formed, the fiber may further be treated or the bonded fabric can be treated. A hydrophilic or hydrophobic finish can be added to adjust the surface energy and chemical nature of the fabric. For example, fibers that are hydrophobic may be treated with wetting agents to facilitate absorption of aqueous liquids. A bonded fabric can also be treated with a topical solution containing surfactants, pigments, slip agents, salt, or other materials to further adjust the surface properties of the fiber.

The fibers in the present invention can be crimped, although it is preferred that they are not crimped. Crimped fibers are generally produced in two methods. The first method is mechanical deformation of the fiber after it is already spun. Fibers are melt spun, drawn down to the final filament diameter and mechanically treated, generally through gears or a stuffer box that imparts either a two dimensional or three dimensional crimp. This method is used in producing most carded staple fibers; however, carded staple fiber fabrics are not preferred because the fibers are not continuous and the fabrics produced from crimped fibers are generally very lofty before the fiber deformation technology is used. The second method for crimping fibers is to extrude multicomponent fibers that are capable of crimping in a spunlaid process. One of ordinary skill in the art would recognize that a number of methods of making bicomponent crimped spunbond fibers exists; however, for the present invention, three main techniques are considered for making crimped spunlaid nonwovens. The first is crimping that occurs in the spinline due to differential polymer crystallization in the spinline, a result of differences in polymer type, polymer molecular weight characteristics (e.g., molecular weight distribution) or additives content. A second method is differential shrinkage of the fibers after they have been spun into a spunlaid substrate. For instance, heating the spunlaid web can cause fibers to shrink due to differences in crystallinity in the as-spun fibers, for example during the thermal bonding process. A third method of causing crimping is to mechanically stretch the fibers or spunlaid web (generally for mechanical stretching the web has been bonded together). The mechanical stretching can expose differences in the stress-strain curve between the two polymer components, which can cause crimping.

The last two methods are commonly called latent crimping processes because they have to be activated after the fibers are spun. In the present invention, there is an order of preference for use of crimped fibers. Carded staple fiber fabrics can be used, so long as they have a base substrate thickness of less than 1.3 mm. Spunlaid or spunbond fabrics are preferred because they contain continuous filaments, which can be crimped, as long as the base substrate thickness or caliper is less than 1.3 mm. For the present invention, the base substrate contains less than 100 wt % crimped fibers, preferably less than 50 wt % crimped fibers, more preferably less than 20 wt % crimped fibers, more preferably less than 10 wt % and most preferably 0 wt % crimped fibers. Uncrimped fibers are preferred because the crimping process can reduce the amount of fluids transferred on the surface of the fibers and also the crimping can reduce the inherent capillarity of the base substrate by decreasing the specific density of the base substrate.

Short length fibers are defined as fibers having a length of less than 50 mm. In the present invention, continuous fibers are preferred over short cut fibers as they provide two additional benefits. The first benefit is that fluids can be transferred greater distances without fiber ends, thus providing enhanced capillarity. The second benefit is that continuous fibers produce base substrates with higher tensile strengths and stiffness, because the bonded network has continuous matrix of fibers that collectively are more inter-connected than one composed of short length fibers. It is preferred that the base substrate of the present invention contain very few short length fibers, preferably less than 50 wt % short length fibers, more preferably less than 20 wt % short length fibers, more preferably less than 10 wt % and most preferably 0 wt % short length fibers.

The fibers produced for the base substrate in the present invention are preferably thermally bondable. Thermally bondable in the present invention is defined as fibers that soften when they are raised near or above their peak melting temperature and that stick or fuse together under the influence of at least low applied pressures. For thermal bonding, the total fiber thermoplastic content should be more than 30 wt %, preferably more than 50 wt %, still more preferably more than 70 wt % and most preferably more than 90 wt %.

Spunlaid Process

The fibers forming the base substrate in the present invention are preferably continuous filaments forming spunlaid fabrics. Spunlaid fabrics are defined as unbonded fabrics having basically no cohesive tensile properties formed from essentially continuous filaments. Continuous filaments are defined as fibers with high length to diameter ratios, with a ratio of more than 10,000:1. Continuous filaments in the present invention that compose the spunlaid fabric are not staple fibers, short cut fibers or other intentionally made short length fibers. The continuous filaments in the present invention are on average, more than 100 mm long, preferably more than 200 mm long. The continuous filaments in the present invention are also not crimped, intentionally or unintentionally.

The spunlaid processes in the present invention are made using a high speed spinning process as disclosed in U.S. Pat. Nos. 3,802,817; 5,545,371; 6,548,431 and 5,885,909. In these melt spinning processes, extruders supply molten polymer to melt pumps, which deliver specific volumes of molten polymer that transfer through a spinpack, composed of a multiplicity of capillaries formed into fibers, where the fibers are cooled through an air quenching zone and are pneumatically drawn down to reduce their size into highly attenuated fibers to increase fiber strength through molecular level fiber orientation. The drawn fibers are then deposited onto a porous belt, often referred to as a forming belt or forming table.

The spunlaid process in the present invention used to make the continuous filaments will contain 100 to 10,000 capillaries per meter, preferably 200 to 7,000 capillaries per meter, more preferably 500 to 5,000 capillaries per meter, and still more preferably 1,000 to 3,000 capillaries per meter. The polymer mass flow rate per capillary in the present invention will be greater than 0.3 GHM (grams per hole per minute). The preferred range is from 0.4 GHM to 15 GHM, preferably between 0.6 GHM and 10 GHM, still more preferred between 0.8 GHM and 5 GHM and the most preferred range from 1 GHM to 4 GHM.

The spunlaid process in the present invention contains a single process step for making the highly attenuated, uncrimped continuous filaments. Extruded filaments are drawn through a zone of quench air where they are cooled and solidified as they are attenuated. Such spunlaid processes are disclosed in U.S. Pat. No. 3,338,992, U.S. Pat. No. 3,802,817, U.S. Pat. No. 4,233,014 U.S. Pat. No. 5,688,468, U.S. Pat. No. 6,548,431B1, U.S. Pat. No. 6,908,292B2 and US Application 2007/0057414A1. The technology described in EP 1340843B1 and EP 1323852B1 can also be used to produce the spunlaid nonwovens. The highly attenuated continuous filaments are directly drawn down from the exit of the polymer from the spinneret to the attenuation device, wherein the continuous filament diameter or denier does not change substantially as the spunlaid fabric is formed on the forming table. A preferred spunlaid process in the current invention includes a drawing device that pneumatically draws the fibers between the spinneret exits to the pneumatic drawing device enabling fibers to lay down onto the forming belt. The process differs from other spunlaid processes that mechanically draw the fibers from the spinneret.

The spunlaid process for the present invention produces, in a single step; thermally stable, continuous, uncrimped fibers that have a defined inherent tensile strength, fiber diameter or denier as disclosed earlier. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Still other suitable polymeric materials include ethylene acrylic acid, polyolefin carboxylic acid copolymers, and combinations thereof. The polymers described in U.S. Pat. No. 6,746,766, U.S. Pat. No. 6,818,295, U.S. Pat. No. 6,946,506 and US Published Application 03/0092343. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins. Exemplary polyester terephthalate (here after referred to as polyester unless stated otherwise) resins are Eastman F61HC (IV=0.61 dl/g), Eastman 9663 (IV=0.80 dl/g), DuPont Crystar 4415 (IV=0.61 gl/g). A suitable copolyester is Eastman 9921 (IV-0.81). The polyester intrinsic viscosity (IV) range suitable for the present invention ranges from 0.3 dl/g to 0.9 dl/g, preferably from 0.45 dl/g to 0.85 dl/g and more preferably from 0.55 dl/g to 0.82 dl/g. Intrinsic viscosity is a measure of polymer molecular weight and is well known to those skilled in polymer art. Polyester fibers in the present invention may be alloys, monocomponent and shaped. A preferred embodiment is polyester fibers that are multilobal, preferably trilobal, that are produced from a 0.61 dl/g resin with a denier between 3 dpf and 8 dpf. Although PET is most commonly referenced in this invention, other polyester terephthalate polymers can be used, such as PBT, PTT, PCT.

It has been unexpectedly discovered that a specific combination of resin properties can be used in a spunbond process to produce a thermally bonded PET nonwoven at high denier. Eastman F61HC PET polymer and Eastman 9921 coPET have been found to provide an ideal combination for producing thermally bondable, yet thermally stable fibers. The unexpected discovery is that F61HC and 9921 can be extruded through separate capillaries in a ratio ranging from 70:30 to 90:10 (F61HC:9921 ratio) and the resultant web can be thermally bonded together to produce a nonwoven that is thermally stable. Thermally stable in this example is defined as having less than 10% shrinkage in the MD in boiling water after 5 minutes. The thermal stability is achieved through a spinning speed greater than 4000 meter/minute and producing filament deniers ranging from 1 dpf to 10 dpf in both round and shaped fibers. Basis weights ranging from 5 $g/m^2$ to 100 $g/m^2$ have been produced. These fabrics have been produced with thermal point bonding. These types of fabrics can be used in a wide range of applications, such as disposable absorbent articles, dryer sheets, and roof felting. If desired, a multibeam system can be used alone or can have a fine fiber diameter layer placed in between two spunlaid layers and then bonded together.

An additional preferred embodiment is the use of polypropylene fibers and spunlaid nonwovens. The preferred resin properties for polypropylene are melt flow rates between 5 MFR (melt flow rate in grams per 10 minutes) and 400 MFR, with a preferred range between 10 MFR and 100 MFR and a still more preferred range between 15 MFR and 65 MFR with the most preferred range between 23 MFR and 40 MFR. The method used to measure MFR is outlined in ASTM D1238 measured at 230° C. with a mass of 2.16 kg.

The nonwoven products produced from the monocomponent and multicomponent fibers will also exhibit certain properties, particularly, strength, flexibility, softness, and absorbency. Measures of strength include dry and/or wet tensile strength. Flexibility is related to stiffness and can attribute to softness. Softness is generally described as a physiologically perceived attribute which is related to both flexibility and texture. Absorbency relates to the products' ability to take up fluids as well as the capacity to retain them. Absorbency in the present invention does not involve the internal regions of the fiber itself up taking water, such as is found with pulp fibers, regenerated cellulose fibers (e.g. rayon). Because some thermoplastic polymers inherently take-up small amount of water (e.g. polyamides), the water uptake is limited to less than 10 wt %, preferably less than 5 wt % and most preferably less than 1 wt %. The absorbency in the present invention arises from the hydrophilicity of the fibers and nonwoven structure and depends primarily on the fiber surface area, pore size, and bonding intersections. Capillarity is the general phenomenon used to describe the fluid interaction with the fibrous substrate. The nature of capillarity is well understood to those skilled in the art and is presented in detail in "Nonwovens: Theory, Process, Performance and Testing" by Albin Turbak, Chapter 4.

The spunlaid web forming the base substrate in the present invention will have an absorbency uptake or holding capacity ($C_{holding}$) between 1 g/g (gram per gram) to 10 g/g, more preferably between 2 g/g and 8 g/g and most preferably between 3 g/g and 7 g/g. This uptake measurement is done by weighing a dry sample (in grams) that is 15 cm long in MD and 5 cm wide in CD, dry weight is $m_{dry}$ then submerging the sample in distilled water for 30 seconds and then removing the sample from water, suspending it vertically (in MD) for 10 seconds and then weighing the sample again, wet weight is $m_{wet}$. The final wet sample weight ($m_{wet}$) minus the dry sample weight ($m_{dry}$) divided by the dry samples weight ($m_{dry}$) gives the absorbency or holding capacity for the sample ($C_{holding}$). i.e.:

$$C_{holding} := \frac{m_{wet} - m_{dry}}{m_{dry}}$$

The structured substrates have similar holding capacity.

The spunlaid process in the current invention will produce a spunlaid nonwoven with a desired basis weight. Basis weight is defined as a fiber/nonwoven mass per unit area. For the present invention, the basis weight of the base substrate is between 10 g/m² and 200 g/m², with a preferred range between 15 g/m² and 100 g/m², with a more preferred range between 18 g/m² and 80 g/m² and even a more preferred range between 25 g/m² and 72 g/m². The most preferred range is between 30 g/m² and 62 g/m².

The first step in producing a multiconstituent fiber is the compounding or mixing step. In the compounding step, the raw materials are heated, typically under shear. The shearing in the presence of heat will result in a homogeneous melt with proper selection of the composition. The melt is then placed in an extruder where fibers are formed. A collection of fibers is combined together using heat, pressure, chemical binder, mechanical entanglement, and combinations thereof resulting in the formation of a nonwoven web. The nonwoven is then modified and assembled into a base substrate.

The objective of the compounding step is to produce a homogeneous melt composition. For multiconstituent blends, the purpose of this step is to melt blend the thermoplastic polymers materials together where the mixing temperature is above the highest melting temperature thermoplastic component. The optional ingredients can also be added and mixed together. Preferably, the melt composition is homogeneous, meaning that a uniform distribution is found over a large scale and that no distinct regions are observed. Compatibilizing agents can be added to combine materials with poor miscibility, such as when polylactic acid is added to polypropylene or thermoplastic starch is added to polypropylene.

Twin-screw compounding is well known in the art and is used to prepare polymer alloys or to properly mix together polymers with optional materials. Twin-screw extruders are generally a stand alone process used between the polymer manufacture and the fiber spinning step. In order to reduce cost, the fiber extrusion can begin with twin-screw extruder such that the compounding is directly coupled with fiber making. In certain types of single screw extruders, good mixing and compatibilization can occur in-line.

The most preferred mixing device is a multiple mixing zone twin screw extruder with multiple injection points. A twin screw batch mixer or a single screw extrusion system can also be used. As long as sufficient mixing and heating occurs, the particular equipment used is not critical.

The present invention utilizes the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Spinning will occur at 120° C. to about 350° C., preferably 160° C. to about 320° C., most preferably from 190° C. to about 300° C. Fiber spinning speeds of greater than 100 meters/minute are required. Preferably, the fiber spinning speed is from about 1,000 to about 10,000 meters/minute, more preferably from about 2,000 to about 7,000, and most preferably from about 2,500 to about 5,000 meters/minute. The polymer composition must be spun fast to make strong and thermally stable fibers, as determined by single fiber testing and thermal stability of the base substrate or structured substrate.

The homogeneous melt composition can be melt spun into monocomponent or multicomponent fibers on commercially available melt spinning equipment. The equipment will be chosen based on the desired configuration of the multicomponent fiber. Commercially available melt spinning equipment is available from Hills, Inc. located in Melbourne, Fla. An outstanding resource for fiber spinning (monocomponent and multicomponent) is "Advanced Fiber Spinning Technology" by Nakajima from Woodhead Publishing. The temperature for spinning range from about 120° C. to about 350° C. The processing temperature is determined by the chemical nature, molecular weights and concentration of each component. Examples of air attenuation technology are sold commercially by Hill's Inc, Neumag and REICOFIL. An example of technology suitable for the present invention is the Reifenhäuser REICOFIL 4 spunlaid process. These technologies are well known in the nonwoven industry.

Fluid Handling

The structured substrate of the present invention can be used to manage fluids. Fluid management is defined as the intentional movement of fluid through control of the structured substrate properties. In the present invention, fluid management is achieved through two steps. The first step is engineering the base substrate properties through fiber shape, fiber denier, basis weight, bonding method, and surface energy. The second step involves engineering the void volume generated through fiber displacement.

Absorbent Articles

Figure 23:
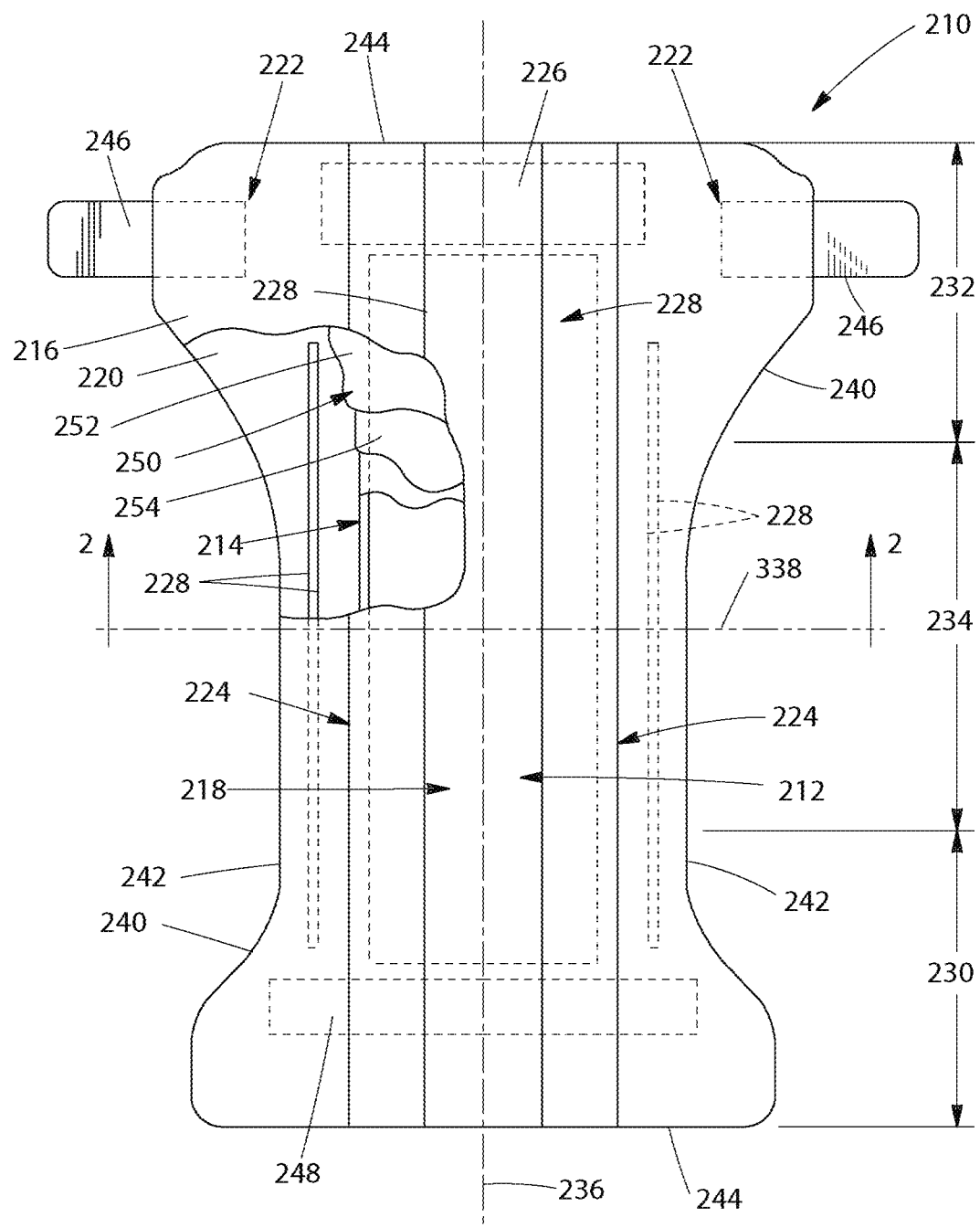
FIG. 23 is a plan view of a diaper in accordance with an embodiment of the present invention.

FIG. 23 is a plan view of a diaper 210 according to a certain embodiment of the present invention. The diaper 210 is shown in its flat out, uncontracted state (i.e., without elastic induced contraction) and portions of the diaper 210 are cut away to more clearly show the underlying structure of the diaper 210. A portion of the diaper 210 that contacts a wearer is facing the viewer in FIG. 23. The diaper 210 generally may comprise a chassis 212 and an absorbent core 214 disposed in the chassis.

The chassis 212 of the diaper 210 in FIG. 23 may comprise the main body of the diaper 210. The chassis 212 may comprise an outer covering 216 including a topsheet 218, which may be liquid pervious, and/or a backsheet 220, which may be liquid impervious. The absorbent core 214 may be encased between the topsheet 218 and the backsheet 220. The chassis 212 may also include side panels 222, elasticized leg cuffs 224, and an elastic waist feature 226.

The leg cuffs 224 and the elastic waist feature 226 may each typically comprise elastic members 228. One end portion of the diaper 210 may be configured as a first waist region 230 of the diaper 210. An opposite end portion of the diaper 210 may be configured as a second waist region 232 of the diaper 210. An intermediate portion of the diaper 210 may be configured as a crotch region 234, which extends longitudinally between the first and second waist regions 230 and 232. The waist regions 230 and 232 may include elastic elements such that they gather about the waist of the wearer to provide improved fit and containment (elastic waist feature 226). The crotch region 34 is that portion of the diaper 210 which, when the diaper 210 is worn, is generally positioned between the wearer's legs.

The diaper 210 is depicted in FIG. 23 with its longitudinal axis 236 and its transverse axis 238. The periphery 240 of the diaper 210 is defined by the outer edges of the diaper 210 in which the longitudinal edges 242 run generally parallel to the longitudinal axis 236 of the diaper 210 and the end edges 244 run between the longitudinal edges 242 generally parallel to the transverse axis 238 of the diaper 210. The chassis 212 may also comprise a fastening system, which may include at least one fastening member 246 and at least one stored landing zone 248.

The diaper 220 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 210 in place about the wearer, at least a portion of the first waist region 230 may be attached by the fastening member 246 to at least a portion of the second waist region 232 to form leg opening(s) and an article waist. When fastened, the fastening system carries a tensile load around the article waist. The fastening system may allow an article user to hold one element of the fastening system, such as the fastening member 246, and connect the first waist region 230 to the second waist region 232 in at least two places. This may be achieved through manipulation of bond strengths between the fastening device elements.

According to certain embodiments, the diaper 210 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 212 and absorbent core 214 may form the main structure of the diaper 210 with other features added to form the composite diaper structure. While the topsheet 218, the backsheet 220, and the absorbent core 214 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al., on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 218 in FIG. 23 may be fully or partially elasticized or may be foreshortened to provide a void space between the topsheet 218 and the absorbent core 214. Exemplary structures including elasticized or foreshortened topsheets are described in more detail in U.S. Pat. No. 5,037,416 entitled "Disposable Absorbent Article Having Elastically Extensible Topsheet" issued to Allen et al., on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 226 may be joined with the topsheet 218. The backsheet 220 may prevent the exudates absorbed by the absorbent core 214 and contained within the diaper 210 from soiling other external articles that may contact the diaper 210, such as bed sheets and undergarments. In certain embodiments, the backsheet 226 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 210 while still preventing liquid exudates from passing through the backsheet 210. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

Taking a cross section of FIG. 23 taken along the sectional line 2-2 of FIG. 23 and starting from the wearer facing side, the diaper 210 may comprise the topsheet 218, the components of the absorbent core 214, and the backsheet 220. Diaper 210 also comprises an acquisition system 250 disposed between the liquid permeable topsheet 218 and a wearer facing side of the absorbent core 214. The acquisition system 250 may be in direct contact with the absorbent core.

The acquisition system 250 comprises the fibrous web of the present invention. It is desirable for the present invention, that the absorbent articles as a whole are relatively thin. This results in less storage capacity and less shelf space being needed. Also, thinner absorbent articles have found to be more appealing to many consumers. In order to facilitate a thin absorbent article, the acquisition system also should be as thin as possible. However, thinner web materials often have lower temporary fluid holding capacity. Apart from being thin, the acquisition system should also be able to acquire fluid rapidly, to avoid leakage of the absorbent article due to free fluid on the topsheet. Also the acquisition system of the present invention should have good wicking capability, to allow for fluid transport towards the front and back waist region of the article. Thereby, it is possible to make more efficient use of the absorbent material comprised by the absorbent core. Also, increased liquid storage towards the front and back waist region enables absorbent articles with reduced bulk in the crotch region also when wet.

The fibrous web of the present invention may be used in the acquisition system with the second surface facing towards the topsheet. In these embodiments, the topsheet facing surface of the first region creates void volume that serves to temporarily hold liquid discharged into the absorbent article. I.e. not only the fibrous web itself but also the area immediately above the surface between the discontinuities of the fibrous web serves to hold the fluid. The discontinuities formed by the second regions and facing towards the topsheet serve as raised areas to maintain the distance between the topsheet and the first region of the fibrous web. The loose ends of the discontinuities formed by the second regions create a relatively open structure in the fibrous web, where liquid can readily and quickly enter into the fibrous web and into the absorbent core underneath the fibrous web or into additional lower layers of the acquisition system (in embodiments having additional acquisition system layers).

Alternatively, the fibrous web of the present invention may be used in the acquisition system with the first surface facing towards the topsheet. In these embodiments, the void volume inside the discontinuities serves to quickly acquire and temporarily hold fluid. The liquid can spread out to other areas of the fibrous web and to the absorbent core underneath the fibrous web especially through the loose ends formed by the displaced fibers.

In absorbent articles with absorbent cores having high amounts of absorbent polymer material, initial fluid absorption is often slower compared to absorbent cores having a certain amount of airfelt. In these absorbent articles it is especially important that the acquisition system is able to acquire and temporarily hold fluid. Also, absorbent cores with high amount of absorbent polymer material typically enable to make thin absorbent articles which are further supported by acquisition systems using the thin structured fibrous webs of the present invention.

Also, it is desirable to provide an acquisition system which enables vertical wicking of liquid which is faster than vertical wicking within absorbent cores having high amounts of absorbent polymer material.

The acquisition system 250 may consist only of the fibrous web of the present invention. However, the fibrous web may be a laminate, wherein the different layers of the laminate have been laminated to each other before the fibrous web undergoes the fiber displacement described herein.

Alternatively, the acquisition system may comprise the fibrous web of the present invention as an upper acquisition layer 252 facing towards the wearer's skin and a different, lower acquisition 254 layer facing the garment of the wearer. According to a certain embodiment, the acquisition system 250 may function to receive a surge of liquid, such as a gush of urine. In other words, the acquisition system 250 may serve as a temporary reservoir for liquid until the absorbent core 214 can absorb the liquid.

In a certain embodiment, the acquisition system 250 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, the lower acquisition layer 254 may consist of or may comprise a non-woven, which may be hydrophilic. Further, according to a certain embodiment, the lower acquisition layer 254 may comprise the chemically cross-linked cellulosic fibers, which may or may not form part of a nonwoven material. Further, according to an embodiment, the lower acquisition layer 254 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 254 has a total dry weight, the cross-linked cellulosic fibers are present on a dry weight basis in the upper acquisition layer in an amount from about 30% to about 95% by weight of the lower acquisition layer 254, and the other natural or synthetic polymeric fibers are present on a dry weight basis in the lower acquisition layer 254 in an amount from about 70% to about 5% by weight of the lower acquisition layer 254. According to another embodiment, the cross-linked cellulosic fibers are present on a dry weight basis in the first acquisition layer in an amount from about 80% to about 90% by weight of the lower acquisition layer 254, and the other natural or synthetic polymeric fibers are present on a dry weight basis in the lower acquisition layer 254 in an amount from about 20% to about 10% by weight of the lower acquisition layer 254.

According to a certain embodiment, the lower acquisition layer 254 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 254 has a maximum uptake of about 10 g/g.

Notably, the fibrous webs of the present invention may also be useful in other parts of an absorbent article. For example, topsheets and absorbent core layers comprising permanently hydrophilic non-wovens as described above have been found to work well.

The absorbent core 214 may comprise any absorbent material which is generally compressible, conformable, non-irritating to the wearer's skin, and capable of absorbing and retaining urine, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; absorbent polymer material or any other known absorbent material or combinations of materials. The absorbent material may be at least partially surrounded by a nonwoven fabric, often referred to as core wrap. The core wrap may consist of an upper layer towards the body-facing surface of the absorbent article and of a lower layer towards the garment-facing side of the absorbent article. The two layers may be continuously or intermittently bonded to each other around their perimeters. The upper and lower layer may be made of the same nonwoven fabric or may be made of different nonwoven fabric, i.e. the upper layer may be fluid pervious whereas the lower layer may be fluid impervious. The core wrap may also consist of a single nonwoven fabric, which envelops the absorbent material. It is preferred that the absorbent cores comprises more than 80% of absorbent polymer material by weight of absorbent material (i.e., excluding the core wrap, if present), more preferably more than 90%. The absorbent core may even be free of airfelt, i.e., 100% absorbent polymer material. The absorbent polymer material is preferably absorbent particulate polymer material.

The following base substrates were produced at Hills Inc on a 0.5 m wide spunbond line. The specifics are mentioned in each example. Measured properties of the materials produced in Examples 1, 2, 4, and 7 are produced in the tables provided below.

EXAMPLE 1

Spunbond fabrics were produced composed of 90 wt % Eastman F61HC PET resin and 10 wt % Eastman 9921 coPET. The spunbond fabrics were produced using a pronounced trilobal spinneret that had 1.125 mm length and 0.15 mm width with a round end point. The hydraulic length-to-diameter ratio was 2.2:1. The spinpack had 250 capillaries of which 25 extruded the coPET resin and 225 extruded the PET resin. The beam temperature used was 285° C. The spinning distance was 33 inches and the forming distance was 34 inches. Different distances could be used in this and subsequent examples, but distance indicated provided the best results. The remainder of the relevant process data is included in Table 1-3.

COMPARATIVE EXAMPLE 1

Spunbond fabrics were produced composed of 90 wt % Eastman F61HC PET resin and 10 wt % Eastman 20110. The spunbond fabrics were produced using a pronounced trilobal spinneret that had 1.125 mm length and 0.15 mm width with a round end point. The hydraulic length-to-diameter ratio was 2.2:1. The spinpack had 250 capillaries of which 25 extruded the coPET resin and 225 extruded the PET resin. The beam temperature used was 285° C. The spinning distance was 33 inches and the forming distance was 34 inches. It was difficult to produce thermally stable spunbond nonwovens with this polymer combination. The coPET fibers were not thermally stable and caused the entire fiber structure to shrink when heated above 100° C. The MD fabric shrinkage was 20%.

EXAMPLE 2

Spunbond fabrics were produced composed of 100 wt % Eastman F61HC PET. The spunbond fabrics were produced using a pronounced trilobal spinneret that had 1.125 mm length and 0.15 mm width with a round end point. The hydraulic length-to-diameter ratio was 2.2:1. The spinpack had 250 capillaries. The beam temperature used was 285° C. The spinning distance was 33 inches and the forming distance was 34 inches. The remainder of the relevant process data is included in Table 1-3.

EXAMPLE 3

Spunbond fabrics were produced composed of 90 wt % Eastman F61HC PET resin and 10 wt % Eastman 9921 coPET. The spunbond fabrics were produced using a standard trilobal spinneret that had 0.55 mm length and 0.127 mm width with a round end point with radius 0.18 mm. The hydraulic length-to-diameter ratio was 2.2:1. The spinpack had 250 capillaries of which 25 extruded the coPET resin and 225 extruded the PET resin. The beam temperature used was 285° C. The spinning distance was 33 inches and the forming distance was 34 inches. The remainder of the relevant process data is included in Table 4-6.

COMPARATIVE EXAMPLE 2

Spunbond fabrics were produced composed of 90 wt % Eastman F61HC PET resin and 10 wt % Eastman 20110. The spunbond fabrics were produced using a standard trilobal spinneret that had 0.55 mm length and 0.127 mm width with a round end point with radius 0.18 mm. The hydraulic length-to-diameter ratio 2.2:1. The spinpack had 250 capillaries of which 25 extruded the coPET resin and 225 extruded the PET resin. The beam temperature used was 285° C. The spinning distance was 33 inches and the forming distance was 34 inches. It was difficult to produce thermally stable spunbond nonwovens with this polymer combination. The coPET fibers were not thermally stable and caused the entire fiber structure to shrink when heated above 100° C. The MD fabric shrinkage was 20%.

EXAMPLE 4

Spunbond fabrics were produced composed of 90 wt % Eastman F61HC PET resin and 10 wt % Eastman 9921 coPET. The spunbond fabrics were produced using a solid round spinneret with capillary exit diameter of 0.35 mm and length-to-diameter ratio 4:1. The spinpack had 250 capillaries of which 25 extruded the coPET resin and 225 extruded the PET resin. The beam temperature used was 285° C. The spinning distance was 33 inches and the forming distance was 34 inches. The remainder of the relevant process data is included in Table 7-9.

COMPARATIVE EXAMPLE 3

Spunbond fabrics were produced composed of 90 wt % Eastman F61HC PET resin and 10 wt % Eastman 20110. The spunbond fabrics were produced using a solid round spinneret with capillary exit diameter of 0.35 mm and length-to-diameter ratio 4:1. The spinpack had 250 capillaries of which 25 extruded the coPET resin and 225 extruded the PET resin. The beam temperature used was 285° C. The spinning distance was 33 inches and the forming distance was 34 inches. It was difficult to produce thermally stable spunbond nonwovens with this polymer combination. The coPET fibers were not thermally stable and caused the entire fiber structure to shrink when heated above 100° C. The MD fabric shrinkage was 20%.

Sample Description: The following information provides sample description nomenclature used to identify the examples in the tables of data provided below.

The first number references the example number in which it was produced.

The letter following the number is to designate a sample produced under a different condition in the example description, which is described broadly. This letter and number combination specifies production of a base substrate.

A number following the letter designates production of a structured substrate, which is described in the patent. Different numbers indicate different conditions used to produce the structured substrate.

There are two reference samples included in the present invention to compare the base substrate and structured substrate samples vs carded resin bonded samples.

43 g/m² —Consisting of 30% styrene butadiene latex binder and 70% of a fiber mix. The fiber mix contains a 40:60 mixture of 6 den solid round PET fibers and 9 den solid round PET fibers respectively.

60 g/m² —Consisting of 30% (carboxylated) styrene butadiene latex binder and 70% of a fiber mix. The fiber mix contains a 50:50 mixture of 6 den solid round PET fibers and 9 den hollow spiral PET fibers (25-40% hollow) respectively.

If samples in any of the methods being disclosed have been previously aged or has been removed from a product, they should be stored at 23±2° C. and at 50±2% relative humidity for 24 hours with no compression, prior to any of the testing protocols. The samples after this aging would be referred to as "as-produced".

Definitions and Test Method for Properties in Invention: The test methods for properties in the property tables are listed below. Unless specified otherwise, all tests are carried out at about 23±2° C. and at 50±2% relative humidity. Unless specified explicitly, the specific synthetic urine used is made with 0.9% (by weight) saline (NaCL) solution made with deionized water.

Mass Throughput: Measures the polymer flow rate per capillary, measured in grams per hole per minute (GHM) and is calculated based on polymer melt density, polymer melt pump displacement per revolution and number of capillaries fed by the melt pump.

Shape: Designates the fiber shape based on the capillary geometry listed in the Example Designation.

Actual Basis Weight: The preferred basis weight is measured by cutting out at least ten 7500 mm² (50 mm wide by 150 mm long sample size) sample areas at random from the sample and weighing them to within ±1 mg, then averaging the mass by the total number of samples weighed. Basis Weight units are in grams per square meter (g/m²). If 7500 mm square area cannot be used for basis weight measurement, then the sample size can be reduced down to 2000 mm², (for example 100 mm by 20 mm sample size or 50 mm by 40 mm sample size), but the number of samples should be increased to at least 20 measurements. The actual basis weight is determined by dividing the average mass by the sample area and making sure the units are in grams per square meter.

Fabric Thickness: Thickness is also referred to as caliper and the two words are used interchangeably. Fabric thickness and fresh caliper refer to the caliper without any aging conditions. The test conditions for as-produced caliper are measured at 0.5 kPa and at least five measurements are averaged. A typical testing device is a Thwing Albert ProGage system. The diameter of the foot is between 50 mm to 60 mm. The dwell time is 2 seconds for each measurement. The sample must be stored at 23±2° C. and at 50±2% relative humidity for 24 hours with no compression, then subjected to the fabric thickness measurement. The preference is to make measurements on the base substrate before modification, however, if this material is not available an alternative method can be used. For a structured substrate, the thickness of the first regions in between the second regions (displaced fiber regions) can be determined by using a electronic thickness gauge (for instance available from McMaster-Carr catalog as Mitutoyo No 547-500). These electronic thickness gauges can have the tips changed to measure very small areas. These devises have a preloaded spring for making the measurement and vary by brand. For example, a blade shaped tip can be used that is 6.6 mm long and 1 mm wide. Flat round tips can also be inserted that measure area down below 1.5 mm in diameter. For measuring on the structured substrate, these tips need to be inserted between the structured regions to measure the as-produced fabric thickness. The pressure used in the measurement technique cannot be carefully controlled using this technique, with the applied pressure being generally higher than 0.5 kPa.

Aged Caliper: This refers to the sample caliper after it has been aged at 40° C. under 35 kPa pressure for 15 hours and then relaxed at 23±2° C. and at 50±2% relative humidity for 24 hours with no compression. This can also be called the caliper recovery. The aged caliper is measured under a pressure of 2.1 kPA. A typical testing device is a Thwing Albert ProGage system. The diameter of the foot is between 50 mm to 60 mm. The dwell time is 2 seconds for each measurement. All samples are stored at 23±2° C. and at 50±2% relative humidity for 24 hours with no compression, and then subjected to the aged caliper test.

Figure 19A:
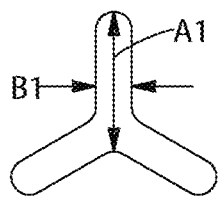
FIG. 19*a* through 19*c* are cross sections of shaped fiber configurations.
Figure 19B:
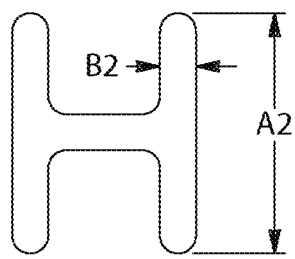
Figure 19C:
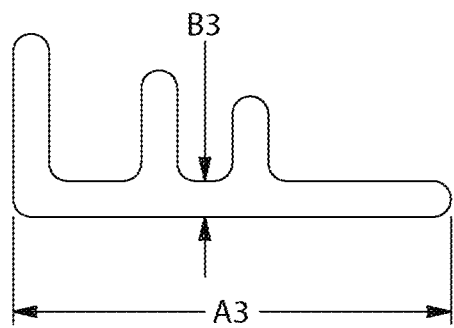

Mod Ratio: The "Mod Ratio" or modification ratio is used to compensate for additional surface area geometry of non-round fibers. The modification ratio is determined by measuring the longest continuous straight line distance in the cross section of the fiber perpendicular to its longest axis, and dividing by the width of the fiber at 50% of that distance. For some complex fiber shapes, it may be difficult to easily determine the modification ratio. FIG. 19a-19c provide examples of shaped fiber configurations. The "A" designation is the long axis dimension and the "B" designation is the width dimension. The ratio is determined by dividing the short dimension into the long dimension. These units are measured directly via microscopy.

Actual Denier: Actual denier is the measured denier of the fiber for a given example. Denier is defined as the mass of a fiber in grams at 9000 linear meters of length. Thus the inherent density of the fiber is also factored in for the calculation of denier when comparing fibers from different polymers, expressed as dpf (denier per filament), so a 2 dpf PP fiber and a 2 dpf PET fiber will have different fiber diameters. An example of the denier to diameter relationship for polypropylene is a 1 dpf fiber of polypropylene that is solid round with a density of about 0.900 g/cm³ has a diameter of about 12.55 micrometers. The density of PET fibers in the present invention are taken to be 1.4 g/cm³ (grams per cubic centimeter) for denier calculations. For those skilled in the art, converting from solid round fiber diameter to denier for PP and PET fibers is routine.

Equivalent Solid Round Fiber Diameter: The equivalent solid round fiber diameter is used for calculating the modulus of fibers for fiber property measurements for non-round or hollow shaped fibers. The equivalent solid round fiber diameter is determined from the actual denier of the fiber. The actual denier of the non-round fiber is converted into an equivalent solid round fiber diameter by taking the actual fiber denier and calculating the diameter of the filament with the assumption it was solid round. This conversion is important for determining the modulus of a single fiber for a non-round fiber cross-section.

Tensile Properties of the Nonwoven Fabrics: The tensile properties of base substrates and structured substrates were all measured the same way. The gauge width is 50 mm, gauge length is 100 mm and the extension rate is 100 mm/min. The values reported are for strength and elongation at peak, unless stated otherwise. Separate measurements are made for the MD and CD properties. The typical units are Newton (N) per centimeter (N/cm). The values presented are the average of at least five measurements. The perforce load is 0.2 N. The samples should be stored at 23±2° C. and at 50±2% relative humidity for 24 hours with no compression, then tested at 23±2° C. and at 50±2%. The tensile strength as reported here is the peak tensile strength in the stress-strain curve. The elongation at tensile peak is the percent elongation at which the tensile peak is recorded.

MD/CD Ratio: Is defined as the MD tensile strength divided by the CD tensile strength. The MD/CD ratio is a method used for comparing the relative fiber orientation in a nonwoven fibrous substrate.

Fiber Perimeter: Was directly measured via microscopy and is the perimeter of a typical fiber in the nonwoven, expressed in micrometers. The values presented are the average of at least five measurements.

Opacity: Opacity is a measurement of the relative amount of light that passes through the base substrate. The characteristic opacity depends, amongst others, on the number, size, type and shape of fibers present in a given location that is measured. For the present invention, the base substrate opacity is preferably greater than 5%, more preferably greater than 10%, more preferably greater than 20%, still more preferably greater than 30% and most preferably greater than 40%. Opacity is measured using TAPPI Test Method T 425 om-01 "Opacity of Paper (15/d geometry, Illuminant A/2 degrees, 89% Reflectance Backing and Paper Backing)". The opacity is measured as a percentage.

Base Substrate Density: The base substrate density is determined by dividing the actual basis weight of the sample by the aged caliper of the sample, converting into the same units and reporting as grams per cubic meter.

Base Substrate Specific Volume: The base substrate specific volume is the inverse of base substrate density in units of cubic centimeters per gram.

Line Speed: The line speed is the linear machine direction speed at which the sample was produced.

Bonding Temperature: The bonding temperature is the temperature at which the spunbond sample was bonded together. Bonding temperature includes two temperatures. The first temperature is the temperature of the engraved or patterned roll and the second is the temperature of the smooth roll. Unless specified otherwise, the bonding area was 18% and the calendar linear pressure was 400 pounds per linear inch.

Surfactant Addition to Invention Samples: Refers to the material used for treating the base substrate and structured substrates to render them hydrophilic. In the present invention the same surfactant was used for all samples. The surfactant was a Procter & Gamble development grade material with code DP-988A. The material is a polyester polyether copolymer. Commercial grade soil release polymers (SRPs) from Clariant (TexCare SRN-240 and TexCare SRN-170) was also used and found to work well. The basic procedure was as follows:

200 mL of surfactant is mixed with 15 L of tap water at 80° C. in a five gallon bucket.

The samples to be coated are placed into the diluted surfactant bucket for five minutes. Each sample is nominally 100 mm wide and 300 mm long. Up to nine samples are placed in the bucket at one time, with the samples being agitated for the first ten seconds. The same bucket can be used for up to 50 samples.

Each sample is then removed, held vertically over the bucket at one corner and residual water drained into the bucket for five to ten seconds.

The samples are rinsed and soaked in a clean bucket of tap water for at least two minutes. Up to nine samples are placed in the bucket at one time, with the samples being agitated for the first ten seconds. The rinse bucket is changed after one set of nine samples.

The sample is dried at 80° C. in a forced air oven until dry. A typical time is two to three minutes.

Holding Capacity: The holding capacity measurement takes the surfactant coated sample and measures fluid uptake of the material. The 200 mm×100 mm sample is submerged in tap water at 20° C. for one minute and then removed. The sample is held by one corner upon removal for 10 seconds and then weighed. The final weight is divided by the initial weight to calculate the holding capacity. Holding capacity is measured on as-produced fabric samples that correspond to conditions measured in the as-produced fabric thickness test, unless specified otherwise. These samples are not compression aged before testing. Different samples sizes can be used in this test. Alternative samples sizes that can be used are 100 mm×50 mm or 150 mm×75 mm. The calculation method is the same regardless of the sample size selected.

Wicking Spread Area: The wicking spread is broken down into a MD and CD spread. A surfactant treated sample is cut that is at least 30 cm long and 20 cm wide. Non-treated samples do not wick any fluid. The sample is set on top of a series of petri dishes (10 cm diameter and 1 cm deep) with one centered in the middle of the sample and two on either side. 20 mL of distilled water is then pored onto the sample at a rate of 5 mL per second. The engraved roll side of the nonwoven is up, facing the fluid pouring direction. The distance the fluid is wicked is measured in the MD and CD after one minute. The distilled water can be colored if needed (Merck Indigo-carmin c.i. 73015). The pigment should not alter the surface tension of the distilled water. At least three measurements should be made per material. Wicking spread is measured on as-produced fabric samples that correspond to conditions measured in the as-produced fabric thickness test, unless specified otherwise. These samples are not compression aged before testing. If samples size smaller than 30 cm long and 20 cm wide is used, the sample must first be tested to determine if the wicking spreads to the edges of the material before one minute. If the wicking spread in the MD or CD is greater than the sample width before one minute, the MD horizontal wicking test height method should be used. The petri dishes are emptied and cleaned for every measurement.

MD Horizontal Transport:

Apparatus

| | |
|---|---|
| Pipette or Burette: | being able to discharge 5.0 ml |
| Tray: | size: width: 22 cm ± 1 cm, length: 30 cm ± 5 cm, height: 6 cm ± 1 cm |
| Funnel: | 250 ml glass funnel attached with valve, orifice diameter: 7 mm |
| Metal clamps: | width of clamps: 5 cm |
| Scissors: | Suitable for cutting samples for desired dimension |
| Balance: | having an accuracy of 0.01 g |

Reagent
    Simulated urine: Prepare a 0.9% saline solution (9.0 g/l of analytical grade sodium chloride in deionized water, with a surface tension of 70±2 mN/m at 23±2° C. colored with blue pigment (e.g. Merck Indigocarmin c.i. 73015)

Facilities
    Conditioned Room . . . Temperature . . . 23° Celsius (±2° C.)
    Relative Humidity . . . 50% (±2%)

Procedure
1.) Cut a sample (70±1) mm wide * (300±1) mm long in machine direction
2.) Measure and report the weight (w1) of the sample to the nearest 0.01 g
3.) Clamp the sample with the baby side upwards (textured side if measuring the structured substrate or engraved roll side if measuring the base substrate) over the width on the upper edges of the tray. Material is now hanging freely above the bottom of the tray.
4.) Adjust the outlet of a 250 ml glass funnel attached with a valve 25.4±3 mm above the sample centered in machine and cross direction over the sample
5.) Prepare the simulated urine
6.) Dispense with the pipette or burette 5.0 ml of simulated urine (4.) into the funnel, while keeping the valve of the funnel closed
7.) Open the valve of the funnel to discharge the 5.0 ml of simulated urine
8.) Wait for a time period of 30 seconds (use stopwatch)
9.) Measure the max MD distribution. Report to the nearest centimeter.

Vertical Wicking Height: The vertical wicking test is conducted by placing a preferred samples size of at least 20 cm long and 5 cm wide sample, held vertically above a large volume of distilled water. The lower end of the sample is submerged in the water to at least one cm under the fluid surface. The highest point the fluid rises to in five minutes is recorded. Vertical wicking is measured on as-produced fabric samples that correspond to conditions measured in the as-produced fabric thickness test, unless specified otherwise. Other sample sizes can be used, however, the sample width can effect the measurement when performed on a structured substrate. The smallest samples width should be 2 cm wide, with a minimum length of 10 cm.

Thermal Stability: Thermal stability of the base substrate or structured substrate nonwoven is assessed based on how much a 10 cm in MD×at least 2 cm in CD sample shrinks in boiling water after five minutes. The base substrate should shrink less than 10%, or have a final dimension in the MD of more than 9 cm to be considered thermally stable. If the sample shrinks more than 10% it is not thermally stable. The measurement was made by cutting out the 10 cm by 2 cm sample size, measuring the exact length in the MD and placing the sample in boiling water for five minutes. The sample is removed and the sample length measured again the MD. For all samples tested in the present invention, even ones with high shrinkage in the comparative examples, the sample remained flat after the time in the boiling water. Without being bound by theory, the nonwoven thermal stability depends on the thermal stability of constituent fibers. If the fibers comprising the nonwoven shrink, the nonwoven will shrink. Therefore, the thermal stability measurement here also captures the thermal stability of the fibers. The thermal stability of the nonwoven is important for the present invention. For samples that show significant shrinkage, well beyond the 10% preferred in the present invention, they can bundle or curl up in boiling water. For these samples, a 20 gram weight can be attached at the bottom of the sample and the length measured vertically. The 20 gram weight can be metal binder clips or any other suitable weight that can attached at the bottom and still enable the length to be measured.

FDT: FDT stands for Fiber Displacement Technology and refers to mechanical treatment of the base substrate to form a structured substrate having displaced fibers. If the base substrate is modified by any type of fiber deformation or relocation, it has undergone FDT. Simple handling of a nonwoven across flat rollers or bending is not FDT. FDT implies deliberate movement of fibers through focused mechanical or hydrodynamic forces for the intentional movement of fibers in the z-directional plane.

Strain Depth: The mechanical straining distance used in the FDT process.

Over Thermal Bond: Designates whether or not the sample has been overbonded with a second discrete bonding step, using heat and/or pressure.

FS-Tip: Designates whether the tip or top of the displaced fibers have been bonded.

Structured Substrate Density: The structured substrate density is determined by dividing the actual basis weight by the structured substrate aged caliper, converting into the same units and reporting as grams per cubic centimeter.

Structured Substrate Specific Volume: The structured substrate volume is the inverse of structured substrate density in units of cubic centimeters per gram.

Void Volume Creation: Void volume creation refers the void volume created during the fiber displacement step. Void volume creation is the difference between the structured substrate specific volume and the base substrate specific volume.

Aged Strike Through and Rewet Test: For the Strike Through test Edana method 150.3-96 has been used with the following modifications:

B. Testing Conditions
    Conditioning of samples and measurement is carried out at 23° C.±2° C. and 50%±5% humidity E: Equipment
    As reference absorbing pad 10 layers of Ahlström Grade 989 or equivalent (av. Strike Through time: 1.7±0.3 s, dimensions: 10×10 cm)

F: Procedure
- 2. Reference absorbent pad as described in E
- 3. Test piece is cut into rectangle of 70×125 mm
- 4. Conditioning as described in B
- 5. The test piece is placed on set of 10 plies of filter paper. For structured substrates the structured side is facing upward.
- 10. The procedure is repeated 60 s after absorption of the $1^{st}$ gush and the $2^{nd}$ gush respectively to record the time of the $2^{nd}$ and $3^{rd}$ Strike Through.
- 11. A minimum of 3 tests on test pieces from each specimen is recommended.

For the measurement of the rewet the Edana method 151.1-96 has been used with the following modifications:

B. Testing Conditions
Conditioning of samples and measurement is carried out at 23° C.±2° C. and 50%±5% humidity D. Principle
The set of filter papers with the test piece on top from the Strike Through measurement is used to measure the rewet.

E. Equipment
Pick-up paper: Ahlström Grade 632 or equivalent, cut into dimensions of 62 mm×125 mm, centered on top of the test piece so that it is not in contact with the reference absorbent pad.
Simulated Baby Weight: Total weight 3629 g±20 g F. Procedure
- 12. Start procedure as of step 12 directly after completion of the $3^{rd}$ gush of the Strike Through method. The additional quantity (L) is determined by subtracting the 15 ml of the 3 gushes of the Strike Through test from the total quantity of liquid (Q) required for the wetback test.
- 21. The wetback value equals the rewet in the present invention.

Fiber Properties: Fiber properties in the present invention were measured using an MTS Synergie 400 series testing system. Single fibers were mounted on template paper that has been precut to produce holes that are exactly 25 mm length and 1 cm wide. The fibers were mounted such that they are length wise straight across the hole in the paper with no slack. The average fiber diameter for solid round or equivalent solid round fiber diameter for non-round is determined by making at least ten measurements. The average of these ten measurements is used as the fiber diameter in determining the fiber modulus through the software input. The fibers were mounted into the MTS system and the sides of the template paper were cut before testing. The fiber sample is strained at 50 mm/min speed with the strength profile initiated with a load force above 0.1 g of force. The peak fiber load and strain at break are measured with the MTS software. The fiber modulus is also measured by the MTS at 1% strain. The fiber modulus as presented in Table 10 was reported in this manner. The elongation at fiber break and peak fiber load are also reported in Table 10. The results are an average of ten measurements. In calculating the modulus of the fibers, the fiber diameter is used for solid round fibers or the equivalent solid round fiber diameter is used for non-round or hollow fibers.

Percentage of Broken Filaments: The percentage of broken filaments at a fiber displacement location can be measured. The method for determining the number of broken filaments is by counting. Samples produced having displaced fibers can be with or without tip bonding. Precision tweezers and scissors are needed for making actual fiber count measurements. The brand Tweezerman makes such tools for these measurements, such as Tweezers with item code 1240T and scissors with item code 3042-R can be used. Medical Supplier Expert item code MDS0859411 can also be used for scissors. Other suppliers also make tooling that can be used.

Figure 17A:
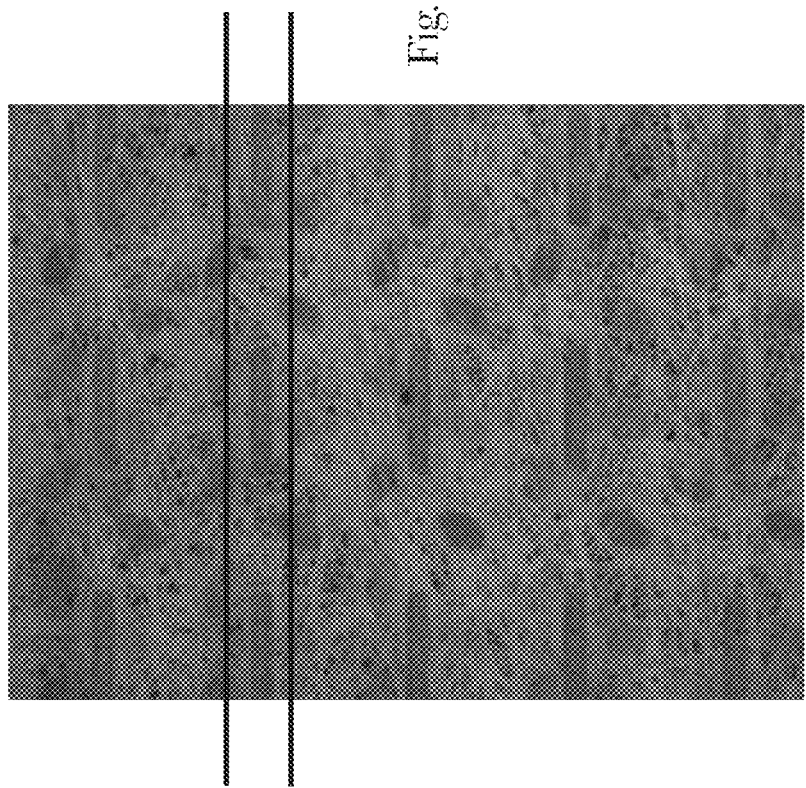
FIG. 17*a* and 17*b* are photomicrographs of portions of a web of the present invention showing portions of the structured substrate that are cut in order to determine the number of displaced fibers.
Figure 17B:
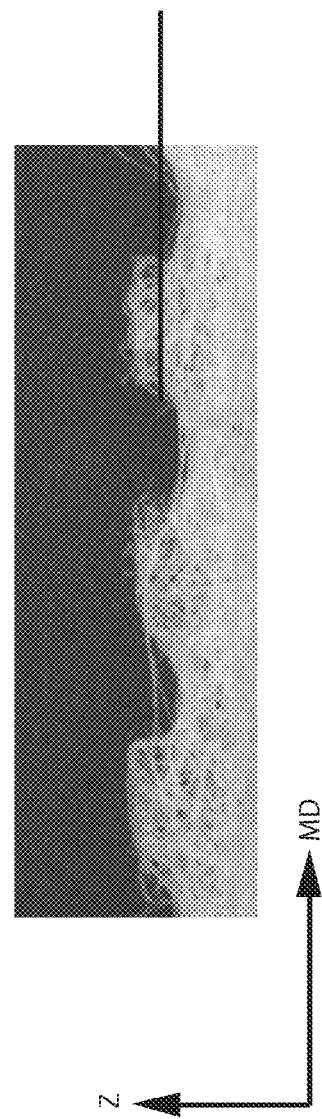

For samples without tip bonding: Generally, one side of the displaced fiber location will have more broken filaments as shown in FIG. 16. The structured fibrous web should be cut on the first surface at the side of the displaced fibers in the second region with fewer broken filaments. As shown in FIG. 16, this would be the left side identified as the $1^{st}$ cut 82. This should be cut along the first surface at the base of the displaced fibers. The cutting is shown in FIGS. 17a and 17b. The side view shown in FIG. 17b is oriented in the MD as shown. Once this cut is made, any loose fibers should be shaken free or brushed off until no more fibers fall out. The fibers should be collected and counted. Then the other side of the second region should be cut (identified as the $2^{nd}$ cut 84 in FIG. 16) and the number of fibers counted. The first cut details the number of broken fibers. The number of fibers counted in the first cut and second cut combined equals the total number of fibers. The number of fibers in the first cut divided by the total number of fibers times 100 gives the percentage of broken fibers. In most cases, a visual inspection can show whether or not the majority of the fibers are broken. When a quantitative number is needed, the procedure above should be used. The procedure should be done on at least ten samples and the total averaged together. If the sample has been compressed for some time, it may need to be lightly brushed before cutting to reveal the dislocation area for this test. If the percentages are close and a statically significant samples size has not been generated, the number of samples should be increased by increments of ten to render sufficient statistical certainty within a 95% confidence interval.

Figure 18:
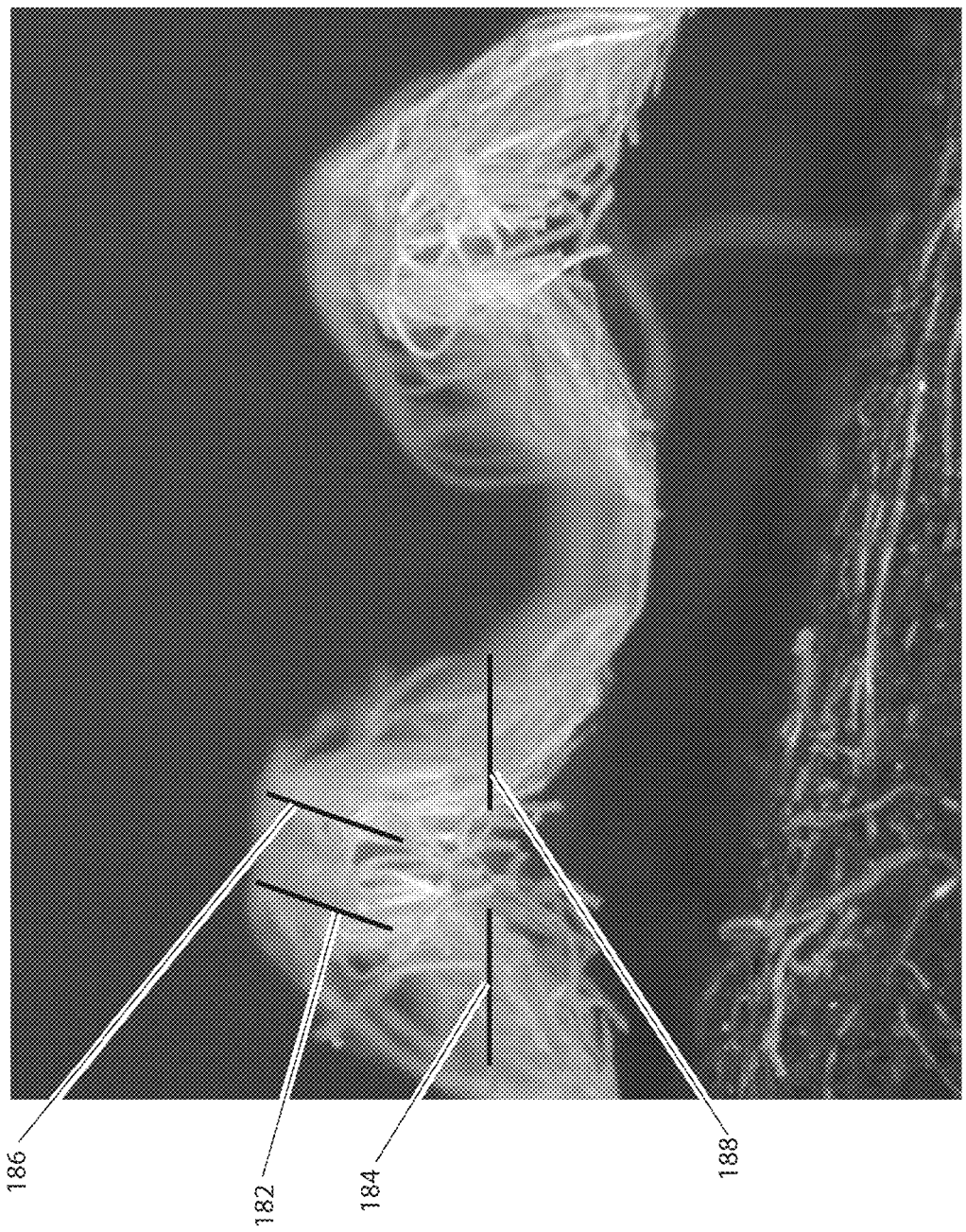
FIG. 18 is a photomicrograph of a portion of a web of the present invention identifying locations along tip bonded displaced fibers of the structured substrate that are cut in order to determine the number of displaced fibers.

For samples with tip bonding: Generally, one side of the displaced fiber location will have more broken filaments as shown in FIG. 18. The side with fewer broken filaments should be cut first. As shown in FIG. 18, this would be the left side upper region labeled as the $1^{st}$ cut, which is at the top of the where the tip bond is located, but does not include any of the tip bonded material (i.e., it should be cut on the side of the tip bond towards the side of the broken fibers). This cut should be made and loose fibers shaken free, counted and designated as fiber count 1. The second cut should be at the base of the displaced fibers, labeled as the second cut FIG. 18. The fibers should be shaken loose and counted, with this count designated as fiber count 2. A third cut is made on the other side of the tip bonded region, shaken, counted and designated as fiber count 3. A fourth cut is made at the base of the displaced fibers, shaken loose and counted and designated as fiber count 4. The cutting is shown in FIG. 17a and 17b. The number of fibers counted in the fiber count 1 and fiber count 2 equals the total number of fibers on that side 1-2. The number of fibers counted in the fiber count 3 and fiber count 4 equals the total number of fibers on that side 3-4. The difference between fiber count 1 and fiber count 2 is determined and then divided by the sum of fiber count 1 and fiber count 2 then multiplied by 100 and is called broken filament percentage 1-2. The difference between fiber count 3 and fiber count 4 is determined and then divided by the sum of fiber count 3 and fiber count 4 then multiplied by 100 and is called broken filament percentage 3-4. For the present invention broken filament percentage 1-2 or broken filament percentage 3-4 should be greater than 50%. In most cases, a visual inspection can show whether or not the majority of the fibers are broken. When a quantitative number is needed, the procedure above should be used. The procedure should be done on at least ten samples and the total averaged together. If the sample has been compressed for some time, it may need to be lightly brushed before cutting to reveal the dislocation area for this test. If the percentages are close and a statically significant samples size has not been generated, the number of samples should be increased by increments of ten to render sufficient statistical certainty within a 95% confidence interval.

In Plane Radial Permeability (IPRP): In plane radial permeability or IPRP or shortened to permeability in the present invention is a measure of the permeability of the nonwoven fabric and relates to the pressure required to transport liquids through the material. The following test is suitable for measurement of the In-Plane Radial Permeability (IPRP) of a porous material. The quantity of a saline solution (0.9% NaCl) flowing radially through an annular sample of the material under constant pressure is measured as a function of time. (Reference: J. D. Lindsay, "The anisotropic Permeability of Paper" TAPPI Journal, (May 1990, pp 223) Darcy's law and steady-state flow methods are used for determining in-plane saline flow conductivity).

Figure 20:
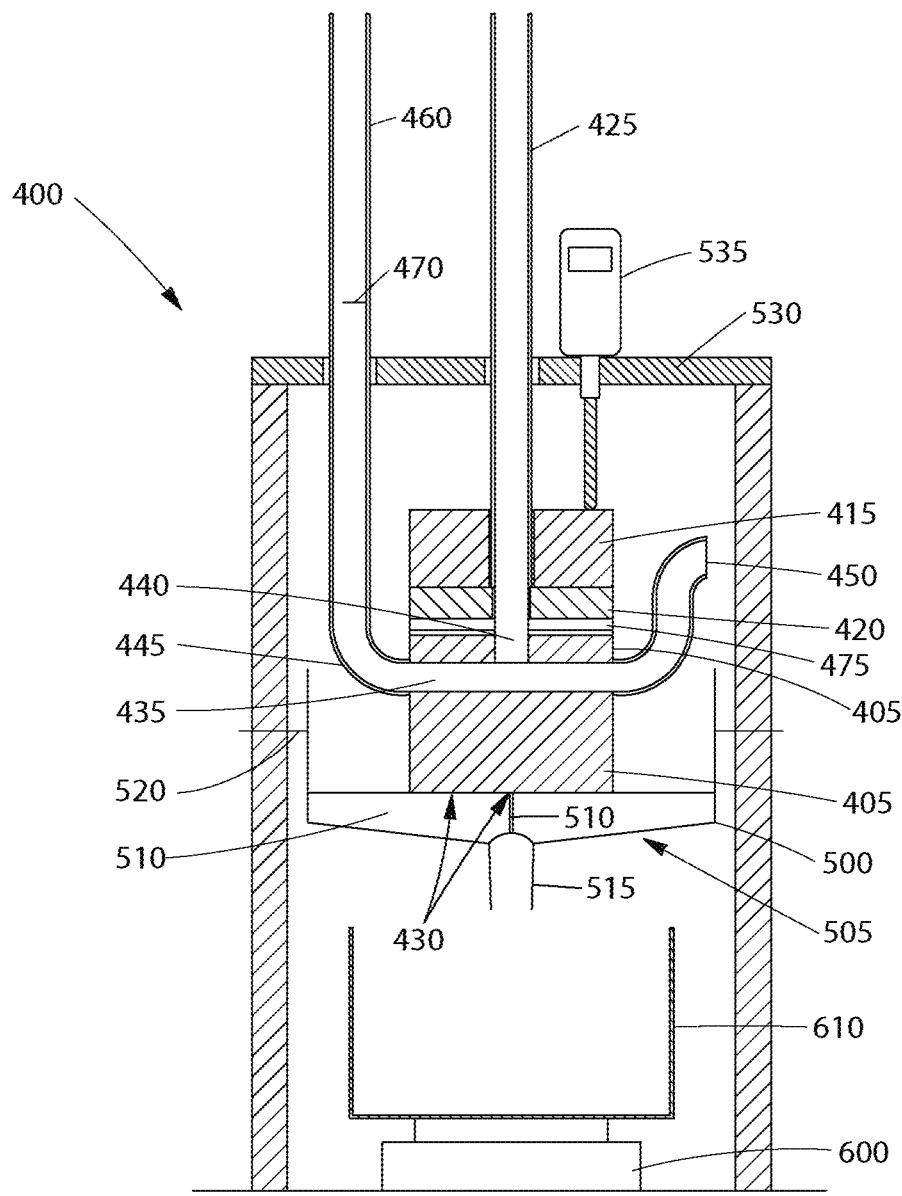
FIG. 20 is a schematic representation of an in plane radial permeability apparatus set up.
Figure 21A:
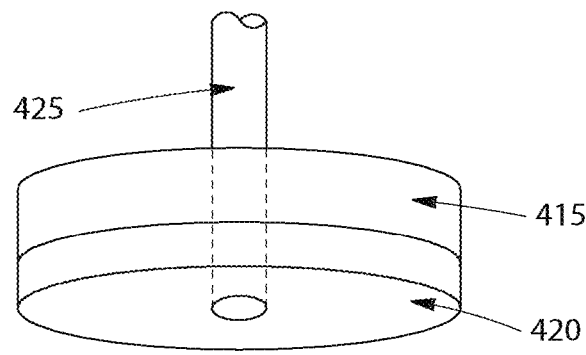
FIG. 21A, 21B and 21C are alternate views of a portion of the in plane radial permeability apparatus set up shown in FIG. 20.
Figure 21B:
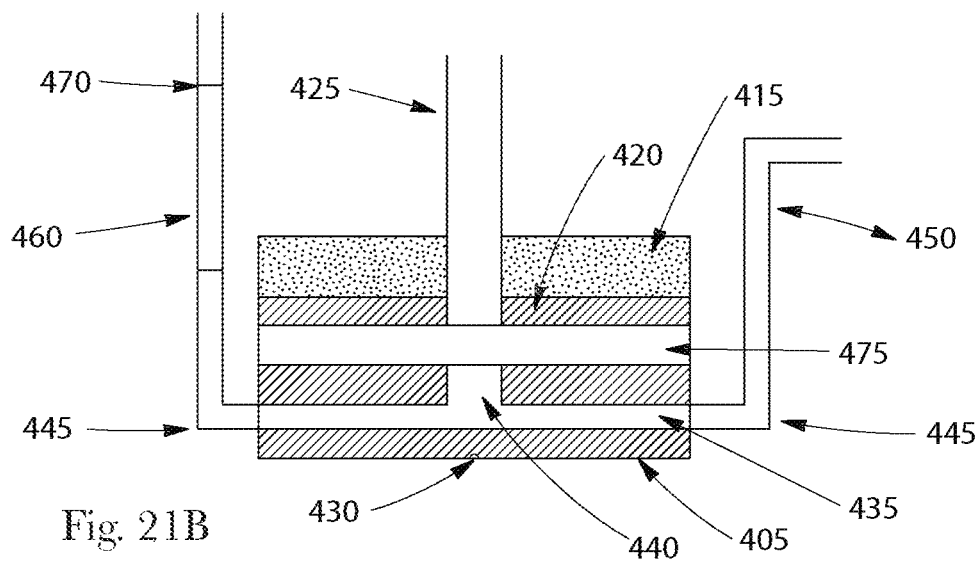
Figure 21C:
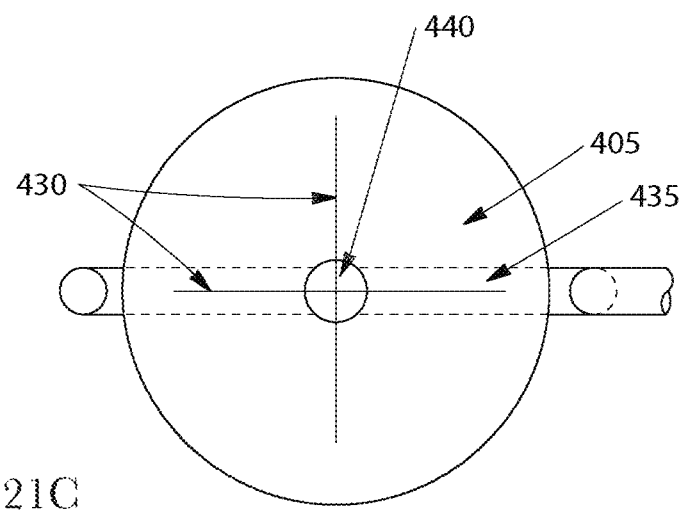

The IPRP sample holder 400 is shown in FIG. 20 and comprises a cylindrical bottom plate 405, top plate 420, and cylindrical stainless steel weight 415 shown in detail in FIG. 21A-C.

Top plate 420 is 10 mm thick with an outer diameter of 70.0 mm and connected to a tube 425 of 190 mm length fixed at the center thereof. The tube 425 has in outer diameter of 15.8 mm and an inner diameter of 12.0 mm. The tube is adhesively fixed into a circular 12 mm hole in the center of the top plate 420 such that the lower edge of the tube is flush with the lower surface of the top plate, as depicted in FIG. 21A. The bottom plate 405 and top plate 420 are fabricated from Lexan® or equivalent. The stainless steel weight 415 shown in FIG. 21B has an outer diameter of 70 mm and an inner diameter of 15.9 mm so that the weight is a close sliding fit on tube 425. The thickness of the stainless steel weight 415 is approximately 25 mm and is adjusted so that the total weight of the top plate 420, the tube 425 and the stainless steel weight 415 is 788 g to provide 2.1 kPa of confining pressure during the measurement.

As shown in FIG. 21C, bottom plate 405 is approximately 50 mm thick and has two registration grooves 430 cut into the lower surface of the plate such that each groove spans the diameter of the bottom plate and the grooves are perpendicular to each other. Each groove is 1.5 mm wide and 2 mm deep. Bottom plate 405 has a horizontal hole 435 which spans the diameter of the plate. The horizontal hole 435 has a diameter of 11 mm and its central axis is 12 mm below the upper surface of bottom plate 405. Bottom plate 405 also has a central vertical hole 440 which has a diameter of 10 mm and is 8 mm deep. The central hole 440 connects to the horizontal hole 435 to form a T-shaped cavity in the bottom plate 405. As shown in FIG. 21B, the outer portions of the horizontal hole 435 are threaded to accommodate pipe elbows 445 which are attached to the bottom plate 405 in a watertight fashion. One elbow is connected to a vertical transparent tube 460 with a height of 190 mm and an internal diameter of 10 mm. The tube 460 is scribed with a suitable mark 470 at a height of 50 mm above the upper surface of the bottom plate 420. This is the reference for the fluid level to be maintained during the measurement. The other elbow 445 is connected to the fluid delivery reservoir 700 (described below) via a flexible tube.

Figure 22:
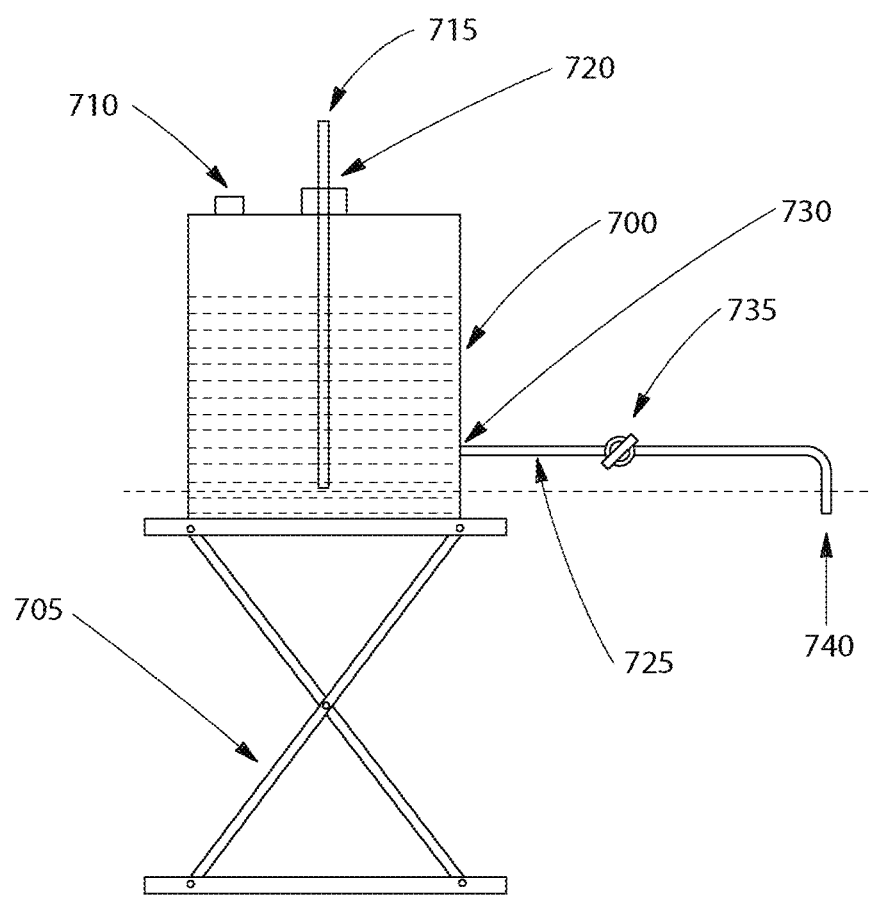
FIG. 22 is a schematic representation of a fluid delivery reservoir for the in plane radial permeability apparatus set up shown in FIG. 20.

A suitable fluid delivery reservoir 700 is shown in FIG. 22. Reservoir 700 is situated on a suitable laboratory jack 705 and has an air-tight stoppered opening 710 to facilitate filling of the reservoir with fluid. An open-ended glass tube 715 having an inner diameter of 10 mm extends through a port 720 in the top of the reservoir such that there is an airtight seal between the outside of the tube and the reservoir. Reservoir 700 is provided with an L-shaped delivery tube 725 having an inlet 730 that is below the surface of the fluid in the reservoir, a stopcock 735, and an outlet 740. The outlet 740 is connected to elbow 445 via flexible plastic tubing 450 (e.g. Tygon®). The internal diameter of the delivery tube 725, stopcock 735, and flexible plastic tubing 450 enable fluid delivery to the IPRP sample holder 400 at a high enough flow rate to maintain the level of fluid in tube 460 at the scribed mark 470 at all times during the measurement. The reservoir 700 has a capacity of approximately 6 liters, although larger reservoirs may be required depending on the sample thickness and permeability. Other fluid delivery systems may be employed provided that they are able to deliver the fluid to the sample holder 400 and maintain the level of fluid in tube 460 at the scribed mark 470 for the duration of the measurement.

The IPRP catchment funnel 500 is shown in FIG. 20 and comprises an outer housing 505 with an internal diameter at the upper edge of the funnel of approximately 125 mm. Funnel 500 is constructed such that liquid falling into the funnel drains rapidly and freely from spout 515. A horizontal flange 520 around the funnel 500 facilitates mounting the funnel in a horizontal position. Two integral vertical internal ribs 510 span the internal diameter of the funnel and are perpendicular to each other. Each rib 510 s 1.5 mm wide and the top surfaces of the ribs lie in a horizontal plane. The funnel housing 500 and ribs 510 are fabricated from a suitably rigid material such as Lexan® or equivalent in order to support sample holder 400. To facilitate loading of the sample it is advantageous for the height of the ribs to be sufficient to allow the upper surface of the bottom plate 405 to lie above the funnel flange 520 when the bottom plate 405 is located on ribs 510. A bridge 530 is attached to flange 520 in order to mount a dial gauge 535 to measure the relative height of the stainless steel weight 415. The dial gauge 535 has a resolution of ±0.01 mm over a range of 25 mm. A suitable digital dial gauge is a Mitutoyo model 575-123 (available from McMaster Carr Co., catalog no. 19975-A73), or equivalent. Bridge 530 has two circular holes 17 mm in diameter to accommodate tubes 425 and 460 without the tubes touching the bridge.

Funnel 500 is mounted over an electronic balance 600, as shown in FIG. 20. The balance has a resolution of ±0.01 g and a capacity of at least 2000 g. The balance 600 is also interfaced with a computer to allow the balance reading to be recorded periodically and stored electronically on the computer. A suitable balance is Mettler-Toledo model PG5002-S or equivalent. A collection container 610 is situated on the balance pan so that liquid draining from the funnel spout 515 falls directly into the container 610.

The funnel 500 is mounted so that the upper surfaces of ribs 510 lie in a horizontal plane. Balance 600 and container 610 are positioned under the funnel 500 so that liquid draining from the funnel spout 515 falls directly into the container 610.

The IPRP sample holder 400 is situated centrally in the funnel 700 with the ribs 510 located in grooves 430. The upper surface of the bottom plate 405 must be perfectly flat and level. The top plate 420 is aligned with and rests on the bottom plate 405. The stainless steel weight 415 surrounds the tube 425 and rests on the top plate 420. Tube 425 extends vertically through the central hole in the bridge 530. The dial gauge 535 is mounted firmly to the bridge 530 with the probe resting on a point on the upper surface of the stainless steel weight 415. The dial gauge is set to zero in this state. The reservoir 700 is filled with 0.9% saline solution and re-sealed. The outlet 740 is connected to elbow 445 via flexible plastic tubing 450.

A an annular sample 475 of the material to be tested is cut by suitable means. The sample has an outer diameter of 70 mm and an inner hole diameter of 12 mm. One suitable means of cutting the sample is to use a die cutter with sharp concentric blades.

The top plate 420 is lifted enough to insert the sample 475 between the top plate and the bottom plate 405 with the sample centered on the bottom plate and the plates aligned. The stopcock 735 is opened and the level of fluid in tube 460 is set to the scribed mark 470 by adjusting the height of the reservoir 700 using the jack 705 and by adjusting the position of the tube 715 in the reservoir. When the fluid level in the tube 460 is stable at the scribed mark 470 and the reading on the dial gauge 535 is constant, the reading on the dial gauge is noted (initial sample thickness) and the recording of data from the balance by the computer is initiated. Balance readings and time elapsed are recorded every 10 seconds for five minutes. After three minutes the reading on the dial gauge is noted (final sample thickness) and the stopcock is closed. The average sample thickness $L_p$ is the average of the initial sample thickness and the final sample thickness expressed in cm.

The flow rate in grams per second is calculated by a linear least squares regression fit to the data between 30 seconds and 300 seconds. The permeability of the material is calculated using the following equation:

$$k = \frac{(Q/\rho)\mu \ln(R_o/R_i)}{2\pi L_p \Delta P}$$

where:
k is the permeability of the material (cm²)
Q is the flow rate (g/s)
ρ is the density of the liquid at 22° C. (g/cm³)
μ is the viscosity of the liquid at 22° C. (Pa·s)
$R_o$ is the sample outer radius (mm)
$R_i$ is the sample inner radius (mm)
$L_p$ is average sample thickness (cm)
ΔP is the hydrostatic pressure (Pa)

$$\Delta P \left( \Delta h - \frac{L_p}{2} \right) G \rho 10$$

where:
Δh is the height of the liquid in tube 460 above the upper surface of the bottom plate (cm), and
G is the gravitational acceleration constant (m/s²)

$$K_r = \frac{k}{\mu}$$

where:
$K_r$ is the IPRP value expressed in units of cm²/(Pa·s)

Discussion of Data in Tables: The information below will provide a basis for including the information found in the tables in the invention.

Table 1 and Table 2: Base substrate material properties for pronounced trilobal shaped fibers, solid round and standard trilobal base substrate as-produced properties. Table 1 describes the base substrate as-produced properties. The table lists the specifics for each example. The important properties to point out in Table 1 are the modification ratio for the pronounced trilobal filaments and the relatively low MD elongation for these point bonded PET substrates.

Table 3: The fluid handling properties of the base substrate are shown. The Holding Capacity of these base substrates indicated that they are not absorbent materials, with gram per gram holding capacities below 10.

Table 4: Lists the process settings and property changes of structured substrates versus the base substrate properties. The examples for the 1D collection of samples highlight a primary purpose in the present invention. 1D is the base substrate (60 g/m² 6.9 dpf PET) while 1D1 through 1D6 show the changes in caliper with increasing fiber displacement, as indicated by the strain depth. Increasing strain increases caliper. The over bonding is indicated by the over thermal bonding. Tip bonding is indicated by FS-Tip and as shown, can also affect the aged caliper and the amount of void volume created. The purpose of the present invention is to create void volume for liquid acquisition. The over thermal bonding also can be used to increase mechanical properties, as illustrated in the MD tensile strength increase vs. the base substrate. The Example 1N data set compare the base substrate with 1N1 through 1N9, which have undergone different strain depth processes. This data set shows that there is an optimization in caliper generation that is determined by any over thermal bonding, FS-tip and overall strain. The data shows that too much strain can produce samples with worse aged caliper. In one execution of the present invention, this would correspond to completely broken filament in the activated region, while the region with the highest void volume creation has the preferred broken filament range. The results also show that similar structured substrate volumes can be created for the present invention as typical resin bonded structures, while also having fluid transport properties.

Table 5: The data and example show that the caliper increase and void volume creation in the present invention can be used for fiber shapes standard trilobal and solid round. The benefit of the present invention is not restricted to pronounced trilobal fibers.

Table 6 lists fluid handling properties of structured substrates vs. base substrate properties. The examples in Table 6 are the same as Table 4. The data in Table 6 show that the use of FDT does increase the MD Horizontal Transport properties of the structured substrate vs. the base substrate. The over bonding has been found to increase fluid transport in the MD. The Vertical wicking height component shows similar properties of the structured substrate vs. the base substrate at moderate FDT strains, but at higher strains the Vertical wicking height component does decrease slightly. Relative to the carded resin bonded nonwovens; the vertical transport component is still very good. The aged strike through data shows a dramatic improvement of fluid acquisition rates of the structured substrate vs. the base substrate. The strike through times decreases dramatically with FDT vs. the base substrate. The rewet properties generally decrease with FDT vs. the base substrate. The data in this Table 6 demonstrates the structured substrate's ability to provide fluid transport along with the ability to control the fluid acquisition rates. The table also includes the fluid permeability of a material via IPRP on the samples, which shows the dramatic improvement after FDT, and also how the structured substrates have higher permeability at calipers similar to the carded resin bonded structures.

Table 7 lists some additional fluid handling properties of some pronounced fiber shaped structured substrates vs. base substrates. The activation conditions used in the sample description are listed in Table 5. Table 5 shows that changes in FDT can improve fluid acquisition rates.

Table 8 shows additional structured substrate vs. base substrate samples with improved fluid acquisition rates for solid round (SR) and standard trilobal fibers (TRI). The activation conditions used for the structured substrate samples are provided in Table 9.

Table 9 lists the process conditions for the samples made in Table 8.

Table 10 lists the single fiber property values for substrates used in the present invention. Because the present invention uses high speed fiber spinning to produce thermal stable PET, the modulus values are very high for fibers having strength >10 g per filament.

TABLE 1

Base Substrate example material properties.

| Example Designation | Resin Type | Mass Throughput | Shape | Acutal Basis Weight (g/m²) | Aged Caliper (mm) | Mod Ratio | Actual Denier (dpf) | MD Tensile Strength (N/5 cm) | MD Elongation at Peak (%) | CD Tensile Strength (N/5 cm) | CD Elongation at Peak (%) | MD/CD Ratio |
|---|---|---|---|---|---|---|---|---|---|---|---|---|
| 1D | F61HC/9921 | 3GHM | p-TRI | 60.6 | 0.36 | 1.72 | 6.9 | 96.9 | 4 | 60.3 | 33 | 1.61 |
| 1F | F61HC/9921 | 4GHM | p-TRI | 41.1 | 0.35 | 2.09 | 8.6 | 80.6 | 26 | 39.5 | 35 | 2.04 |
| 1N | F61HC/9921 | 4GHM | p-TRI | 44.1 | 0.39 | 1.72 | 6.9 | 61.7 | 5 | 36.2 | 36 | 1.7 |
| 1O | F61HC/9921 | 4GHM | p-TRI | 67.0 | 0.43 | 1.72 | 6.9 | 120.0 | 6 | 67.2 | 33 | 1.8 |
| 2K | F61HC | 4GHM | p-TRI | 40.6 | 0.32 | 1.98 | 9.2 | 82.5 | 28 | 38.2 | 32 | 2.16 |
| 3E | F61HC/9921 | 4.0 | std-TRI | 41.7 | 0.29 | 1.18 | 10.5 | 74.3 | 29 | 42.5 | 41 | 1.75 |
| 4B | F61HC/9921 | 3GHM | SR | 42.7 | 0.36 | N/A | 4.9 | 58.0 | 24.0 | 50.2 | 39.0 | 1.2 |

TABLE 2

Base Substrate material properties.

| Example Designation | Fiber Perimeter (μm) | Equivalent SR Fiber Diameter (μm) | Actual Basis Weight (g/m²) | Aged Caplier (mm) | Opacity (%) | Base Substrate Specific Density (g/m3) | Base Substrate Specific Volume (cm3/g) |
|---|---|---|---|---|---|---|---|
| 1D | 99.7 | 26.8 | 60.6 | 0.36 | 40 | 168333 | 5.94 |
| 1F | 135.5 | 30.0 | 41.1 | 0.35 | 25 | 117429 | 8.52 |
| 1N | 135.5 | 30.0 | 44.1 | 0.39 | | 113077 | 8.84 |
| 1O | 135.5 | 30.0 | 67.0 | 0.43 | | 155814 | 6.42 |
| 2K | 138.0 | 31.0 | 40.6 | 0.32 | | 126875 | 7.88 |
| 3E | 33.2 | 118 | 41.7 | 0.29 | 26 | 143793 | 6.95 |
| 4B | 71.0 | 22.6 | 42.7 | 0.36 | 16 | 118611 | 8.43 |

TABLE 3

Base Substrate fluid handling properties.

| Example Designation | Line Speed (m/min) | Bonding Temperature, Engraved/Smooth (° C.) | Surfactant | Holding Capacity w/SRP (g/g) | Wicking Spread MD (cm) | CD (cm) | Vertical Wicking Height (mm) | FDT | Thermally Stable? | % Shrinkage |
|---|---|---|---|---|---|---|---|---|---|---|
| 1D | 23 | 200/190 | DP988A | 4.33 | 26.0 | 16.0 | 108 | NO | YES | 2 |
| 1F | 43 | 200/190 | DP988A | 5.20 | 18.0 | 16.0 | 27 | NO | YES | 5 |
| 1N | 44 | 210/200 | DP988A | | 19 | 17 | 51 | NO | YES | 2 |
| 1O | 30 | 210/200 | DP988A | | 30 | 21 | 80 | NO | YES | 0 |
| 2K | 43 | 200/190 | DP988A | 5.30 | 13.0 | 11.0 | | NO | YES | 3 |

TABLE 3-continued

Base Substrate fluid handling properties.

| Example Designation | Line Speed (m/min) | Bonding Temperature, Engraved/Smooth (° C.) | Surfactant | Holding Capacity w/SRP (g/g) | Wicking Spread MD (cm) | CD (cm) | Vertical Wicking Height (mm) | FDT | Thermally Stable? | % Shrinkage |
|---|---|---|---|---|---|---|---|---|---|---|
| 3E | 43 | 200/190 | DP988A | 4.8 | 2.5 | 2.5 | 22 | NO | YES | 2 |
| 4B | 31 | 200/190 | DP988A | 4.00 | 11.9 | 9.0 | 29 | NO | YES | 4 |

TABLE 4

Mechanical Property changes of Base Substrate vs. Structured substrate.

| Example Designation | Basis Weight (g/m²) | FDT | Strain Depth (inches) | Line Speed (MPM) | Over Thermal Bond | FS-Tip | Fresh Caliper (mm) | Aged Caliper (mm) | Base Substrate Specific Volume (cm3/g) | Structured Substrate Specific Volume (cm3/g) | Void Volume Creation (cm3/g) | MD Tensile Strength N/5 cm) | MD Elongation at Peak (%) |
|---|---|---|---|---|---|---|---|---|---|---|---|---|---|
| 1D | 60.1 | NO | NO | NO | NO | NO | 0.36 | 0.35 | 5.82 | | | 96.3 | 4 |
| 1D1 | 60.1 | YES | 0.01 | 17 | YES | NO | No Data | No Data | | | | 90.5 | 5 |
| 1D2 | 60.1 | YES | 0.01 | 17 | YES | NO | 0.42 | 0.38 | | 6.32 | 0.50 | 154.1 | 26 |
| 1D3 | 60.1 | YES | 0.07 | 17 | YES | NO | 0.53 | 0.48 | | 7.99 | 2.16 | 147.7 | 23 |
| 1D4 | 60.1 | YES | 0.07 | 17 | YES | YES | No Data | No Data | | | | 152.1 | 26 |
| 1D5 | 60.1 | YES | 0.13 | 17 | YES | YES | 0.90 | 0.74 | | 12.31 | 6.49 | 127.6 | 37 |
| 1D6 | 60.1 | YES | 0.13 | 17 | YES | NO | 0.84 | 0.58 | | 9.65 | 3.83 | 109.8 | 41 |
| Resin Bond 43 g/m² | 43 | NO | NO | NO | NO | NO | 0.80 | 0.63 | 14.65 | | | | |
| Resin Bond 60 g/m² | 60 | NO | NO | NO | NO | NO | 1.14 | 0.91 | 15.17 | | | | |
| 1N | 44.1 | NO | NO | NO | NO | NO | 0.4 | 0.4 | 9.07 | | 0.00 | | |
| 1N1 | 44.1 | YES | 0.1 | 17 | YES | NO | 0.84 | 0.72 | | 16.33 | 7.26 | | |
| 1N2 | 44.1 | YES | 0.1 | 17 | YES | YES | 0.76 | 0.7 | | | | 15.87 | 6.80 |
| 1N3 | 44.1 | YES | 0.1 | 17 | NO | NO | 0.91 | 0.79 | | | | 17.91 | 8.84 |
| 1N4 | 44.1 | YES | 0.1 | 17 | NO | YES | 0.75 | 0.65 | | | | 14.74 | 5.67 |
| 1N5 | 44.1 | YES | 0.13 | 17 | YES | YES | 1.2 | 0.83 | | | | 18.82 | 9.75 |
| 1N6 | 44.1 | YES | 0.13 | 17 | YES | NO | 1.31 | 0.69 | | | | 15.65 | 6.58 |
| 1N9 | 44.1 | YES | 0.16 | 17 | YES | YES | 1.17 | 0.65 | | | | 14.74 | 5.67 |

TABLE 5

Mechanical Property changes of Base Substrate vs. Structured Substrate.

| Example Designation | Basis Weight (g/m²) | FDT | Strain Depth (inches) | Line Speed (MPM) | Over Thermal Bond | FS-Tip | Fresh Caliper (mm) | Aged Caliper (mm) | Base Substrate Specific Volume (cm3/g) | Structured Substrate Specific Volume (cm3/g) | Void Volume Creation (cm3/g) |
|---|---|---|---|---|---|---|---|---|---|---|---|
| 1O | 67.0 | NO | NO | NO | NO | NO | 0.43 | 0.43 | 6.42 | | 0.00 |
| 1O1 | 67.0 | YES | 0.1 | 17 | YES | NO | 0.89 | 0.80 | | 11.94 | 5.52 |
| 1O2 | 67.0 | YES | 0.1 | 17 | YES | YES | 0.81 | 0.75 | | 11.19 | 4.78 |
| 1O3 | 67.0 | YES | 0.1 | 17 | NO | NO | 0.99 | 0.86 | | 12.84 | 6.42 |
| 1O4 | 67.0 | YES | 0.13 | 17 | YES | NO | 1.45 | 1.00 | | 14.93 | 8.51 |
| 1O5 | 67.0 | YES | 0.13 | 17 | YES | YES | 1.31 | 1.11 | | 16.57 | 10.15 |
| 1O6 | 67.0 | YES | 0.13 | 17 | NO | NO | 1.34 | 0.90 | | 13.43 | 7.01 |
| 1K | 40.6 | NO | NO | NO | NO | NO | 0.32 | 0.32 | 7.88 | | 0.00 |
| 1K1 | 40.6 | YES | 0.13 | 17 | YES | YES | 0.94 | 0.48 | | 11.82 | 3.94 |
| 1F | 41.1 | NO | NO | NO | NO | NO | 0.35 | 0.35 | 8.52 | | 0.00 |
| 1F1 | 41.1 | YES | 0.13 | 17 | YES | YES | 0.92 | 0.52 | | 12.65 | 4.14 |
| 4B | 42.7 | NO | NO | NO | NO | NO | 0.36 | 0.36 | 8.43 | | 0.00 |
| 4B1 | 42.7 | YES | 0.07 | 17 | YES | YES | 0.56 | 0.49 | | 11.48 | 3.04 |
| 4B2 | 42.7 | YES | 0.13 | 17 | YES | YES | 1.07 | 0.50 | | 11.71 | 3.28 |
| 3E | 41.7 | NO | NO | NO | NO | NO | 0.31 | 0.31 | 7.43 | | 0.00 |
| 3E1 | 41.7 | YES | 0.07 | 17 | YES | YES | 0.42 | 0.33 | | 7.91 | 0.48 |
| 3E2 | 41.7 | YES | 0.13 | 17 | YES | YES | 0.62 | 0.38 | | 9.11 | 1.68 |

TABLE 6

Fluid Management Properties of Base Substrate and Structured Substrates.

| Example Designation | Fresh Caliper (mm) | Aged Caliper (mm) | FDT | IPRP cm²/(Pa s) | MD Horizontal Transport (cm) | Vertical Wicking Height (cm) | Aged Strike Through 1 (s) | Aged Strike Through 2 (s) | Aged Strike Through 3 (s) | Rewet (g) |
|---|---|---|---|---|---|---|---|---|---|---|
| 1D | 0.36 | 0.35 | NO | 5,060 | 19.5 | 10.8 | 1.2 | 1.8 | 1.7 | 1.5 |
| 1D1 | No Data | No Data | YES | | 20.0 | 10.7 | | | | |
| 1D2 | 0.42 | 0.38 | YES | 11,200 | 23.0 | 10.8 | 0.5 | 1.2 | 1.4 | 0.8 |
| 1D3 | 0.53 | 0.48 | YES | 13,400 | 25.0 | 11.0 | 0.6 | 1.3 | 1.3 | 2.0 |
| 1D4 | No Data | No Data | YES | | 25.0 | 9.0 | | | | |
| 1D5 | 0.90 | 0.74 | YES | 24,500 | 27.0 | 8.0 | 0.4 | 0.7 | 0.7 | 0.2 |
| 1D6 | 0.84 | 0.58 | YES | 17,300 | 23.0 | 8.0 | 0.6 | 0.7 | 0.5 | 0.1 |
| Resin Bond 43 g/m² | 0.80 | 0.63 | NO | 11,900 | 2 | 0 | 0.7 | 1.2 | 1.1 | 0.0 |
| Resin Bond 60 g/m² | 1.14 | 0.91 | NO | 13,200 | 2 | 0 | 0.5 | 1.0 | 0.9 | 0.1 |
| 1N | 0.4 | 0.4 | NO | 7,900 | 19.0 | 8.1 | 1.2 | 1.4 | 1.6 | 1.3 |
| 1N1 | 0.84 | 0.72 | YES | 29,439 | 20.0 | 8.2 | 0.3 | 0.7 | 0.6 | 0.9 |
| 1N2 | 0.76 | 0.7 | YES | 30,320 | 21.0 | 8.4 | 0.4 | 0.9 | 0.9 | 1.2 |
| 1N3 | 0.91 | 0.79 | YES | 22,934 | 21.0 | 8.3 | 0.2 | 0.8 | 0.8 | 0.9 |
| 1N4 | 0.75 | 0.65 | YES | 19,132 | 22.0 | 7.8 | 0.4 | 1.0 | 0.6 | 1.5 |
| 1N5 | 1.2 | 0.83 | YES | 24,634 | 22.0 | 7.7 | 0.0 | 0.7 | 0.6 | 0.2 |
| 1N6 | 1.31 | 0.69 | YES | 17,455 | 21.0 | 7.7 | 0.4 | 0.7 | 0.4 | 0.5 |
| 1N9 | 1.17 | 0.65 | YES | 10,795 | 22.5 | 6.8 | 0.0 | 0.6 | 0.6 | 0.2 |

TABLE 7

Fluid Management Properties of Base Substrate and Structured substrates.

| Example Designation | Fresh Caliper (mm) | Aged Caliper (mm) | FDT | IPRP cm²/(Pa s) | MD Horizontal Transport (cm) | Vertical Wicking Height (cm) | Aged Strike Through 1 (s) | Aged Strike Through 2 (s) | Aged Strike Through 3 (s) | Rewet (g) |
|---|---|---|---|---|---|---|---|---|---|---|
| 1O | 0.43 | 0.43 | NO | 5,060 | 30.0 | 13.5 | 1.2 | 1.8 | 1.7 | 1.5 |
| 1O1 | 0.89 | 0.80 | YES | 31,192 | 32.0 | 13.7 | 0.0 | 0.1 | 0.5 | 1.8 |
| 1O2 | 0.81 | 0.75 | YES | 32,134 | 33.0 | 14.1 | 0.6 | 0.5 | 0.8 | 1.9 |
| 1O3 | 0.99 | 0.86 | YES | 29,158 | 33.0 | 12.6 | 0.1 | 0.5 | 0.2 | 1.8 |
| 1O4 | 1.45 | 1.00 | YES | 32,288 | 32.5 | 12.3 | 0.2 | 0.3 | 0.4 | 0.5 |
| 1O5 | 1.31 | 1.11 | YES | 39,360 | 33.0 | 12.4 | 0.4 | 0.1 | 0.3 | 0.5 |
| 1O6 | 1.34 | 0.90 | YES | 26,298 | 32.0 | 12.5 | 0.0 | 0.1 | 0.5 | 0.7 |

TABLE 8

Fluid Management Properties of Different Shaped Fibers.

| Example Designation | Fiber Shape | Fresh Caliper (mm) | Aged Caplier (mm) | FDT | MD Horizontal Transport (cm) | Vertical Wicking Height (cm) | Aged Strike Through 1 (s) | Aged Strike Through 2 (s) | Aged Strike Through 3 (s) | Rewet (g) |
|---|---|---|---|---|---|---|---|---|---|---|
| 3E | TRI | 0.29 | 0.29 | NO | 2.5 | 2.2 | 1.1 | 1.3 | 1.6 | 1.2 |
| 3E1 | TRI | 0.48 | 0.42 | YES | 4.0 | 2.9 | 0.49 | 1.01 | 1.03 | 0.29 |
| 3E2 | TRI | 0.66 | 0.48 | YES | 3.0 | 2.7 | 0.53 | 0.73 | 0.70 | 0.33 |
| 4B | SR | 0.36 | 0.36 | NO | 11.9 | 2.9 | 1.3 | 1.5 | 1.7 | 1.3 |
| 4B1 | SR | 0.43 | 0.41 | YES | 14.1 | 4.8 | 0.79 | 1.10 | 1.13 | 0.71 |
| 4B2 | SR | 0.56 | 0.52 | YES | 13.2 | 4.6 | 0.60 | 0.94 | 0.93 | 0.07 |
| Resin Bond 43 g/m² | | 0.80 | 0.63 | | 2 | 0 | 0.68 | 1.19 | 1.10 | 0.04 |
| Resin Bond 60 g/m² | | 1.14 | 0.91 | | 2 | 0 | 0.49 | 1.04 | 0.85 | 0.06 |

TABLE 9

Process settings for samples in Table 8.

| Example Designation | FDT | Strain Depth (inches) | Line Speed (MPM) | Over Thermal Bond (inches) | FS-Tip | Fresh Caliper (mm) | Aged Caliper (mm) |
|---|---|---|---|---|---|---|---|
| 4B1 | YES | 0.07 | 17 | YES | YES | 0.48 | 0.42 |
| 4B2 | YES | 0.13 | 17 | YES | YES | 0.66 | 0.48 |
| 3E1 | YES | 0.07 | 17 | YES | YES | 0.43 | 0.41 |
| 3E2 | YES | 0.13 | 17 | YES | YES | 0.56 | 0.52 |

TABLE 10

Single fiber property data for sample used in present invention.

| Fiber Shape | Polymer Type | Fiber Denier (dpf) | Peak Fiber Load (g) | Strain at Break (%) | Modulus (GPa) |
|---|---|---|---|---|---|
| Pronounced Trilobal | PET | 6.9 | 15.1 | 94 | 4.3 |
| Pronounced Trilobal | PET | 8.6 | 15.6 | 126 | 3.5 |
| Pronounced Trilobal | PET | 10.7 | 15.3 | 170 | 3.2 |
| Pronounced Trilobal | PET | 13.0 | 15.5 | 186 | 3.4 |
| Standard Trilobal | PET | 6.5 | 15.3 | 165 | 3.8 |
| Standard Trilobal | PET | 9.6 | 15.9 | 194 | 2.7 |
| Standard Trilobal | PET | 10.5 | 16.0 | 247 | 2.4 |
| Standard Trilobal | PET | 14.5 | 17.5 | 296 | 2.6 |
| Solid Round | PET | 2.9 | 10.0 | 167 | 3.0 |
| Solid Round | PET | 4.9 | 15.6 | 268 | 2.8 |
| Solid Round | PET | 8.9 | 15.9 | 246 | 3.3 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a chassis including a topsheet and a backsheet;
an absorbent core located between the topsheet and the backsheet; and
an acquisition system located between the topsheet and the absorbent core, wherein the acquisition system includes a structured fibrous web comprising thermoplastic fibers having a modulus of at least about 0.5 GPa forming a fibrous web that is thermally stable; the structured fibrous web comprising a first surface and a second surface, a first region and a plurality of discrete second regions disposed throughout the first region, the second regions form discontinuities on the second surface and displaced fibers on the first surface, wherein portions of the displaced fibers distal from the second surface are melt-bonded such that adjacent fibers are at least partially joined together to form melt-bonded portions, wherein at least about 50% and less than about 100% of the displaced fibers in each second region are fixed along a first side of the second region and separated proximate to the first surface along a second side of the second region opposite the first side forming loose ends extending away from the first surface, and wherein the displaced fibers forming loose ends provide access to void volume inside the discontinuities for collecting fluid.

2. The disposable absorbent article of claim 1, wherein the structured fibrous web further comprises a plurality of over-bonded regions disposed throughout the first region.

3. The disposable absorbent article of claim 2, wherein in each of the overbonded regions of the structured fibrous web, the first region and the second regions have an aged caliper, wherein the aged caliper of the second regions formed by the loose ends of the displaced fibers is less than about 1.5 mm which is greater than the aged caliper of the first region and the aged caliper of the first region is greater than the aged caliper of the overbonded regions.

4. The disposable absorbent article of claim 2, wherein the overbonded regions of the structured fibrous web are continuous.

5. The disposable absorbent article of claim 2, wherein the overbonded regions of the structured fibrous web form a continuous network.

6. The disposable absorbent article of claim 2, wherein the overbonded regions of the structured fibrous web cover less than about 75% of the total surface area of the first surface or the second surface of the fibrous web.

7. The disposable absorbent article of claim 1, wherein the thermally stable fibrous web allows shrinkage of less than about 30%.

8. The disposable absorbent article of claim 1, wherein the fibers of the structured fibrous web are continuous spunbond fibers.

9. The disposable absorbent article of claim 8, wherein the spunbond fibers of the structured fibrous web are uncrimped.

10. The disposable absorbent article of claim 1, wherein in the structured fibrous web the loose ends of the displaced fibers are thermally bonded together.

11. The disposable absorbent article of claim 1, wherein in the structured fibrous web the second regions form less than about 75% of the total surface area of the first surface or the second surface of the fibrous web.

12. The disposable absorbent article of claim 1, wherein the structured fibrous web is non-extensible.

13. The disposable absorbent article of claim 1, wherein the fibers of the structured fibrous web are non-extensible.

14. The disposable absorbent article of claim 1, wherein the fibers of the structured fibrous web are formed from a thermoplastic polymer comprising polyester.

15. The disposable absorbent article of claim 1, wherein the fibers of the structured fibrous web comprise PET.

16. The disposable absorbent article of claim 1, wherein the fibers of the structured fibrous web comprise PET and coPET.

17. The disposable absorbent article of claim 1, wherein the fibers of the structured fibrous web comprise multi-lobal shaped fibers.

18. The disposable absorbent article of claim 17, wherein the multi-lobal shaped fibers comprise fibers selected from the group consisting of trilobal shape, delta shape, star shape, triangular shape and combinations thereof.

19. The disposable absorbent article of claim 1, wherein the fibers of the structured fibrous web have a modulus of at least about 2.0 GPa.

20. The disposable absorbent article of claim 1, wherein the fibers of the structured fibrous web have a modulus of at least about 3.0 GPa.

21. The disposable absorbent article of claim 1, wherein the fibers of the structured fibrous web have a denier of at least about 3 dpf.

22. The disposable absorbent article of claim 1, wherein the structured fibrous web has a structured substrate specific volume of at least about 5 cm3/g.

23. The disposable absorbent article of claim 1, wherein the structured fibrous web is hydrophilic.

24. A disposable absorbent article comprising:
a chassis including a topsheet and a backsheet;
an absorbent core located between the topsheet and the backsheet; and
an acquisition system located between the topsheet and the absorbent core, wherein the acquisition system includes a structured fibrous web comprising non extendable thermoplastic fibers having a modulus of at least about 0.5 GPa, the structured fibrous web being formed from a base substrate, the base substrate being a fully bonded, non extensible fibrous base web that is thermally stable; the structured fibrous web comprising a first surface and a second surface, a first region and a plurality of discrete second regions disposed throughout the first region, the second regions form discontinuities on the second surface and displaced fibers on the first surface, wherein portions of the displaced fibers distal from the second surface are melt-bonded such that adjacent fibers are at least partially joined together to form melt-bonded portions, and wherein the displaced fibers forming loose ends provide access to void volume inside the discontinuities for collecting fluid.

25. The disposable absorbent article of claim 24, wherein the absorbent core comprises absorbent material comprising absorbent particulate polymer material, the absorbent particulate polymer material being present in an amount greater than about 80% by weight of the absorbent material of the absorbent core.

26. A disposable absorbent article comprising:
a chassis including a topsheet and a backsheet;
an absorbent core located between the topsheet and the backsheet; and
an acquisition system located between the topsheet and the absorbent core, wherein the acquisition system includes a structured fibrous web comprising thermoplastic fibers having a modulus of at least about 0.5 GPa forming a fibrous web that is thermally stable; the structured fibrous web comprising a first surface and a second surface, a first region and a plurality of discrete second regions disposed throughout the first region, the second regions form discontinuities on the second surface and displaced fibers on the first surface, wherein portions of the displaced fibers distal from the second surface are melt-bonded such that adjacent fibers are at least partially joined together to form melt-bonded portions, and wherein at least about 50% and less than about 100% of the displaced fibers in each second region are fixed along a first side of the second region and separated proximate to the first surface along a second side of the second region opposite the first side forming loose ends extending away from the first surface, wherein the loose ends of the displaced fibers are thermally bonded together, and wherein the displaced fibers forming loose ends provide access to void volume for collecting fluid.

* * * * *